US008034347B2

(12) United States Patent
Hempstead et al.

(10) Patent No.: US 8,034,347 B2
(45) Date of Patent: Oct. 11, 2011

(54) METHOD FOR INHIBITING APOPTOSIS THROUGH THE P75 NEUROTROPHIN RECEPTOR

(75) Inventors: Barbara L. Hempstead, New York, NY (US); Ramee Lee, New York, NY (US); Kenneth K. Teng, New York, NY (US); Pouneh Kermani, Great Neck, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 769 days.

(21) Appl. No.: 11/881,763

(22) Filed: Jul. 27, 2007

(65) Prior Publication Data

US 2008/0025978 A1    Jan. 31, 2008

Related U.S. Application Data

(63) Continuation of application No. 10/155,886, filed on May 24, 2002, now Pat. No. 7,507,799.

(60) Provisional application No. 60/293,823, filed on May 25, 2001, provisional application No. 60/305,510, filed on Jul. 13, 2001.

(51) Int. Cl.
*A61K 39/395* (2006.01)

(52) U.S. Cl. .................................................. 424/158.1

(58) Field of Classification Search ........................ None
See application file for complete search history.

(56) References Cited

U.S. PATENT DOCUMENTS

| | | | |
|---|---|---|---|
| 5,169,764 | A | 12/1992 | Shooter et al. |
| 5,288,622 | A | 2/1994 | Gray et al. |
| 6,077,829 | A | 6/2000 | Tanaka et al. |
| 6,172,086 | B1 | 1/2001 | Zelle et al. |
| 7,507,799 | B2 | 3/2009 | Hempstead et al. |

FOREIGN PATENT DOCUMENTS

| | | |
|---|---|---|
| WO | WO 97/36607 A1 | 10/1997 |
| WO | WO00/24415 A3 | 5/2000 |
| WO | WO 00/75278 A2 | 12/2000 |
| WO | WO 01/52843 A1 | 7/2001 |
| WO | WO 02/096356 A3 | 12/2002 |

OTHER PUBLICATIONS

Botchkarev, et al., "A role for p75 neurotrophin receptor in the control of apoptosis-driven hair follicle regression", *The FASEB Journal* 2000, 14:1931-1942.
Chao, et al., "Neurotrophins: To Cleave or Not to Cleave", *Neuron* 2002, 33:9-12.
Chen, et al., "Characterization of nerve growth factor precursor protein expression in rat round spermatids and the trophic effects of nerve growth factor in the maintenance of Sertoli cell viability", *Molecular and Cellular Endocrinology* 1997, 127:129-136.
Delsite, et al., "Characterization of Nerve Growth Factor Precursor Protein Expression by Human Prostate Stromal Cells: A Role in Selective Neurotrophin Stimulation of Prostate Epithelial Cell Growth", *The Prostate* 1999, 41:39-48.
Drinkwater, et al., "The Carboxyl Terminus of Nerve Growth Factor is Required for Biological Activity", *The Journal of Biological Chemistry* 1993, 268(31):23202-23207.
Heymach, Jr., et al., "The Regulated Secretion and Vectorial Targeting of Neurotrophins in Neuroendocrine and Epithelial Cells", *The Journal of Biological Chemistry* 1996, 271(41):25430-25437.
Heymach, Jr., et al., "The Biosynthesis of Neurotrophin Heterodimers by Transfected Mammalian Cells", *The Journal of Biological Chemistry* 1995, 270(20):12297-12304.
Kolbeck, et al., "Characterisation of neurotrophin dimers and monomers", *Eur. J. Biochem.* 1994, 225:995-1003.
Lee, et al., "Regulation of Cell Survival by Secreted Proneurotrophins", *Science* 2001, 294:1945-1948.
Mowla, et al., "Biosynthesis and Post-translational Processing of the Precursor to Brain-derived Neurotrophic Factor", *The Journal of Biological Chemistry* 2001, 276(16):12660-12666.
Rattenholl, et al., "Pro-Sequence Assisted Folding and Disulfide Bond Formation of Human Nerve Growth Factor", *J. Mol. Biol.* 2001, 305:523-533.
Seidah, et al., "Cellular processing of the neurotrophin precursors of NT3 and BDNF by the mammalian proprotein convertases", *FEBS Letters* 1996, 379:247-250.
Suter, et al., "NGF/BDNF Chimeric Proteins: Analysis of Neurotrophin Specificity by Homolog-scanning Mutagenesis", *The Journal of Neuroscience* 1992, 12(1):306-318.
Suter, et al., "Two conserved domains in the NGF propeptide are necessary and sufficient for the biosynthesis of correctly processed and biologically active NGF", *The EMBO Journal* 1991, 10(9):2395-2400.
Wang, et al., "p75$^{NTR}$ Mediates Neurotrophin-Induced Apoptosis of Vascular Smooth Muscle Cells", *American Journal of Pathology* 2000, 157(4):1247-1258.
Yardley, et al., "Expression of nerve growth factor mRNA and its translation products in the anagen hair follicle", *Experimental Dermatology* 2000, 9:283-289.

(Continued)

*Primary Examiner* — Robert C Hayes
(74) *Attorney, Agent, or Firm* — Scully, Scott, Murphy & Presser, P.C.

(57) ABSTRACT

The present invention provides an isolated protein comprising a pro-domain of a proneurotrophin, methods for producing the protein, and pharmaceutical compositions containing the isolated protein. The invention also provides a nucleic acid molecule which encodes the protein and a vector containing the nucleic acid molecule. The present invention further provides a method for cleaving a proneurotrophin protein to a mature neurotrophin. In addition, the invention relates to methods for inducing apoptosis in a cell of a mammal expressing p75 surface receptors or p75 and trk receptors. The methods include causing the p75 receptor to bind a pharmaceutical composition containing a pro-domain of a proneurotrophin or administering to the mammal an effective amount of a cleavage-resistant proneurotrophin and an inhibitor of trk activation. The invention also relates to a method for inhibiting apoptosis of a cell in a mammal by administering an effective amount of a molecule which inhibits binding of a proneurotrophin to a p75 receptor. Also provided, are kits and methods for screening a human for a condition associated with undesired apoptosis.

35 Claims, 29 Drawing Sheets

OTHER PUBLICATIONS

Akinaga, et al., "Antitumor effect of KT6124, a novel derivative of protein kinase inhibitor K-252a, and its mechanism of action", *Cancer Chemother Pharmacol* 1992, 29: 266-272.

Barker, et al., "p75NTR Is Positively Promiscuous: Novel Partners and New Insights", *Neuron* 2004, 42:529-533.

Brann, et al., "Ceramide Signaling Downstream of the P75 Neurotrophin Receptor Mediates the Effects of Nerve Growth Factor on Outgrowth of Cultured Hippocampal Neurons", *J. Neurosci* 1999, 19(19):8199-8206.

Evans, et al., "Antitumor Activity of CEP-751 (KT-6587) on Human Neuroblastoma and Medulloblastoma Xenografts", *Clin. Cancer Res.* 1999, 5(11):3594-3602.

Fahnestock, et al., "The Precursor Pro-Nerve Growth Factor Is the Predominant Form of Nerve Growth Factor in Brain and Is Increased in Alzheimer's Disease", *Molecular and Cellular Neuroscience* 2001, 18:210-220.

Fotouhi, et al., "Potent Peptide Inhibitors of Stromelysin Based on the Prodomain Region of Matrix Metalloproteinases", *The Journal of Biological Chemistry* 1994, 269(48):30227-30231.

Frade, et al., "Induction of cell death by endogenous nerve growth factor through its p75 receptor", *Letters to Nature* 1996, 383(6596):166-168.

Mizushima, et al., "Antitumor Therapeutic Effect of Neurotropin on Transplanted Tumors in Rats", *Oncology* 1984, 41:289-292.

Reinshagen, et al., "Commercial mouse and human nerve growth factors contain nerve growth factor prohormone isoforms", *Journal of Neuroscience Methods* 1997, 76(1):75-81.

Rowinsky, et al., "Phase I and Pharmacologic Study of the Specific Matrix Metalloproteinase Inhibitor BAY 12-9566 on a Protracted Oral Daily Dosing Schedule in Patients With Solid Malignancies", *Journal of Clinical Oncology* 2000, 18(1):178-186.

Cortazzo, MH, et al., "Nerve Growth Factor (NGF)-Mediated Protection of Neural Crest Cells from Antimitotic Agent-Induced Apoptosis: the Role of the Low Affinity NGF Receptor", *The Journal of Neuroscience*, vol. 16, No. 2, pp. 3895-3899; Jun. 15, 1996.

Gentry JJ. et al.; "Nerve Growth Factor Activation of Nuclear Factor .kapp.B through Its p75 Receptor Is an Anti-apoptotic Signal in RN22 Schwannoma Cells", *The Journal of Biological Chemistry*, vol. 275, No. 11, pp. 7558-7565; Mar. 17, 2000.

Soilu-Haenninen M. et al., "Nerve Growth Factor Signaling Through p75 induces apoptosis in Schwann cells via a Bcl-2-independent pathway", *Journal of Neuroscience*, vol. 19, No. 12, pp. 4828-4838; Jun. 15, 1999.

Nykjaer A. et al., "Sortilin is Essential for proNGF-induced Neuronal Cell Death", *Nature*, vol. 427, pp. 843-848; Feb. 26, 2004. (Abstract).

Capsoni, S., et al., "Dissecting the involvement of tropomyosin-related kinase A and p75 neurotrophin receptor signaling in NGF deficit-induced neurodegeneration", *Proc. Natl. Acad. Sci. USA*, vol. 107, pp. 12299-12304 (2010).

Feng, D., et al., "Molecular and Structural Insight into proNGF Engagement of p75NTR and Sortilin", *J. Mol. Biol.*, 396, pp. 967-984 (2010).

He, X. and Garcia, K.L., "Structure of Nerve Growth Factor Complexed with the Shared Neurotrophin Receptor p75", *Science*, vol. 304, pp. 870-875, May 7, 2004.

Frade, J.M. et al., "Control of early cell death by BDNF in the chick retina", *Development*, vol. 124, pp. 3313-3320 (1997).

Das, A., et al., "Time-Dependent Increases in Protease Activities for Neuronal Apoptosis in Spinal Cords of Lewis Rats During Development of Acute Experimental Autoimmune Encephalomyelitis", *Journal of Neuroscience Research*, vol. 86, pp. 2992-3001 (2008).

Figure 1A: Primary Protein Sequence from Human NGF (Gen Bank Accession Number: AAA59931)

```
  1 msmlfytlit afligiqaep hsesnvpagh tipqvhwtkl qhsldtalrr arsapaaaia
 61 arvagqtrni tvdprlfkkr rlrsprvlfs tqppreaadt qdldfevgga apfnrthrsk
121 rssshpifhr gefsvcdsvs vwvgdkttat dikgkevmvl gevninnsvf kqyffetkcr
181 dpnpvdsgcr gidskhwnsy ctthtfvka ltmdgkqaaw rfiridtacv cvlsrkavrr
241 a
```

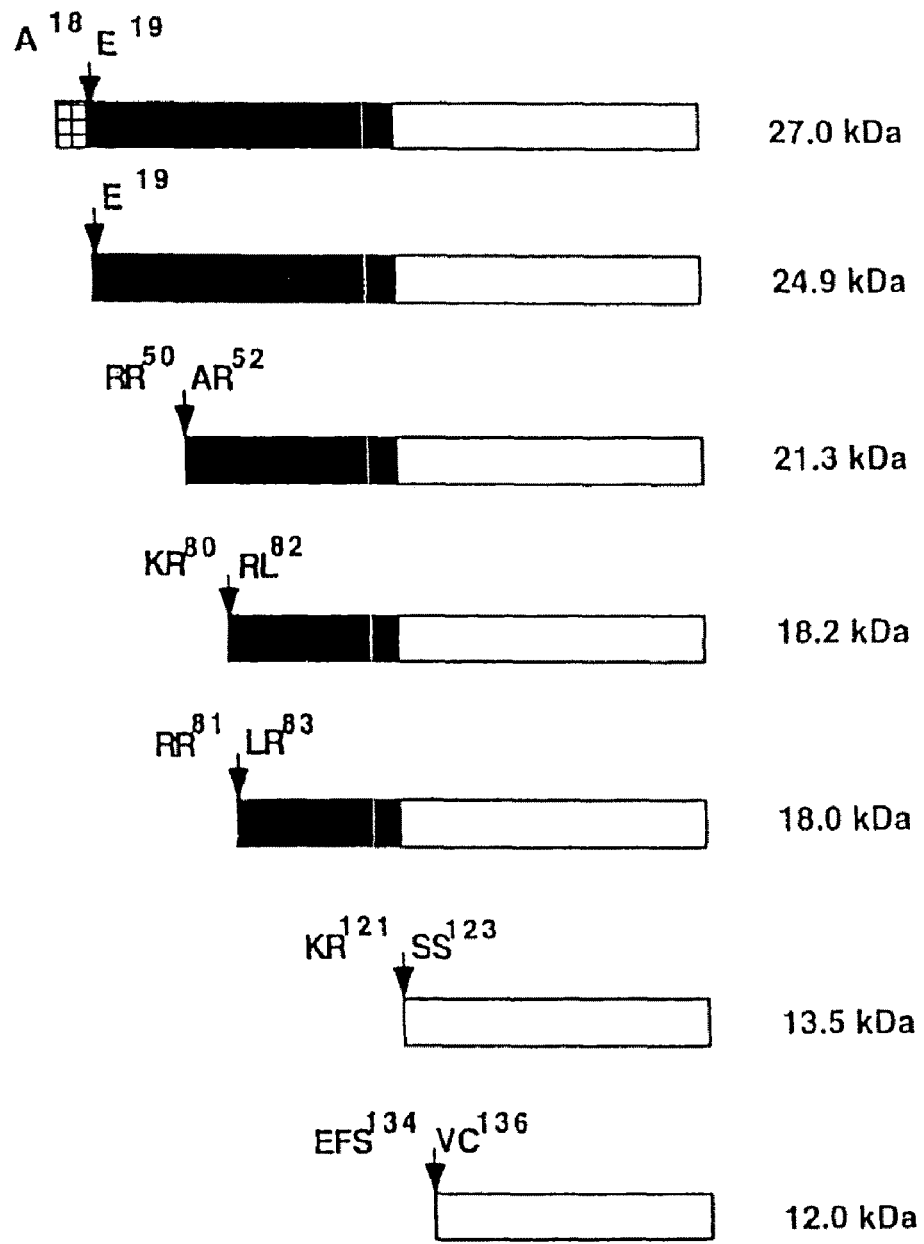
Figure 1B: Schematic Representation of Monomeric, Un-glycosylated NGF Isoforms According to Prior Art

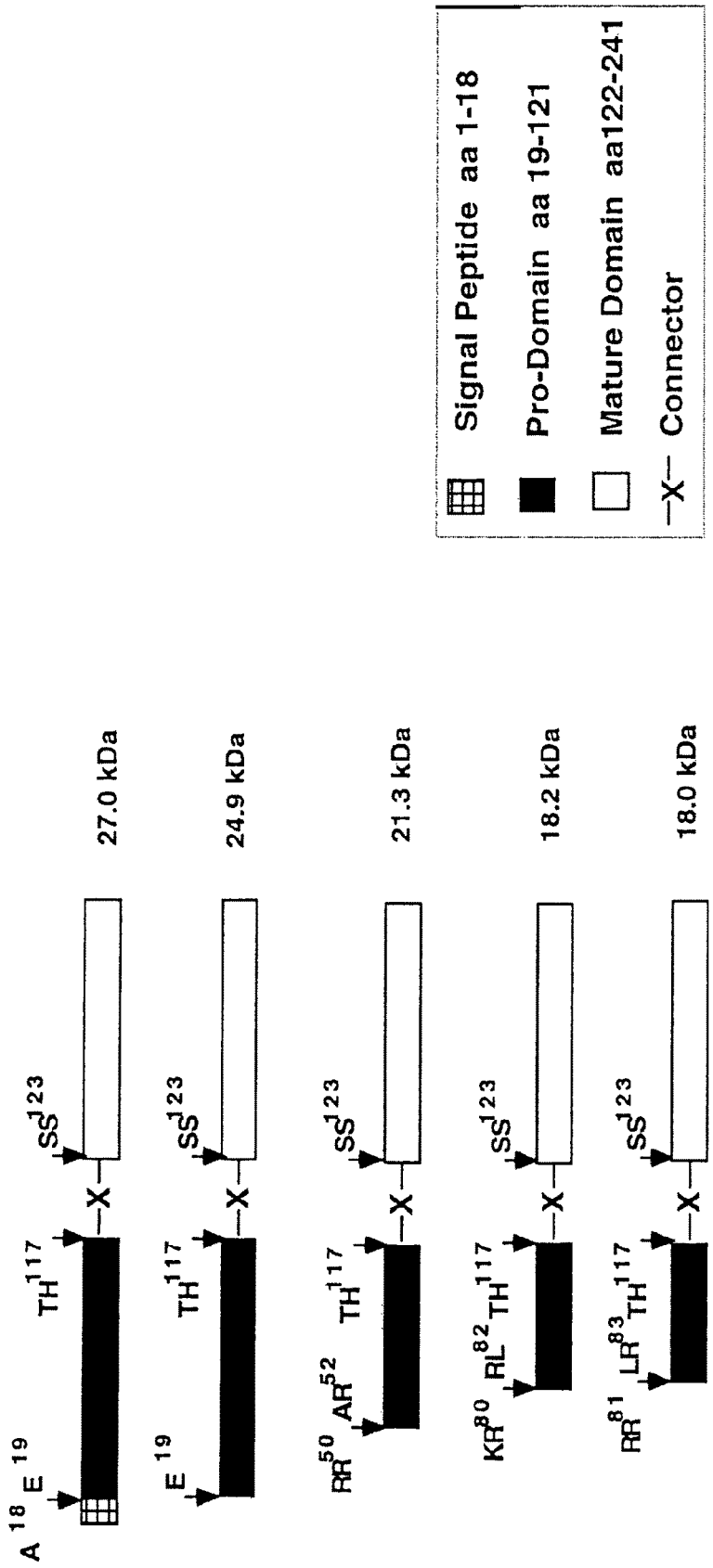

Figure 2A: Primary Protein Sequence from Human BDNF (Gen Bank Accession Number: AAA69805)

```
  1 mtilfltmvi syfgcmkaap mkeanirgqg glaypgvrth gtlesvngpk agsrgltsla
 61 dtfehvieel ldedqkvrpn eennkdadly tsrvmlssqv plepplfll eeyknyldaa
121 nmsmrvrrhs dparrgelsv cdsisewvta adkktavdms ggtvtvlekv pvskgqlkqy
181 fyetkcnpmg ytkegcrgid krhwnsgcrt tqsyvraltm dskkrigwrf iridtscvct
241 ltikrgr
```

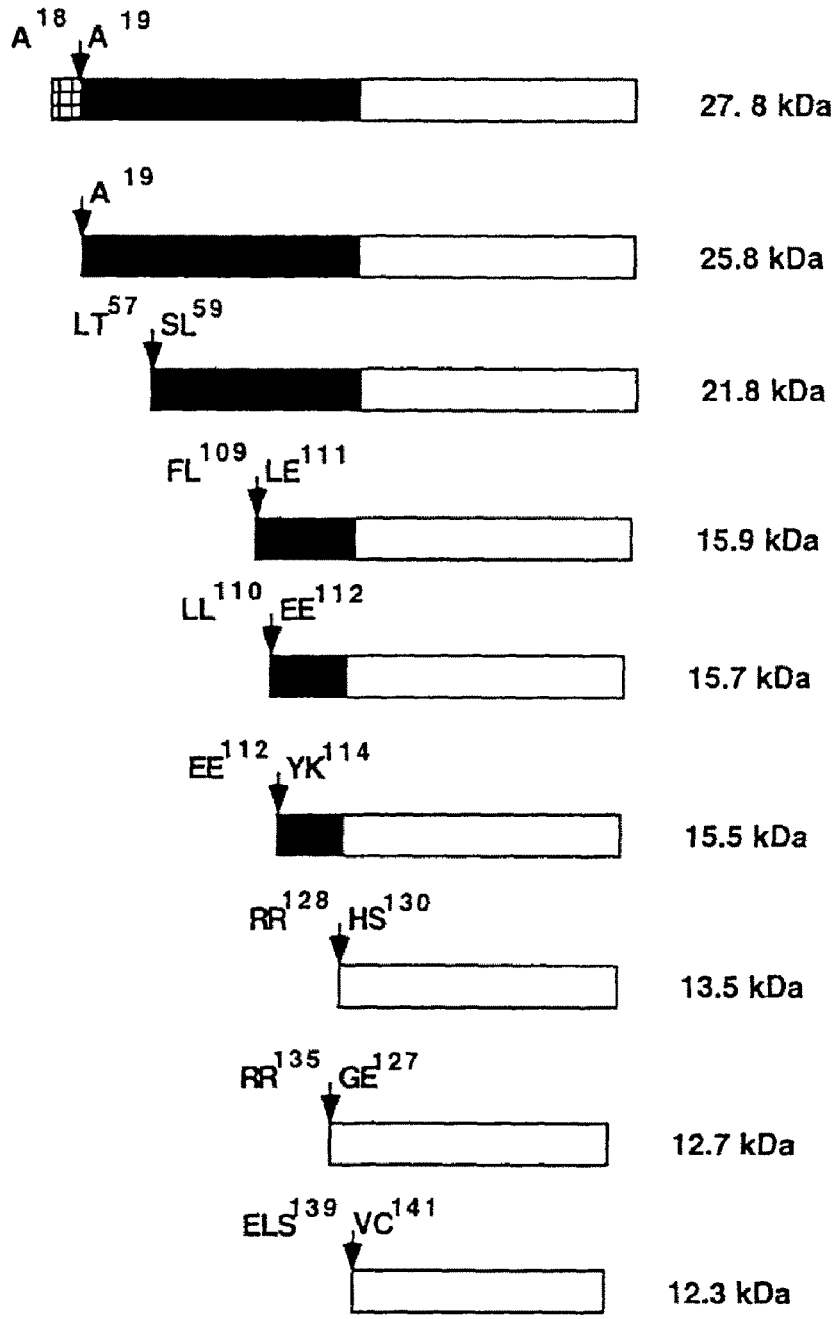
Figure 2B: Schematic Representation of Monomeric, Un-glycosylated BDNF Isoforms According to Prior Art

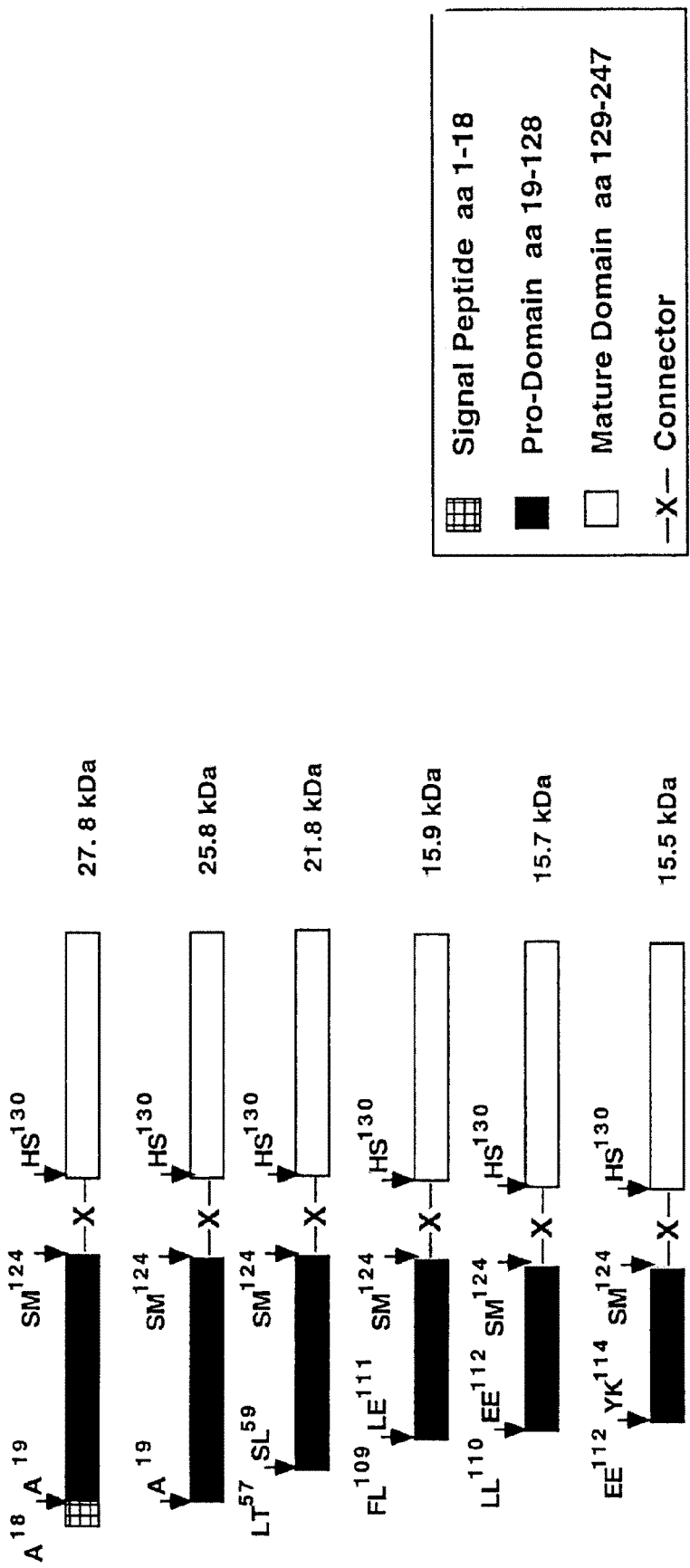
Figure 2C: Schematic Representation of Modified Pro-BDNF According to Invention Figure 3A: Primary Protein Sequence from Human NT-3 (Gen Bank Accession Number: AAA59953)

```
  1 msilfyvifl aylrgiqgnn mdqrslpeds insliikliq adilknklsk qmvdvkenyq
 61 stlpkaeapr eperggpaks afqpviamdt ellrgqrryn sprvlsdst plepplylm
121 edyvgspvva nrtsrrkrya ehkshrgeys vcdseslwvt dkssaidirg hqvtvlgeik
181 tgnspvkqyf yetrckearp vkngcrgidd khwnsqckts qtyvraltse nnklvgwrwi
241 ridtscvcal srkigrt
```

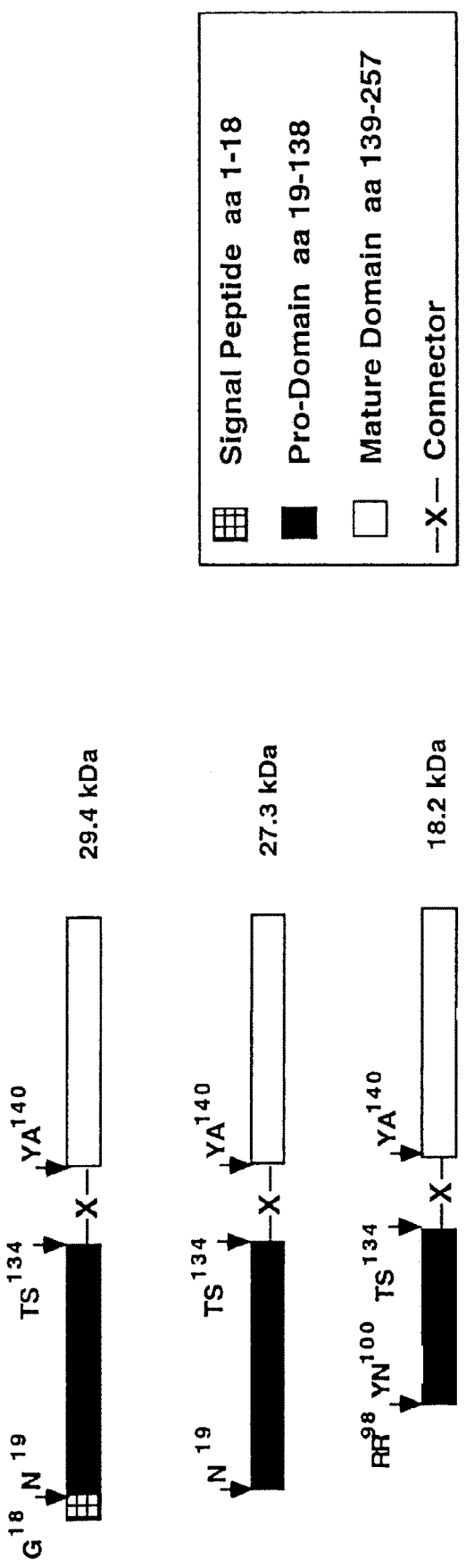
Figure 3C: Schematic Representation of Modified Pro-NT-3 According to Invention Figure 4A: Primary Protein Sequence from Human NT-4/5
(Gen Bank Accession Number: AAA60154 & AAA20549)

```
  1 mlplpscslp illflipsv piesqpppst lppflapewd llsprvvlsr gapagppllf
 61 lleagafres agapanrsrr gvsetapasr rgelavcdav sgwvtdrrta vdlrgrevev
121 lgevpaaggs plrqyffetr ckadnaeegg pgaggggcrg vdrrhwvsec kakqsyvral
181 tadaqgrvgw rwiridtacv ctllsrtgra
```

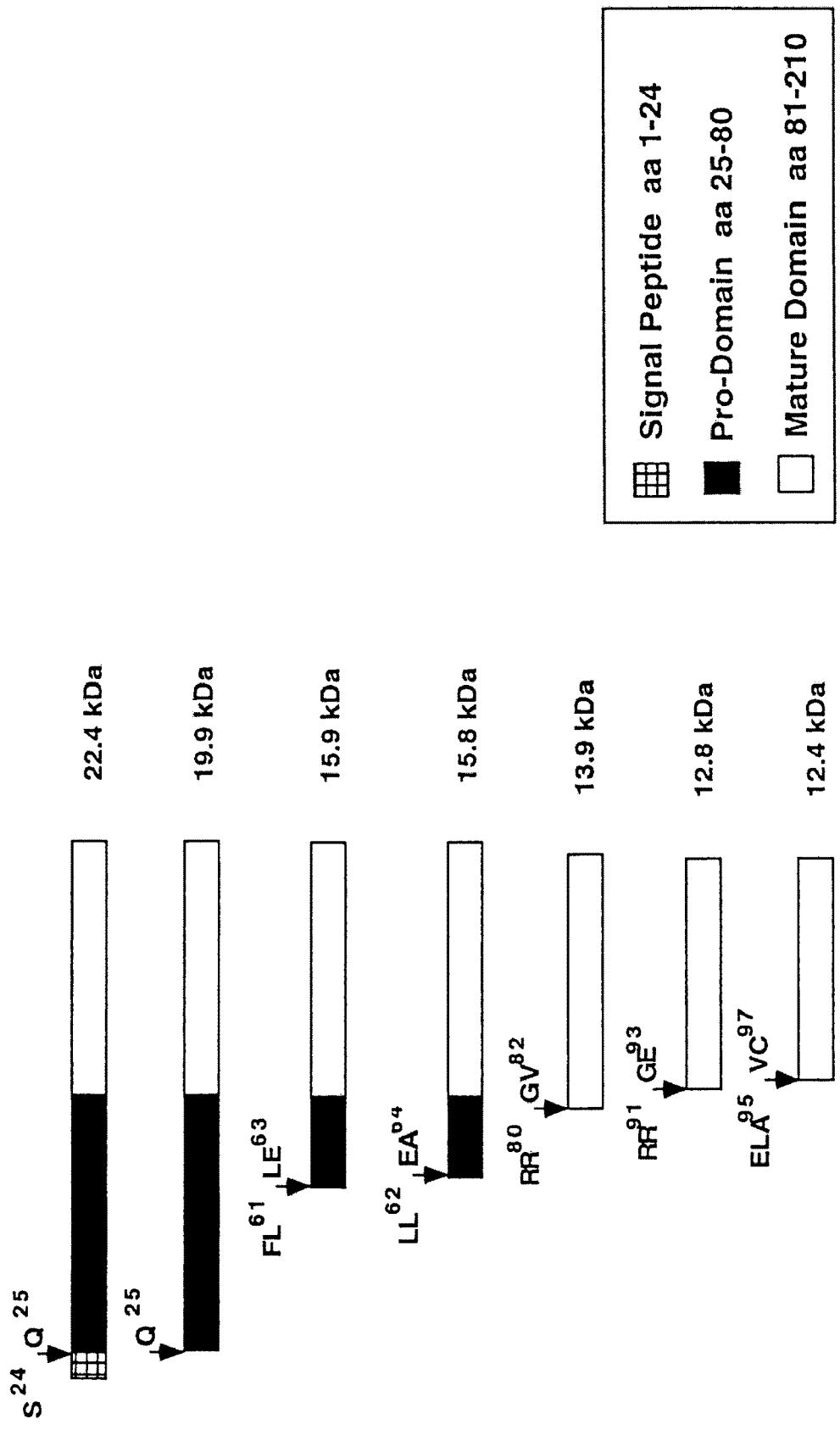
Figure 4B: Schematic Representation of Monomeric, Un-glycosylated NT-4/5 Isoforms According to Prior Art

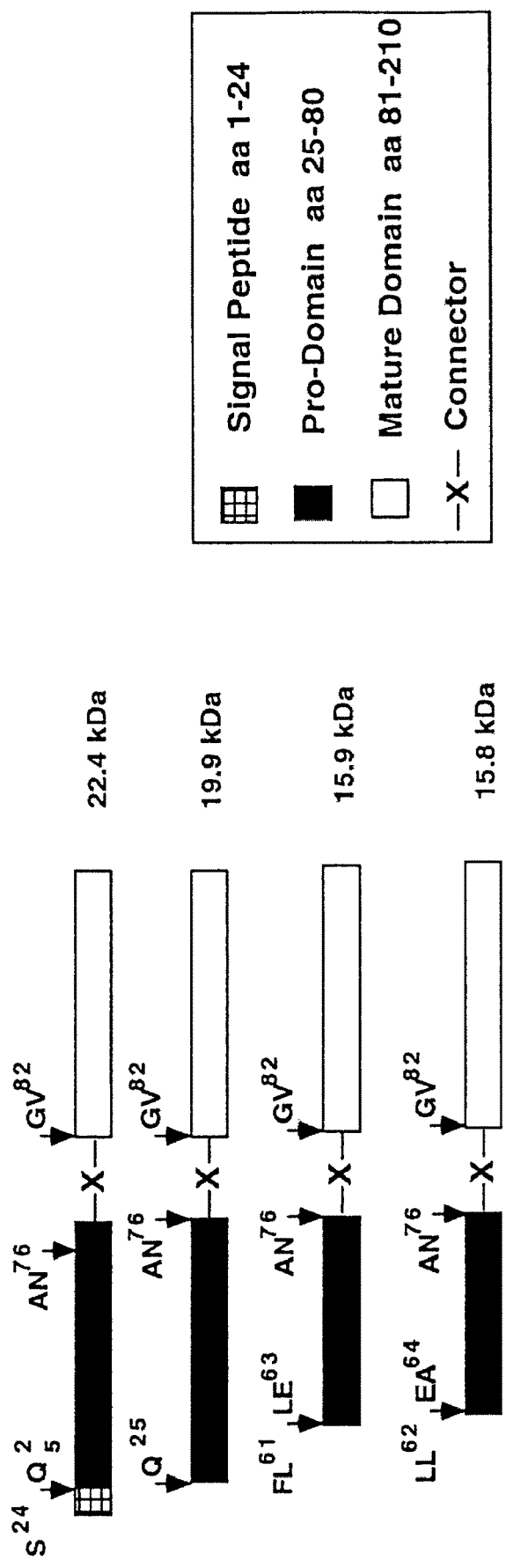
Figure 4C: Schematic Representation of Modified Pro-NT-4/5 According to Invention

Human p75 Receptor Sequence (Accession Number: g69056)

```
  1 mqagatgram dqprlllll lqvslgqake aoptglychs gecckacnlg egvaqpcgan
 61 qtvcepclds vtfsdvvsat epckpetecv glgmsapcv eadda vcrca ygyyqdetg
121 rceacrvcea gsglvfscqd kqntvceecp dgtysdeanh vdpclpctvc edterglrec
181 trwadaecee ipgrwitrst ppegsdstap stgepeappe gdliastvag vvttvmgssq
241 pvvrgttdnl ipvvcslla avvvglvayl afkrwnsckq nkggansrpv nqtpppegek
301 lhsdsgisvd sqslhdqqph tqtasgqalk gdgglyss1p pakreevek1 lngsagdtwr
361 hlagelgyqp ehidsfthea cpvraliasw atqdsatlda llaalrrigr adilveslcse
421 statspv
```

☐ Signal Sequence

▨ Extracellular Domain

▨ Transmembrane and Intracellular Domain

Figure 4D

Sequence Comparison for Human Neurotrophin Family Members

```
NGF   (AAA59931)    MSMLFYTLITAFLIGIQAEPHSESNVPAGHTIPQV---------------------
BDNF  (AAA69805)    MTILFLTMVISYFGCMKAAPMKEANIRGQGGLAYPGVRTHGTLE---------SV
NT-3  (AAA59953)    MSILFYVIFLAYLRGIQCNNMDQRSLPEDSLNSLIIKLIQADILKNKLSK
NT-4/5 (AAA60154)   ------------------------------------------------------

NGF   (AAA59931)    HWTKLQHSLDTALRRARSA--PAAAIAARVAGQTRNITVDPRLFKKRRLR
BDNF  (AAA69805)    NGPKAGSRGLTSLADTFEH---------VIEELLDEDQKVRPNEENNKDADLY
NT-3  (AAA59953)    QMVDVKENYQSTLPKAEAPREPERGGPAKSAFQPVIAMDTELLRQQRRYN
NT-4/5 (AAA60154)   -MLPLPSCSLPILLLFLLP-------SVPIESQPPPSTLPPFLAPEWDLL
                         *                                  ::

NGF   (AAA59931)    SBRVLFSTQPPREAADTQDLD---FBVGGAAPFNRTHRSKRSSSHPIFHR
BDNF  (AAA69805)    TSRVMLSSQVPLEPPLLFLLE---EYKNYLDAANMSMRVRRHSDPAR--R
NT-3  (AAA59953)    SPRVLLSDSTPLEPPPLYLME---DYVGSPVVANRTSRRKRYAEHKS-HR
NT-4/5 (AAA60154)   SPRVVLSRGAPAGPPLLFLLEAGAFRESAGAPANRSRRGVSETAPAS-RR
                    :.**::*    ..      ::       .    *:*    :      *

NGF   (AAA59931)    GEFSVCDSVSVWVG--DKTTATDIKGKEVMVLGEV-NINNSVFKQYFFET
BDNF  (AAA69805)    GELSVCDSISEWVTAADKKTAVDMSGGTVTVLEKV-PVSKGQLKQYFYET
NT-3  (AAA59953)    GEYSVCDSESLWVT--DKSSAIDIRGHQVTVLGEI-KTGNSPVKQYFYET
NT-4/5 (AAA60154)   GELAVCDAVSGWVT--DRRTAVDLRGREVEVLGEVPAAGGSPLRQYFFET
                    **:****:* **   *::* *:*   **  ::     . .:***:**

NGF   (AAA59931)    KCRDPNPVDSG------CRGIDSKHWNSYCTTTHTFVKALTMDG-KQAA
BDNF  (AAA69805)    KCNPMGYTKEG------CRGIDKRHWNSQCRTTQSYVRALTMDSKKRIG
NT-3  (AAA59953)    RCKEARPVKNG------CRGIDDKHWNSQCKTSQTYVRALTSENNKLVG
NT-4/5 (AAA60154)   RCKADNAEEGGPGAGGGCRGVDRRHWVSECKAKQSYVRALTADAQGRVG
                    :*.        .     ***:* :** *  *:,::;*:***  :

NGF   (AAA59931)    WRFIRIDTACVCVLSRKAVRRA
BDNF  (AAA69805)    WRFIRIDTSCVCTLTIKRGR-
NT-3  (AAA59953)    WRWIRIDTSCVCALSRKIGRT-
NT-4/5 (AAA60154)   WRWIRIDTACVCTLLSRTGRA-
                    **:*****:***.*   :  *
```

☐ Signal Sequence

▓ Pro-Neurotrophin Domain

░ Mature Neurotrophin Domain

\* Identical Amino Acid Sequence

: Conservative Amino Acid Substitution

. Significant Homology Across Members

Figure 5A

Sequence Comparison for NGF across Species

- Signal Sequence
- Pro-NGF Domain
- Mature NGF Domain
- * Identical Amino Acid Sequence
- : Conservative Amino Acid Substitution
- . Significant Homology Across Species

Sequence Comparison for BDNF across Species

```
Human  (AAA69805)    MTILFLTMVISYFGCMKAAPMKEANIRGQGGLAYPGVRTHGTLESVNGPK
Bovine (CAA66488)    --ILFLTMVISYFGCMKAAPMKEANLRAQGSLTYPGVRTHGTLESMNGPK
Rat    (AAA63483)    MTILFLTMVISYFGCMKAAPMKEANVHGQGNLAYPAVRTHGTLESVNGPR
Mouse  (CAAJ9159)    MTILFLTMVISYFGCMKAAPMKEVNVHGQGNLAYPGVRTHGTLESVNGPR
Chick  (AAC42220)    MTILFLTMVISYFSCMKAAPMKEASVRGHGSLAYPGRTHGTLESLIGEN
                     ***********.********..::..:*.*;**.:*******;.**.

Human  (AAA69805)    AGSRGL---TSLADTFEHVIEELLDEDQKVRPNEENNKDADLYTSRVMLS
Bovine (CAA66488)    VGSRGLTSSSSLADTFEHVIEELLDEDQKVRPSEENNKDADMYTSRVMLS
Rat    (AAA63483)    AGSRGLTT--TSLADTFEHVIEELLDEDQKVRPNEENHKDADLYTSRVMLS
Mouse  (CAAJ9159)    AGSRGLTT--TSLADTFEHVIEELLDEDQKVRPNEENHKDADLYTSRVMLS
Chick  (AAC42220)    AGSRGL---TSLADTFEHVIEELLDEDQDIQPSEEN-KDADLYTSRVMLS
                     .****  ;*****************...:*.*** ****.********

Human  (AAA69805)    SQVPLEPPLLFLLEEYKNYLDAANMSMRVRRHSDPARRGELSVCDSISEW
Bovine (CAA66488)    SQVPLEPPLLFLLEEYKNYLDAANMSMRVRRHSDPARRGELSVCDSISEW
Rat    (AAA63483)    SQVPEEPPLLFLLEEYKNYLDAANMSMRVRRHSDPARRGELSVCDSISEW
Mouse  (CAAJ9159)    SQVPLEPPLLFLLEEYKNYLDAANMSMRVRRHSDPARRGELSVCDSISEW
Chick  (AAC42220)    SQVPLEPPLLFLLEEYKNYLDAANMSMRVRRHSDPARRGELSVCDSTSEW
                     ****.*******************************************.***

Human  (AAA69805)    VTAADKKTAVDMSGGTVTVLEKVPVSKGQLKQYFYETKCNPMGYTKEGCR
Bovine (CAA66488)    VTAADKRLAVDMSGGTVTVLEKVPVSKGQLKQYFYETKCNPMGYTKEGCR
Rat    (AAA63483)    VTAADKKTAVDMSGGTVTVLEKVPVSKGQLKQYFYETKCNPMGYTKEGCR
Mouse  (CAAJ9159)    VTAADKKTAVDMSGGTVTVLEKVPVSKGQLKQYFYETKCNPMGYTKEGCR
Chick  (AAC42220)    VTAAEKKTAVDMSGATVTVLEKVPVPKGQLKQYFYETKCNPKGYTKEGCR
                     ****:*;*******.**************.****************.*******

Human  (AAA69805)    GIDKRHWNSQCRTTQSYVRALTMDSKKRIGWRFIRIDTSCVCTLTIKRGR
Bovine (CAA66488)    GIDKRHWNSQCRTTQSYVRALTMDSKKRIGWRFIRIDTSCVCTLTIKRGR
Rat    (AAA63483)    GIDKRHWNSQCRTTQSYVRALTMDSKKRIGWRFIRIDTSCVCTLTIKRGR
Mouse  (CAAJ9159)    GIDKRHWNSQCRTTQSYVRALTMDSKKRIGWRFIRIDTSCVCTLTIKRGR
Chick  (AAC42220)    GIDKRHWNSQCRTTQSYVRALTMDNKKRVGWRFIRIDTSCVCTLTIKRGR
                     ************************:***;*********************
```

☐ Signal Sequence

▨ Pro-BDNF Domain

▦ Mature BDNF Domain

* Identical Amino Acid Sequence
: Conservative Amino Acid Substitution
. Significant Homology Across Species

Figure 5C

Sequence Comparison for NT-3 across Species

```
Human   (AAA59953)   MSILFYVIFLAYLRGIQGNNMDQRSLPEDSLNSLIIKLIQADILKNKLSK
Rat     (AAA41727)   MSILFYVIFLAYLRGIQGNNMDQRSLPEDSLNSLIIKLIQADILKNKLSK
Mouse   (CAA37348)   MSILFYVIFLAYLRGIQGNSMDQRSLPEDSLNSLIIKLIQADILKNKLSK
Chick   (AAA68880)   MSILFYVIFLAYLRGIQSTNMDQRSLPEDSMNSLIIKLIRADILKNKLSK
Xenopus (AAB17723)   MSILFYVMFLPYLCGIHATNMDKRNLPENSMNSLPIKLIQADLLKNKISK
                     ******  ** ** *  *   *** * * * *  ** ** ** ******

Human   (AAA59953)   QMVDVKENYQSTLPKAEAPREPERGGPAKSAFQPVIAMDTELLRQQ--RR
Rat     (AAA41727)   QMVDVKENYQSTLPKAEAPREPEQGEATRSEFQPMIATDTELLRQQ--RR
Mouse   (CAA37348)   QMVDVKENYQSTLPKAEAPREPEQGEATRSEFQPMIATDTELLRQQ--RR
Chick   (AAA68880)   QVMDVKENYQNLVQKVEDHQEMDGDENVKSDFQPVISMDTDLLRQQ--RR
Xenopus (AAB17723)   QTVDTKENHQSTIPKPQIELDLDGDDNMKQDFQPVISLEAELVKQQKQRR
                      * *.***.*. . *   *    .   ** **.* *..*  .*.**

Human   (AAA59953)   YNSPRVLLSDSTPLEPPPLYLMEDYVGSPVVANRTS-RRKRYAEHKSHRG
Rat     (AAA41727)   YNSPRVLLSDSTPLEPPPLYLMEDYVGSPVVANRTSPRRKRYAEHKSHRG
Mouse   (CAA37348)   YNSPRVLLSDSTPLEPPPLYLMEDYVGNPVVANRTSPRRKRYAEHKSHRG
Chick   (AAA68880)   YNSPRVLLSDNTPLEPPPLYLTBDYVGSSVVLNRTS-RRKRYAEHKSHRG
Xenopus (AAB17723)   YKSPRVLLSDSLPLEPPPLYLMDDYIGHSTVVNNRTSRRKRFAEHKGHRG
                    * ********. *********  **.* . .* .* **** *** ***

Human   (AAA59953)   EYSVCDSESLWVTDKSSAIDIRGHQVTVLGEIKTGNSPVKQYFYETRCKE
Rat     (AAA41727)   EYSVCDSESLWVTDKSSAIDIRGHQVTVLGEIKTGNSPVKQYFYETRCKE
Mouse   (CAA37348)   EYSVCDSESLWVTDKSSAIDIRGHQVTVLGEIKTGNSPVKQYFYETRCKE
Chick   (AAA68880)   EYSVCDSESLWVTDKSSAIDIRGHQVTVLGEIKTGNSPVKQYFYETRCKE
Xenopus (AAB17723)   EYSVCDSESLWVTDKMNAIDIRGHQVTVLGEIKTGNSPVKQYFYETRCKE
                    ***************  ********************************

Human   (AAA59953)   ARPVKNGCRGIDDKHWNSQCKTSQTYVRALTSENNKLVGWRWIRIDTSCV
Rat     (AAA41727)   ARPVKNGCRGIDDKHWNSQCKTSQTYVRALTSENNKLVGWRWIRIDTSCV
Mouse   (CAA37348)   ARPVKNGCRGIDDKHWNSQCKTSQTYVRALTSENNKLVGWRWIRIDTSCV
Chick   (AAA68880)   AKPVKNGCRGIDDKHWNSQCKTSQTYVRALTSENNKLVGWRWIRIDTSCV
Xenopus (AAB17723)   ARPVKNGCRGIDDKHWNSQCKTSQTYVRALTSENNKMVGWRWIRIDTSCV
                    * ********************************** ************

Human   (AAA59953)   CALSRKIGRT
Rat     (AAA41727)   CALSRKIGRT
Mouse   (CAA37348)   CALSRKIGRT
Chick   (AAA68880)   CALSRKIGRT
Xenopus (AAB17723)   CALSRKIGRS
                    *********.
```

☐ Signal Sequence

▓ Pro-NT-3 Domain

░ Mature NT-3 Domain

\* Identical Amino Acid Sequence

: Conservative Amino Acid Substitution

. Significant Homology Across Species

Figure 5D

Sequence Comparison for NT-4/5 across Species

```
Human   (AAA60154)  ------------------MLPLPSCSLPILLLFLLLPSVPIESQPPP------
Rat     (AAA41728)  ------------------MLPRHSCSL-LLFLLLLPSVPMEPQPPS------
Xenopus (CAA82906)  MLRLYRMVISYCCAICAAPFQSRTTDLDYGPDKTSEASDQSVRNNFSH
                                           *    *    *   :

Human   (AAA60154)  ----STLPPFLAPEWDLLSPRVLSRGAPAGPPLLFLEEAGAF
Rat     (AAA41728)  ----STLPPFLAPEWDLLSPRVALSRGTPAGPPLLFLIEAGAY
Xenopus (CAA82906)  VLQNGFFPDLSSTYSSMAGKDWNLVSPRVTLLSSEEPSGPLLFLSEETVV
                        . :** .:::   :  :::**. **:* .:** *     ::

Human   (AAA60154)  R-ESAGAPANRSRRGVSETAPASRRGELAVCDAVSGWVTDRRTAVDLRGR
Rat     (AAA41728)  G-EPAGAPANRSRRGVSETAPASRRGELAVCDAVSGWVTDRRTAVDLRGR
Xenopus (CAA82906)  HPEPANKTSRLKRASGSDSVSLSRRGELSVCDSVNVWVTDKRTAVDDRGK
                        *. : * :::. *:  ********:***:*. ****:**** **:

Human   (AAA60154)  EVEVLGEVPAAGGSPLRQYFFETRCKADNAEEGGPGAGGGCRGVDRRHW
Rat     (AAA41728)  EVEVLGEVPAAGGSPLRQYFFETRCKAESAGEGGPGVGGGCRGVDRRHW
Xenopus (CAA82906)  IVTVMSEIQTLIG-PLKQYFFETKCNPS-----GSTTRGCRGVDKKQW
                    * :: .*:  : * **:********:*:..       * : *****::*

Human   (AAA60154)  VSECKAKQSYVRALTADAQGRVGWRWIRIDTACVCTLLSRTGRA
Rat     (AAA41728)  LSECKAKQSYVRALTADSQGRVGWRWIRIDTACVCTLLSRTGRA
Xenopus (CAA82906)  ISECKAKQSYVRALTIDANKLVGWRWIRIDTACVCTLLSRTGRT
                    :*************** *: : ********************:
```

☐ Signal Sequence

▓ Pro-NT-4/5 Domain

▒ Mature NT-4/5 Domain

\*   Identical Amino Acid Sequence

:   Conservative Amino Acid Substitution

.   Significant Homology Across Species

Figure 5E

M = mature
Pro = cleavage resistant pro-NGF

Figure 8
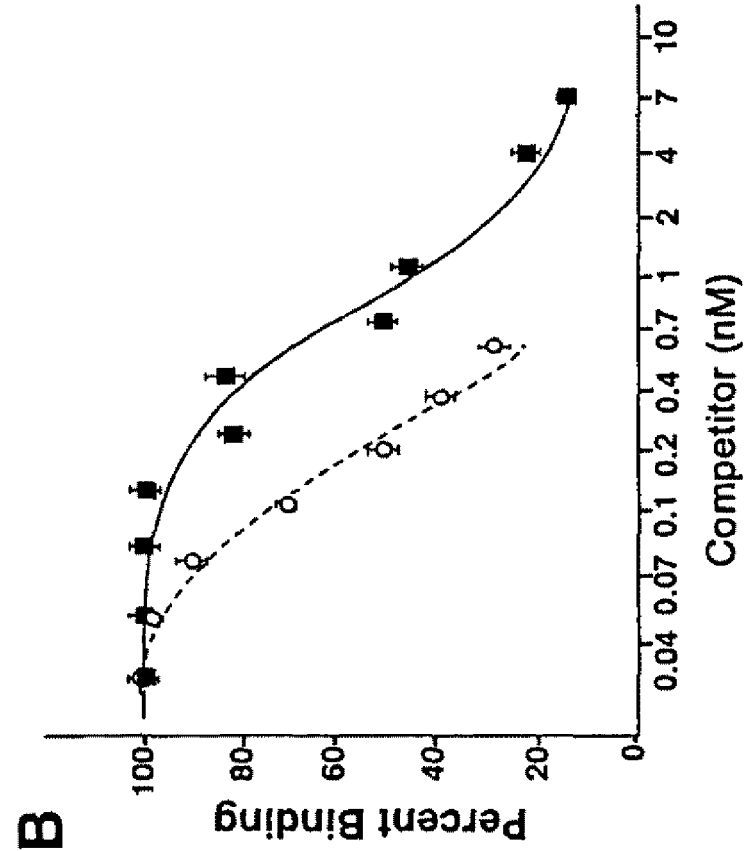
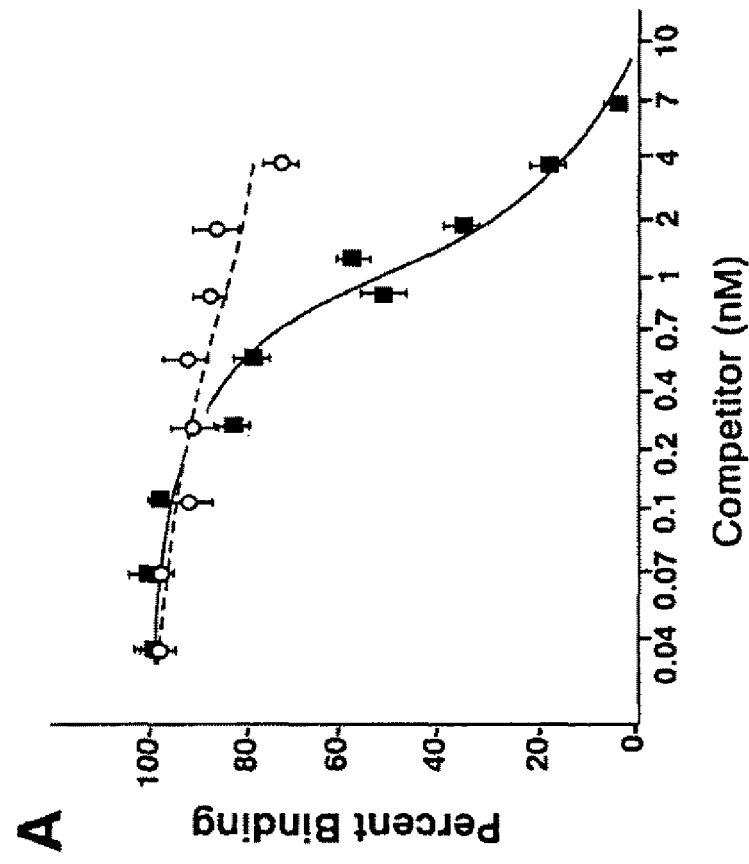

Figure 9
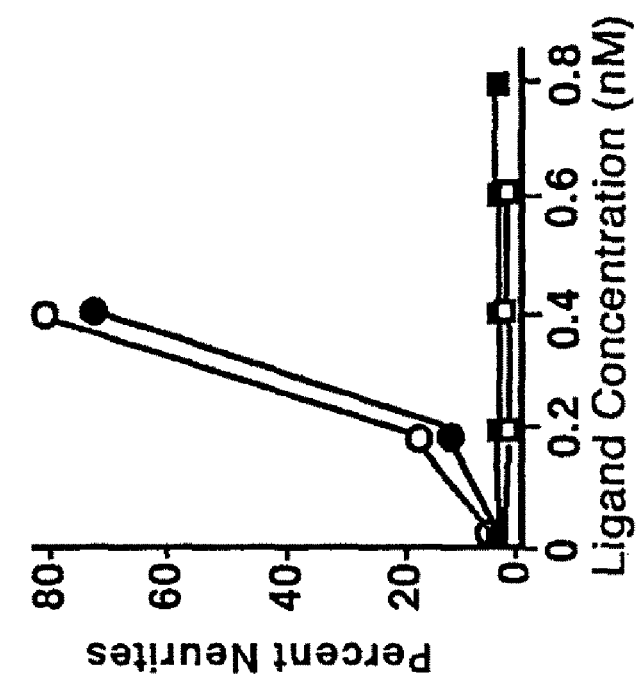
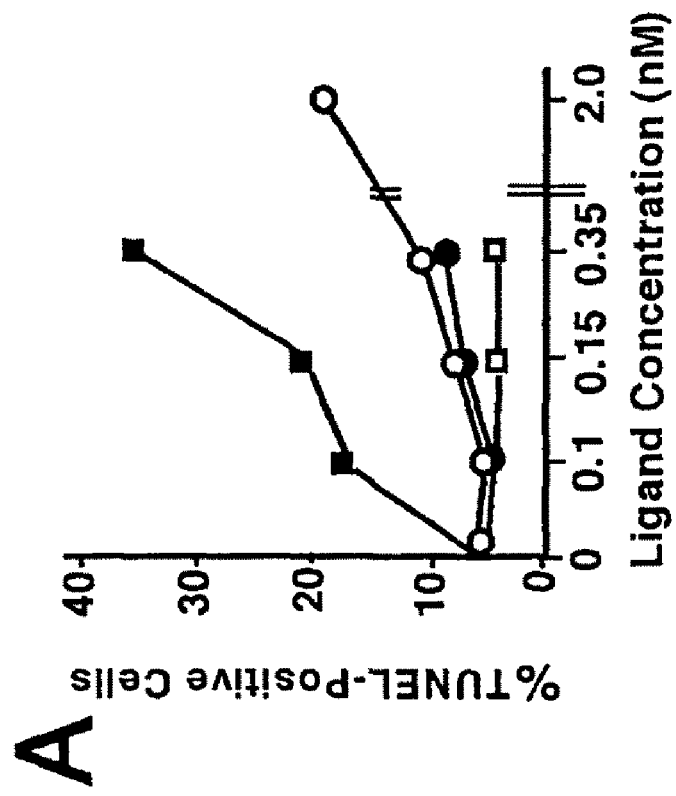

METHOD FOR INHIBITING APOPTOSIS THROUGH THE P75 NEUROTROPHIN RECEPTOR

This application asserts the priority of U.S. provisional application Ser. No. 60/293,823 filed May 25, 2001 and U.S. provisional application Ser. No. 60/305,510 filed Jul. 13, 2001, and is a continuation application of application Ser. No. 10/155,886 filed on May 24, 2002, now U.S. Pat. No. 7,507,799 the specifications of which are incorporated by reference in their entirety.

The invention described in this application was made with funds from the National Institutes of Health; Grant Number R01 NS 30687. The United States government has certain rights in the invention.

BACKGROUND OF THE INVENTION

The neurotrophins, including nerve growth factor (NGF), brain derived neutrophic factor (BDNF), neurotrophin 3 (NT-3), and neurotrophin 4/5 (NT-4/5), are among the molecular determinants that regulate the generation of diverse neuronal populations and the maintenance of their functions within the nervous system (Lewin G R, et al. 1996. *Ann. Rev. Neurosci.* 19:289; Theonen H. 1995. *Science* 70:593). The binding of mature neurotrophins to their cognate receptor tyrosine kinase, trks, (i.e., NGF to trk A, BDNF and NT-4/5 to trk B, and NT-3 to trk C) triggers a cascade of anti-apoptotic events that ensure neuronal survival. In competition analysis, the mature form of NGF is more potent than the larger pro-forms of NGF in trk A binding (Chen Y E, et al. 1997. *Mol. Cell. Endocrinol.* 127:129) and in promoting cell survival.

In addition to trks, all mature neurotrophins are thought to interact with the p75 receptor. The p75 receptor belongs to the tumor necrosis factor (TNF) receptor superfamily. The extracellular domain of p75 that is the most critical for neurotrophin binding is reported to be the third and fourth cysteine loops (Choi D W. 1990. *J. Neurosci.* 10:2493; Yan H, et al. 1991. J. Biol. Chem. 266:12099).

The mechanism of signaling elicited by activated trks is unequivocal. However, the molecular and biological consequences of mature neurotrophin-p75 interaction have been confounding.

For example, structural analysis indicates that multiple regions of the extracellular domain of the p75 receptor contribute to mature NGF binding. Point mutagenesis suggests that the variable loops of mature neurotrophins are most important for interaction with p75 (Ryden M, et al. 1995. *Embo J.* 14:1979). Despite their importance for binding, these variable loops exhibit the highest degree of variation between the different mature neurotrophins. Nevertheless, all mature neurotrophins bind to p75.

Similarly, kinetic analysis of mature NGF-p75 binding demonstrates that mature NGF binds very rapidly, and dissociates very rapidly (Mahadeo D L, et al. 1994. *J. Biol. Chem.* 269:6884; Tait J F, et al. 1981. *J. Biol. Chem.* 256:11086). These results are perplexing, since most ligand-receptor interactions exhibit slow dissociation rates. In contrast, mature NGF binds to trk A slowly and is released very slowly.

When both types of receptors are present in the same cell, p75 is reported to enhance the affinity of trk A towards mature NGF (Mahadeo D L, et al., 1994. *J. Biol. Chem.* 269:6884; Hempstead, B. L., et al. 1991. Nature 350:678-683). In the absence of trk, however, binding of mature neurotrophin to p75 is reported to induce apoptosis (Chao M V, et al., 2001. *Curr. Opin. Neurobiol.* 11:281-286.). In addition, apoptosis is believed to be induced in neuronal cells via p75 when mismatching of mature neurotrophin-trk pairing occurs (Majdan M. 1999. *Int J. Dev. Neurosci.* 17:153).

For example, superior cervical ganglionic neurons express trk A and p75, but not trk B. As mentioned above, it is known that mature BDNF binds to trk B and to p75, but not to trk A. As a result of the mismatching of mature neurotrophin-trk pairing, treatment of superior cervical ganglionic neurons with mature BDNF triggers p75-mediated apoptosis (Bamji S X, et al. 1998. *J. Cell. Biol.* 140:911). Therefore, apoptosis is believed to be induced in neuronal cells when p75 is expressed alone. In addition, when both p75 and trk are present in the same cells, apoptosis is induced during mismatching of mature neurotrophin-trk pairing or when trk mediated signaling is inhibited.

Accordingly, currently available data have refined the original neurotrophin hypothesis. The original hypothesis stated that the lack of trophic support leads to selective neuronal loss (Korsching S. 1993. *J. Neurosci.* 13:2739). The refined model states that inappropriate activation of p75 by mature neurotrophins will lead to apoptosis.

If the refined model proves to be correct, the clinical implications are very significant. The p75 receptor is up-regulated in neuronal populations after nervous system stress or injury (Roux P P, et al., 1999. *J. Neurosci.* 19:6887; Widenfalk J, et al. 2001. *J. Neurosci.* 21:3457; van Eden C G, et al. 1994. *Brain Res. Dev. Brain Res.* 82:167) and in glia cells of multiple sclerosis patients (Dowling P, et al. 1999. *Neurology* 53:1676; Chang A, et al. 2000. *J. Neurosci.* 20:6404). Therefore, under the refined model, activation of p75 by mature neurotrophins in these cells will lead to apoptosis.

Recent findings have implicated apoptosis as a common endpoint of various nervous system injuries and environmental insults. Dying neurons in selected instances of, for example, hypoxic ischemia (Choi D W. 1990. *J. Neurosci.* 10:2493), viral infection (Lin K I, et al. 1996. *J. Cell Biol.* 131:1149), and neurodegenerative disorders (Roy N, et al. 1995. Cell 80:167; Liston P, et al. 1996. *Nature* 379:349) display a number of hallmark characteristics of apoptotic cells.

There is increasing evidence that mature neurotrophins and their receptors (p75 and trks) can also modulate a variety of cellular events in non-neuronal tissues (Lomen-Hoerth C, et al. 1995. *J. Neurochem.* 64:1780). In some instances, p75 expression is distinct from that of the trks (Wheeler E F, et al. 1998. *J Comp Neurol.* 4:407). The distinct expression supports a trk-independent mechanism for p75 function in non-neuronal cells.

For example, NGF and p75 immunoreactivites have been detected in developing incisors (Mitsiadis T A, et al. 1993. *Differentiation* 54:161). In human adults, upregulation of p75 in renal biopsies is correlated with various glomerulopathies. The increased expression of p75 detected in renal biopsies apparently recapitulates a normal developing state during kidney development. Both p75 and NGF have been detected in developing muscles. In vitro analysis of the muscle cell line C2C12 suggests that p75-mediated myogenic differentiation is inhibited by NGF. The inhibition of myogenic differention by the NGF-p75 interaction occurs in a trk-independent manner. The expression of p75 is also detected in the atherosclerotic plaques of smooth muscle cells, as well as in many carcinoma cell types.

In addition, the expression of p75 has been observed in hair follicles (Yardley G, et al. 2000. *Exp. Dermatol.* 9:283; Botchkarev V A, et al. 2000. *FASEB J.* 14:1931). Both p75 and trks are found in hair follicles in the anagen (active growth) phase of hair growth (Botchkarev V A, et al. 2000.

FESEB J. 14:1931). However, during the catagen (regression) phase, there is a disappearance of trk A, trk B, and trk C. The expression of p75 alone is markedly upregulated and detected in cells undergoing apoptosis (Botchkarev V A, et al. 2000. FESEB J. 14:1931). These findings suggest that p75 is involved in both the survival and apoptosis of cells in the hair follicle.

The interaction of p75 and neurotrophins in both neuronal and non-neuronal cells play a very important role in normal tissue development, as well as in many disease states. Currently available data suggest that p75 promotes both cell survival and apoptosis. However, conflicting and perplexing data in the prior art, such as the data described above, would have precluded the consideration of modulating mature neurotrophin-p75 interaction as a practical means for treating particular disorders.

Unwanted cell growth is a problem in various hyperproliferative conditions, such as cancer, acne, shingles, etc. Unwanted cell death is a problem in other conditions, such as injuries due to trauma, hair loss, etc. Thus, there is an immediate need for modulating apoptosis.

In certain instances, it is desirable to promote the p75-mediated apoptosis of deleterious cells. In other instances, it is desirable to inhibit the p75-mediated apoptosis (for example, in dying neurons and in dying hair follicles) without affecting the survival promoting functions of mature neurotrophins.

SUMMARY OF THE INVENTION

In one embodiment, the invention relates to an isolated protein comprising a pro-domain of a proneurotrophin, the pro-domain comprising a pro-domain conserved region, the conserved region being an amino acid sequence having at least approximately 85% identity to amino acid residues approximately at positions 79-98 of human NGF (SEQ. ID. NO: 73); 91-105 of human BDNF (SEQ. ID. NO: 74); 101-115 of human NT-3 (SEQ. ID. NO: 75), or 43-57 of human NT-4/5 (SEQ. ID. NO: 76).

In another embodiment, the invention relates to a pharmaceutical composition that comprises a protein and a pharmaceutically acceptable additive, the protein comprising: a pro-domain of a proneurotrophin, the pro-domain comprising a pro-domain conserved region, the conserved region being an amino acid sequence having at least approximately 85% identity to amino acid residues approximately at positions 84-98 of human NGF (SEQ. ID. NO: 114); 91-105 of human BDNF (SEQ. ID. NO: 74); 101-115 of human NT-3 (SEQ. ID. NO: 75), or 43-57 of human NT-4/5 (SEQ. ID. NO: 76).

In another embodiment, the invention relates to an isolated protein comprising: (i) a pro-domain of a proneurotrophin, the pro-domain comprising a pro-domain conserved region; (ii) a mature neurotrophin domain; and (iii) a connector that joins the pro-domain conserved region to the mature neurotrophin domain and that is resistant to protease cleavage.

In another embodiment, the invention relates to a pharmaceutical composition that comprises a protein and a pharmaceutically acceptable additive, the protein comprising: (i) a pro-domain conserved region; (ii) a mature neurotrophin domain; and (iii) a connector that joins the pro-domain conserved region to the mature neurotrophin domain and that is resistant to protease cleavage.

In another embodiment, the invention relates to a nucleic acid molecule that encodes a protein described above.

In another embodiment, the invention relates to a method for producing a protein described above, the method comprising expressing a nucleic acid molecule that encodes the protein in a host cell.

In another embodiment, the invention relates to a vector comprising a nucleic acid molecule described above.

In another embodiment, the invention relates to a host cell comprising a nucleic acid molecule described above.

In another embodiment, the invention relates to a method for inducing apoptosis in a cell that comprises p75 receptors on its surface, the method comprising causing the p75 receptor to bind a pharmaceutical composition described above.

In another embodiment, the invention relates to a method for cleaving a proneurotrophin protein to a mature neurotrophin, the method comprising contacting the proneurotrophin protein with MMP 3, MMP 7, or plasmin.

In another embodiment, the invention relates to a method for inhibiting the cleavage of a proneurotrophin to a mature neurotrophin in a mammal in need thereof, the method comprising administering to the mammal an inhibitor of a protease that cleaves the major cleavage site found in native proneurotrophin proteins.

In another embodiment, the invention relates to a method for preventing or treating atherosclerosis in a mammal, the method comprising administering to the mammal an inhibitor of a protease that cleaves the major cleavage site found in native proneurotrophin proteins.

In another embodiment, the invention relates to a method for inducing cell apoptosis in a mammal in need thereof, wherein the cell is susceptible to apoptosis initiated by the binding of a proneurotrophin to a p75 receptor, the method comprising treating the mammal with an inhibitor of a protease that cleaves the major cleavage site found in native proneurotrophin proteins.

In another embodiment, the invention relates to a method for inducing apoptosis of cells expressing p75 receptors and trk receptors in a mammal in need thereof, the method comprising administering to the mammal an effective amount of a cleavage-resistant proneurotrophin and an inhibitor of trk activation.

In another embodiment, the invention relates to a method for inhibiting apoptosis of a cell in a mammal in need thereof, the method comprising administering to the mammal an effective amount of a molecule that inhibits the binding of a proneurotrophin to a p75 receptor.

In another embodiment, the invention relates to a method to screen a human patient for a condition associated with undesired apoptosis, the method comprising determining whether the level of at least one proneurotrophin, or of a conjugate between a p75 receptor and at least one proneurotrophin, in a biological sample of the patient is elevated (i.e. higher than normally occurs in the absence of the condition), wherein elevated levels of proneurotrophins or p75/proneurotrophin conjugates indicate the existence of the condition.

In another embodiment, the invention relates to a method for inhibiting apoptosis-mediated hair follicle regression in a mammal in need thereof, the method comprising administering to the mammal an effective amount of a molecule that inhibits the binding of a proneurotrophin to a p75 receptor.

BRIEF DESCRIPTION OF THE FIGURES

FIG. 1A: Primary Protein Sequence from Human NGF (GenBank Accession Number: AAA59931) (SEQ. ID. NO: 1);

FIG. 1B: Schematic Representation of Monomeric, Unglycosylated Human NGF Isoforms According to Prior Art;

FIG. 1C: Schematic Representation of Modified Human Pro-NGF According to Invention;

FIG. 2A: Primary Protein Sequence from Human BDNF (GenBank Accession Number: AAA69805) (SEQ. ID. NO: 2);

FIG. 2B: Schematic Representation of Monomeric, Unglycosylated Human BDNF Isoforms According to Prior Art;

FIG. 2C: Schematic Representation of Modified Human Pro-BDNF According to Invention;

FIG. 3A: Primary Protein Sequence from Human NT-3 (GenBank Accession Number: AAA59953) (SEQ. ID. NO: 3);

FIG. 3B: Schematic Representation of Monomeric, Unglycosylated Human NT-3 Isoforms According to Prior Art;

FIG. 3C: Schematic Representation of Modified Human Pro-NT-3 According to Invention.

FIG. 4A: Primary Protein Sequence from Human NT-4/5 (GenBank Accession Numbers: AAA60154 & AAA20549) (SEQ. ID. NO: 4);

FIG. 4B: Schematic Representation of Monomeric, Unglycosylated Human NT-4/5 Isoforms According to Prior Art.

FIG. 4C: Schematic Representation of Modified Human Pro-NT-4/5 According to Invention.

FIG. 4D shows the Human p75 Receptor Sequence (Accession Number: g69056) (SEQ. ID. NO: 5);

FIG. 5A: Alignment results for the human proneurotrophins. The amino acid sequences of human NGF (SEQ. ID. NO: 1), BDNF (SEQ. ID. NO: 2), NT-3 (SEQ. ID. NO: 3) and NT-4/5 (SEQ. ID. NO: 4) are aligned for best fit. The signal sequences are boxed (shown as the N-terminal 19-24 amino acids). Conserved positions are shown: * indicates an amino acid conserved in all neutrotrophinis; single and double dots show positions with partial conservation. The mature sequences are the longer boxed sequences.

FIG. 5C: Sequence Comparison for BDNF across Species. Human (SEQ. ID. NO: 2); Bovine (SEQ. ID. NO: 13); Rat (SEQ. ID. NO: 14); Mouse (SEQ. ID. NO: 15); Chicken (SEQ. ID. NO: 16).

FIG. 5D: Sequence Comparison for NT-3 across Species. Human (SEQ. ID. NO: 3); Rat (SEQ. ID. NO: 17); Mouse (SEQ. ID. NO: 18); Chicken (SEQ. ID. NO: 19); Xenopus (SEQ. ID. NO: 20).

FIG. 5E: Sequence Comparison for NT-4/5 across Species. Human (SEQ. ID. NO: 4); Rat (SEQ. ID. NO: 21); Xenopus (SEQ. ID. NO: 22).

FIG. 8: Binding analysis of mature and cleavage-resistant pro-NGF to TrkA or $p75^{NTR}$ receptors. Cleavage resistant pro-NGF or commercial mature NGF were assayed for their ability to displace $^{125}$I-radiolabeled commercial mature NGF (1 nM) from 293 cells expressing TrkA (A) or A875 cells expressing $p75^{NTR}$ (B). Competition analysis of equilibrium binding was performed using a whole-cell assay. Cells were incubated with 1 nM radioiodinated NGF in the presence or absence of unlabeled mature NGF or unlabeled proNGF from 0.005 to 7 nM concentration for 1 hour at 0.4° C. Nonspecific binding measured in parallel incubation with 500-fold excess mature NGF was less than 10% of total binding; all results were corrected for this non-specific binding. Each point represents the mean±standard deviation of quadruplicate determinations. Squares, commercial mature NGF; open circles, cleavage resistant pro-NGF. Competition with purified mature NGF yielded results that were comparable to those obtained with commercial NGF.

DETAILED DESCRIPTION OF THE INVENTION

Figure 5B:
FIG. 5B: Sequence Comparison for NGF across Species. Human (SEQ. ID. NO: 6); Gorilla (SEQ. ID. NO: 7); Rat (SEQ. ID. NO: 8); Mouse (SEQ. ID. NO: 9); Bovine (SEQ. ID. NO: 10); Chicken (SEQ. ID. NO: 11); Xenopus (SEQ. ID. NO: 12).

The present invention is based on the surprising discovery by the inventors that uncleaved proneurotrophins bind with higher affinity to p75 than do the cleaved, mature neurotrophins. Moreover, the inventors have discovered that uncleaved proneurotrophins are more effective than mature neurotrophins in inducing apoptosis of cells that express p75, especially cells that express large numbers of p75, or that express p75 exclusively, relative to trk receptors.

In this specification, the p75 receptor is the member of the TNF receptor superfamily that binds all neurotrophins. The p75 receptor has sometimes been called the low affinity neurotrophin receptor.

While the present invention is not limited by any particular mechanism or theory, these results, taken together, resolve the question of biological activity of the proneurotrophins. The inventors have discovered that proneurotrophins induce apoptosis of cells via interaction of the proneurotrophins with the p75 receptor. Therefore, it is now, for the first time, apparent that regulated cleavage of proneurotrophins alters their biological activity from promoting death of neuronal cells to promoting survival, and that the proneurotrophins are an integral part of the system.

Proteins:

As will be discussed in more detail below, one embodiment of the present invention relates to cleavage resistant proteins comprising modifications of native proneurotrophins. Cleavage of such native proneurotrophins generate the family of mature neurotrophins. Proteins comprising modifications of native proneurotrophins in accordance with the invention will be referred to herein as modified or cleavage-resistant proneurotrophins.

The native, mature neurotrophin family is well defined, and the members share a number of physical and biological characteristics. For example, biologically active mature neurotrophins are all cleaved from a precursor proneurotrophin at a consensus cleavage site of the furin type (R-X-R/K-R). This cleavage site will be referred to as the major proneurotrophin cleavage site (or, simply, the major cleavage site). As can be seen from FIGS. 1A-4A, the major human proneurotrophin cleavage site includes R-S-K-R (SEQ. ID. NO: 23) in NGF, R-V-R-R (SEQ. ID. NO: 24) in BDNF, R-R-K-R (SEQ. ID. NO: 25) in NT-3, and RSRR (SEQ. ID. NO: 26) in NT-4/5.

The mature members of the family interact with the p75 receptor and with the family of trk receptors. All of the mature neurotrophins are involved in the development, survival, and function of neurons in both the peripheral and central nervous systems. The molecular masses of monomeric, unglycosylated mature neurotrophins range from approximately 13.4 to approximately 14 kDa. The isoelectric points of the mature neurotrophins range from approximately 9 to approximately 10.

Structurally, six cysteine residues conserved in the mature neurotrophins give rise to three intra-chain disulfide bonds. The neurotrophins exist in solution as non-covalently associated dimers.

Members of the mature family of neurotrophins include nerve growth factor, (NGF), brain derived neurotrophic factor (BDNF), neurotrophin 3 (NT-3), and neurotrophin 4/5 (NT-4/5 or NT-4). The molecular masses of monomeric, unglycosylated mature NGF, BDNF, NT-3, and NT-4/5 are approximately 13.5, 13.5, 13.6, and 13.9 kDa, respectively.

The precursors of the mature neurotrophins, i.e. the native proneurotrophins, are also members of a well defined family. For example, the molecular masses of monomeric, unglycosylated proneurotrophins, including the N-terminal signal sequence, range from approximately 22 to approximately 30 kDa. The isoelectric points of the proneurotrophins range from approximately 8 to approximately 9. Most characteristically, the proneurotrophins are cleaved by proteases at or near the major proneurotrophin cleavage site to produce a mature neurotrophin.

Members of the proneurotrophins include pro-NGF, pro-BDNF, pro-NT-3, and pro-NT-4/5. The molecular masses of monomeric, unglycosylated pro-NGF, pro-BDNF, pro-NT-3, and pro-NT-4/5 are approximately 27.0, 27.8, 29.4, and 22.4 kDa, respectively. The GenBank accession numbers of human pro-NGF, pro-BDNF, pro-NT-3, and pro-NT-4/5 are AAA59931 (SEQ. ID. NO: 1), AAA69805 (SEQ. ID. NO: 2), AAA59953 (SEQ. ID. NO: 3), and AAA60154/AAA20549 (SEQ. ID. NO: 4), respectively. These sequences are incorporated herein by reference, and are displayed in FIGS. 1A-4A.

In its broadest embodiment, the present invention is directed to an isolated protein that comprises a pro-domain of a proneurotrophin. The pro-domain optionally further comprises a mature neurotrophin domain and a connector that joins the pro-domain and the mature neurotrophin domain. The definitions of these terms are as described below.

The definition of the pro-domain is not necessarily that commonly used in the literature. As used herein, the term "pro-domain of a proneurotrophin" or, simply "pro-domain" includes all or part of the amino acid sequence at the N-terminus of a native proneurotrophin, as described above, up to, but not including, the major proneurotrophin cleavage site.

The pro-domain of a proneurotrophin in accordance with the present invention includes all or part of the following amino acid sequences: amino acid residues 1 to approximately 117 of NGF (SEQ. ID. NO: 69), 1 to approximately 124 of BDNF (SEQ. ID. NO: 70), 1 to approximately 134 of NT-3 (SEQ. ID. NO: 71), and 1 to approximately 76 of NT-4/5 (SEQ. ID. NO: 72).

In a first embodiment, The pro-domain comprises at least a pro-domain conserved region, the conserved region being an amino acid sequence having at least approximately 85%, preferably at least approximately 90%, more preferably at least approximately 95% (i.e. one mismatch), and most preferably 100% identity to amino acid residues approximately at positions 79-98 of human NGF (SEQ. ID. NO: 73); 91-105 of human BDNF (SEQ. ID. NO: 74); 101-115 of human NT-3 (SEQ. ID. NO: 75), or 43-57 of human NT-4/5 (SEQ. ID. NO: 76). This region will be referred to herein as the pro-domain conserved region, or, simply, the conserved region.

In a second embodiment, the pro-domain of the first embodiment further comprises an amino acid sequence having at least approximately 85%, preferably at least approximately 90%, more preferably at least approximately 95% (i.e. one mismatch), and most preferably 100% identity to amino acid residues approximately at positions 99-117 of human NGF (SEQ. ID. NO: 77); 106-124 of human BDNF (SEQ. ID. NO: 78); 116-134 of human NT-3 (SEQ. ID. NO: 79); or 58-76 of human NT-4/5 (SEQ. ID. NO: 80).

In a third embodiment, the pro-domain of the first or second embodiments further comprises an amino acid sequence having at least approximately 85%, preferably at least approximately 90%, more preferably at least approximately 95% (i.e. one mismatch), and most preferably 100% identity to amino acid residues approximately at positions 66-78 of human NGF (SEQ. ID. NO: 81); 73-90 of human BDNF (SEQ. ID. NO: 82); 83-100 of human NT-3 (SEQ. ID. NO: 83); or 25-42 of human NT-4/5 (SEQ. ID. NO: 84).

In a fourth embodiment, the pro-domain of the third embodiment further comprises an amino acid sequence having at least approximately 85%, preferably at least approximately 90%, more preferably at least approximately 95% (i.e. one mismatch), and most preferably 100% identity to amino acid residues approximately at positions 46-65 of human NGF (SEQ. ID. NO: 85); 57-72 of human BDNF (SEQ. ID. NO: 86); or 61-82 of human NT-3 (SEQ. ID. NO: 87).

In a fifth embodiment, the pro-domain comprises an amino acid sequence having at least approximately 85%, preferably at least approximately 90%, more preferably at least approximately 95%, and most preferably 100% identity to amino acid residues approximately at positions 46-117 of human NGF (SEQ. ID. NO: 88); 57-124 of human BDNF (SEQ. ID. NO: 89); 61-134 of human NT-3 (SEQ. ID. NO: 90); or 25-76 of human NT-4/5 (SEQ. ID. NO: 91).

Any of the pro-domains described above optionally comprise a signal sequence, preferably at the N-terminus. The signal sequence characteristically includes a stretch of hydrophobic amino acid residues that facilitates transport into the endoplasmic reticulum, and facilitates the secretion from cells. The signal sequences of the approximately 18 amino acid residues found at the N-terminus of native NGF (SEQ. ID. NO: 92), BDNF (SEQ. ID. NO: 93), and NT-3 (SEQ. ID. NO: 94), and of the approximately 24 amino acid residues found at the N-terminus of native NT-4/5 (SEQ. ID. NO: 95), constitute suitable signal sequences.

The pro-domains of the invention may extend to the N-terminus of any of the native proneurotrophins described above. The full length pro-domain may or may not comprise the signal sequence.

The invention also includes modified proneurotrophin proteins that are cleavage resistant. The modified proneurotrophins comprise a pro neurotrophin domain, a mature neurotrophin domain, and a connector that joins the pro-domain to the mature domain. The pro-domain may be any of the pro-domains mentioned above. The pro-domain is preferably at the N-terminal end of the sequence, and the mature domain is preferably at the C-terminal end.

The mature neurotrophin domain, also referred to herein as the mature domain, includes all or part of the amino acid sequence following the major proneurotrophin cleavage site of a native proneurotrophin. The mature domain may comprise all of the amino acid residues of a native, mature neurotrophin protein. Alternatively, the mature neurotrophin domain comprises less than all of the amino acid residues of a native, mature neurotrophin, but at least a sufficient number of amino acid residues to confer on the modified proneurotrophin selective binding to p75, and enhanced apoptosis of cells that express p75, relative to the corresponding mature neurotrophin. For example, the amino acid sequence of a mature neurotrophin domain may comprise at least about 20, 40, 60, 80, or 100 amino acid residues from either the N-terminus of a mature neurotrophin protein, the C-terminus of a mature neurotrophin protein, or anywhere else from within the internal sequence of a mature neurotrophin protein.

Therefore, the mature neurotrophin domain in accordance with the present invention includes all or part of the following amino acid sequences: amino acid residues 122 to 241 of NGF (SEQ. ID. NO: 96), 129 to 247 of BDNF (SEQ. ID. NO: 97), 139 to 257 of NT-3 (SEQ. ID. NO: 98), and 81 to 210 of NT-4/5 (SEQ. ID. NO: 99).

The modified proneurotrophins of the present invention lack a major proneurotrophin cleavage site. In the modified proneurotrophins, the major cleavage site is replaced by a connector, which is protease cleavage resistant. The connector may be a chemical bond, preferably a covalent or coordinate bond, or any chemical group that is capable of stably joining the pro-domain and the mature domain, and that is protease cleavage resistant.

A example of a chemical group useful as a connector is an oligopeptide. The oligopeptide may be any oligopeptide that is protease cleavage resistant, as long as the modified proneurotrophin retains its biological activity, i.e. greater affinity for p75 receptors than mature neurotrophins, and greater capacity to induce apoptosis of cells that express p75. The connector may be a single amino acid, a dipeptide, a tripeptide, a tetrapeptide, a pentapeptide, a hexapeptide or a peptide chain of any length, preferably less than twenty amino acids, more preferably less than ten amino acids. The connector is preferably a tetrapeptide, as is the major proneurotrophin cleavage site.

Any amino acid or amino acid sequence may be used in the connector. Some examples of suitable amino acid residues include alanine (A), serine (S), threonine (T), and glycine (G).

Any one or more of the amino acid residues in the major proneurotrophin cleavage site may be replaced in order to prevent cleavage. Preferably, one or all of the dibasic residues, arginine (R) and lysine (K), is replaced.

Some examples of suitable oligopeptides include A-A, A-S, S-T, P-G, S-S-S, S-G-A, S-A-A, S-A-P, R-S-A-T (SEQ. ID. NO: 27), G-G-A-P (SEQ. ID. NO: 28), and S-S-T-P (SEQ. ID. NO: 29). Particularly favored oligopeptides include the tetrapeptides: R-S-A-A (SEQ. ID. NO: 30); R-V-A-A (SEQ. ID. NO: 31); and A-A-A-A (SEQ. ID. NO: 32).

A connector that is "resistant to protease cleavage" means that the connector is substantially uncleavable by a protease that is able to cleave a native proneurotrophin as a result of recognition of the major proneurotrophin cleavage site by the protease. Preferably, a connector that is resistant to protease cleavage is completely uncleavable by such a protease.

Examples of proteases that cleave native proneurotrophins include serine proteases. Examples of such serine proteases are the proprotein convertases, such as furin. Accordingly, the connector is substantially uncleavable, and preferably completely uncleavable, by such serine proteases.

The inventors have also surprisingly discovered that certain matrix metalloproteinases (MMPs), such as MMP-3 and MMP-7, and plasmin are also actively involved in the cleavage of proneurotrophins. Plasmin is produced from plasminogen by the action of the plasminogen activator proteinases, such as tissue plasminogen activator (tPA) and urinary plasminogen activator (uPA). Accordingly, the modified proneurotrophins of the invention are further modified to eliminate the cleavage sites for these proteases.

In order to increase their resistance to protease cleavage, the proteins of the invention preferably lack one or more protease cleavage sites in addition to the major cleavage sites, and most preferably lack all protease cleavage sites. Such sites include, for example, dibasic sites, such as R-R, R-K, K-R, and K-K, as well as other cleavage sites, such as L-L sites. Some examples of the sites that the proteins of the invention preferably lack include the following:

The sites in human NGF (SEQ. ID. NO: 1) at positions 49-50 (R-R), 78-79 (K-K), 79-80 (K-R), 80-81(R-R), and 132-134 (E-F-S).

The sites in human BDNF (SEQ. ID. NO: 2) at positions 56-57 (L-T), 106-107 (L-L), 108-109, (F-L), 109-110 (L-L), 111-112 (E-E), 134-135 (R-R), and 137-139 (E-L-S).

The sites in human NT-3 (SEQ. ID. NO: 3) at positions 92-93 (L-L), 105-106 (L-L), 97-98 (R-R), 148-150 (E-Y-S).

The sites in human NT-4/5 (SEQ. ID. NO: 4) at positions 58-59 (L-L), 60-61 (F-L), 61-62 (L-L), 90-91 (R-R), and 93-95 (E-L-A).

The proteins of the invention comprise all of the isoforms that result from cleavage in any of the pro-domains. For example, the pro-domains comprise isoforms having approximate amino acid residue numbers 1-117 (SEQ. ID. NO: 69), 19-117 (SEQ. ID. NO: 100), 51-117 (SEQ. ID. NO: 101), 81-117 (SEQ. ID. NO: 102), or 82-117 (SEQ. ID. NO: 103) of the human pro-domain of NGF; approximate amino acid residue numbers 1-124 (SEQ. ID. NO: 70), 19-124 (SEQ. ID. NO: 104), 58-124 (SEQ. ID. NO: 105), 110-124 (SEQ. ID. NO: 106), 111-124 (SEQ. ID. NO: 107), or 113-124 (SEQ. ID. NO: 108) of the human pro-domain of BDNF; approximate amino acid residue numbers 1-134 (SEQ. ID. NO: 71), 19-134 (SEQ. ID. NO: 109), or 99-134 (SEQ. ID. NO: 110) of the human pro-domain of NT-3; or approximate amino acid residue numbers 1-76 (SEQ. ID. NO: 72), 25-76 (SEQ. ID. NO: 111), 62-76 (SEQ. ID. NO: 112), or 63-76 (SEQ. ID. NO: 113) of the human pro-domain of NT-4/5. Similarly, the modified proneurotrophins comprise (i) all or part of a mature domain, (ii) a connector, and (iii) approximate amino acid residue numbers 1-117 (SEQ. ID. NO: 69), 19-117 (SEQ. ID. NO: 100), 51-117 (SEQ. ID. NO: 101), 81-117 (SEQ. ID. NO: 102), or 82-117 (SEQ. ID. NO: 103) of the human pro-domain of NGF; approximate amino acid residue numbers 1-124 (SEQ. ID. NO: 70), 19-124 (SEQ. ID. NO: 104), 58-124 (SEQ. ID. NO: 105), 110-124 (SEQ. ID. NO: 106), 111-124 (SEQ. ID. NO: 107), or 113-124 (SEQ. ID. NO: 108) of the human pro-domain of BDNF; approximate amino acid residue numbers 1-134 (SEQ. ID. NO: 71), 19-134 (SEQ. ID. NO: 109), or 99-134 (SEQ. ID. NO: 110) of the human pro-domain of NT-3; and approximate amino acid residue numbers 1-76 (SEQ. ID. NO: 72), 25-76 (SEQ. ID. NO: 111), 62-76 (SEQ. ID. NO: 112), or 63-76 (SEQ. ID. NO: 113) of the human pro-domain of NT-4/5.

The isoforms described above are derived from cleavage sites present in the pro-domain. In some instances, the cleavage site may occur approximately four amino acids upstream of the sequence recognition site. For example, proteases that recognize LL sites often cleave within four amino acids upstream of the LL sequence recognition site. In other instances, the cleavage site may occur approximately four amino acids downstream of the sequence recognition site. For example, the protease furin often cleaves approximately four amino acids downstream of the sequence recognition site. Therefore, the above-mentioned amino acid residue numbers are approximate.

The examples above all refer to human pro-domains and human mature domains. The comparable positions in the domains of species other than humans can easily be determined by those of ordinary skill. The proneurotrophin sequences of various species is provided in FIGS. 5B-5E. In FIG. 5B, human NGF (SEQ. ID. NO: 6), gorilla NGF (SEQ. ID. NO: 7), rat NGF (SEQ. ID. NO: 8), mouse NGF (SEQ. ID. NO: 9), bovine NGF (SEQ. ID. NO: 10), chicken NGF (SEQ. ID. NO: 11), and xenopus NGF (SEQ. ID. NO: 12). In FIG. 5C, human BDNF (SEQ. ID. NO: 2), bovine BDNF (SEQ. ID. NO: 13), rat BDNF (SEQ. ID. NO: 14), mouse BDNF (SEQ. ID. NO: 15), and chick BDNF (SEQ. ID. NO: 16). In FIG. 5D, human NT-3 (SEQ. ID. NO: 3), rat NT-3 (SEQ. ID. NO: 17), mouse NT-3 (SEQ. ID. NO: 18), chick NT-3 (SEQ. ID. NO: 19), and xenopus (SEQ. ID. NO: 20). In FIG. 5E, human NT-4/5 (SEQ. ID. NO: 4), rat NT-4/5 (SEQ. ID. NO: 21), and xenopus NT-4/5 (SEQ. ID. NO: 22).

The protease cleavage sites described above may be eliminated completely and not replaced, or may be replaced by any of the oligopeptides described above as being useful as connectors. The oligopeptide is preferably a dipeptide, preferably comprising A, S, T, P, or G. Some examples include A-A, T-A, P-T, and G-A.

The elimination or replacement of the major proneurotrophin cleavage site, or of one or more additional protease cleavage sites in preparing the proteins of the invention, including the modified proneurotrophins, may be achieved by standard techniques well known in the art. Such techniques include, inter alia, protein synthesis; synthesis and expression of nucleic acid molecules; and site directed mutagenesis and expression of nucleic acid molecules. See, for example, Kolbeck et al., "Characterisation of neurotrophin dimers and monomers," Eur. J. Biochem. 225, 995-1003 (1994).

Due to the high conservation of neurotrophin sequences, the pro-domain and the mature domain may be from the same vertebrate or from different vertebrates. The vertebrate may be a non-mammalian vertebrate, such as a frog, fish, bird, or chicken. Alternatively, the vertebrate may be a mammal. The mammal may be a farm animal, such as a goat, horse, pig, or cow; a pet animal, such as a dog or cat; a laboratory animal, such as a mouse, rat, or guinea pig; or a primate, such as a monkey, orangutan, ape, chimpanzee, or human. The GenBank accession numbers of sequences of some vertebrate neurotrophins are shown in Table I (A-D) below. The sequences of pro-domains and mature domains are useful in the proteins of the invention, and are incorporated by reference herein.

Moreover, the sequence of the pro-domain and the sequence of the mature domain may be those of the same proneurotrophin or of different proneurotrophins, independent of whether the sequences are from the same or from a different vertebrate. Accordingly, the pro-domain may have the sequence of any proneurotrophin domain. Similarly, and independently, the mature domain may have the sequence of any mature neurotrophin domain. Some examples of such chimeric modified proneurotrophins include:

Pro-NGF-connector-mature BDNF;
Pro-BDNF-connector-mature NT-4/5;
Pro-NT-3-connector-mature NGF;
Pro-BDNF-connector-mature NT-3; and
Pro-BDNF-connector-mature NGF.

The proteins of the invention, such as the modified proneurotrophins described above, including chimeric modified proneurotrophins, may exist as monomers or multimers. The multimers may comprise any number of proneurotrophin units, such as a dimer, trimer, or tetramer. The proneurotrophin units may be all the same proneurotrophin, in which case the multimer is a homomultimer. Alternatively, the multimer may comprise different proneurotrophin units, in which case the multimer is a heteromultimer. Some examples of heteromultimers include derivatives of NGF-BDGF, NGF-NT-3, BDGF-NT4/5, BDGF-NT-3, and NGF-BDGF-NT4/5.

TABLE I

A: Sequences of Representative Pro and Mature Domains of Pro-NGF (Major Cleavage Sites are Underlined)

| Species (GenBank Accession Number) | Pro-NGF Domain | Mature NGF Domain |
|---|---|---|
| Human (AAA59931) | MSMLFYTLITAFLIGIQAEPHSESNVPAGHTIPQVHWTKLQHSLDTALR RARSAPAAAIAARVAGQTRNITVDPRLFKKRRLRSPRVLFSTQPPREAA DTQDLDFEVGGAAPFNRTHRSKR (SEQ. ID. NO: 33) | SSSHPIFHRGEFSVCDSVSVWVGDKTTATDIKGKEVMVLGE VNINNSVFKQYFFETKCRDPNPVDSGCRGIDSKHWNSYCTT THTFVKALTMDGKQAAWRFIRIDTACVCVLSRKAVRRA (SEQ. ID. NO: 34) |
| Rat (AAA41697) | VHSVMSMLFYTLITAFLIGVQAEPYTDSNVPEGDSVPEAHWTKLQHSLD TALRRARSAPAEPIAARVTGQTRNITVDPKLFKKRRLRSPRVLFSTQPP PTSSDTLDLDFQAHGTISFNRTHRSKR (SEQ. ID. NO: 35) | SSTHPVFHMGEFSVCDSVSVWVGDKTTATDIKGKEVTVLGE VNINNSVFKQYFFETKCRAPNPVESGCRGIDSKHWNSYCTT THTFVKALTTDDKQAAWRFIRIDTACVCVLSRKAARRG (SEQ. ID. NO: 36) |
| Mouse (P01139) | MSMLFYTLITAFLIGVQAEPYTDSNVPEGDSVPEAHWTKLQHSLDTALR RARSAPTAPIAARVTGQTRNITVDPRLFKKRRLHSPRVLFSTQPPPTSS DTLDLDFQAHGTIPFNRTHRSKR (SEQ. ID. NO: 37) | SSTHPVFHMGEFSVCDSVSVWVGDKTTATDIKGKEVTVLAE VNINNSVFRQYFFETKCRASNPVESGCRGIDSKHWNSYCTT THTFVKALTTDEKQAAWRFIRIDTACVCVLSRKATRRG (SEQ. ID. NO: 38) |
| Chick (CAA27633) | VHSVMSMLYYTLIIAFLIGTQAAPKSEDNGPLEYPAEHSLPSTQQSNGQ HIAKAAPQTTHGRFAWMPDGTEDLNIAMDQNFFKKKRFRSSRVLFSTQP PPVSRKGQSTGFLSSAVSLNRTARTKR (SEQ. ID. NO: 39) | TAHPVLHRGEFSVCDSVSMWVGDKTTATDIKGKEVTVLGEV NINNNVFKQYFFETKCRDPRPVSSGCRGIDAKHWNSYCTTT HTFVKALTMEGKQAAWRFIRIDTACVCVLSRKSGRP (SEQ. ID. NO: 40) |
| Xenopus (CAA39249) | VDRVMSMLYYTLLIAILISVQAAPKTKDHAPARSSAKSRIPHHTHRTKS LHHSHGKLEAKEPSYFRNVTVDPKLFRKRKFRSPRVLFSTQPPPLSEDF QHLEYLDDEESLNKTIRAKR (SEQ. ID. NO: 41) | TVHPVLHKGEYSVCDSVSMWVGEKTKATDIKGKEVTVLGEV NINNSVFKQYFFETKCRDPKPVSSGCRGIDAKHWNSYCTTT HTFVKALTMEGKQAAWRFIRIDTACVCVLSRKGRT (SEQ. ID. NO: 42) |

B: Sequences of Representative Pro and Mature Domains of Pro-BDNF (Major Cleavage Sites are Underlined)

| Species (GenBank Accession Number) | Pro-BDNF Domain | Mature BDNF Domain |
|---|---|---|
| Human (AAA69805) | MTILFLTMVISYFGCMKAAPMKEANIRGQGGLAYPGVRTHGTLESVNGP KAGSRGLTSLADTFEHVIEELLDEDQKVRPNEENNKDADLYTSRVMLSS QVPLEPPLLFLLEEYKNYLDAANMSMRVRR (SEQ. ID. NO: 43) | HSDPARRGELSVCDSISEWVTAADKKTAVDMSGGTVTVLEK VPVSKGQLKQYFYETKCNPMGYTKEGCRGIDKRHWNSQCRT TQSYVRALTMDSKKRIGWRFIRIDTSCVCTLTIKRGR (SEQ. ID. NO: 44) |
| Rat (AAA63483) | MTILFLTMVISYFGCMKAAPMKEANVHGQGNLAYPAVRTHGTLESVNGP RAGSRGLTTTSLADTFEHVIEELLDEDQKVRPNEENHKDADLYTSRVML SSQVPLEPPLLFLLEEYKNYLDAANMSMRVRR (SEQ. ID. NO: 45) | HSDPARRGELSVCDSISEWVTAADKKTAVDMSGGTVTVLEK VPVSKGQLKQYFYETKCNPMGYTKEGCRGIDKRHWNSQCRT TQSYVRALTMDSKKRIGWRFIRIDTSCVCTLTIKRGR (SEQ. ID. NO: 46) |
| Mouse (CAA39159) | MTILFLTMVISYFGCMKAAPMKEVNVHGQGNLAYPGVRTHGTLESVNGP RAGSRGLTTTSLADTFEHVIEELLDEDQKVRPNEENHKDADLYTSRVML SSQVPLEPPLLFLLEEYKNYLDAANMSMRVRR (SEQ. ID. NO: 47) | HSDPARRGELSVCDSISEWVTAADKKTAVDMSGGTVTVLEK VPVSKGQLKQYFYETKCNPMGYTKEGCRGIDKRHWNSQCRT TQSYVRALTMDSKKRIGWRFIRIDTSCVCTLTIKRGR (SEQ. ID. NO: 48) |
| Chick (AAC42220) | MTILFLTMVISYFSCMKAAPMKEASVRGHGSLAYPGLRTHGTLESLTGP NAGSRGLTSLADTFEHVIEELLDEDQDIQPSEENKDADLYTSRVMLSSQ VPLEPPLLFLLEEYKNYLDAANMSMRVRR (SEQ. ID. NO: 49) | HSDPARRGELSVCDSTSEWVTAAEKKTAVDMSGATVTVLEK VPVPKGQLKQYFYETKCNPKGYTKEGCRGIDKRHWNSQCRT TQSYVRALTMDNKKRVGWRFIRIDTSCVCTLTIKRGR (SEQ. ID. NO: 50) |

TABLE I-continued

| Bovine (CAA66488) | ILFLTMVISYFGCMKAAPMKEANLRAQGSLTYPGVRTHGTLESMNGPKV GSRGLTSSSSLADTFEHVIEELLDEDQKVRPSEENNKDADMYTSRVMLS SQVPLEPPLLFLLEEYKNYLDAANMSMRVRR (SEQ. ID. NO: 51) | HSDPARRGELSVCDSISEWVTAADKRLAVDMSGGTVTVLEK VPVSKGQLKQYFYETKCNPMGYTKEGCRGIDKRHWNSQCRT TQSYVRALTMDSKKRIGWRFIRIDTSCVCTLTIKRGR (SEQ. ID. NO: 52) |
|---|---|---|

C: Sequences of Representative Pro and Mature Domains of Pro-NT-3 (Major Cleavage Sites are Underlined)

| Species (GenBank Accession Number) | Pro-NT-3 Domain | Mature NT-3 Domain |
|---|---|---|
| Human (AAA59953) | MSILFYVIFLAYLRGIQGNNMDQRSLPEDSLNSLIIKLIQADILKNKLS KQMVDVKENYQSTLPKAEAPREPERGGPAKSAFQPVIAMDTELLRQQRR YNSPRVLLSDSTPLEPPPLYLMEDYVGSPVVANRTSRRKR (SEQ. ID. NO: 53) | YAEHKSHRGEYSVCDSESLWVTDKSSAIDIRGHQVTVLGEI KTGNSPVKQYFYETRCKEARPVKNGCRGIDDKHWNSQCKTS QTYVRALTSENNKLVGWRWIRIDTSCVCALSRKIGRT (SEQ. ID. NO: 54) |
| Rat (AAA41727) | MSILFYVIFLAYLRGIQGNNMDQRSLPEDSLNSLIIKLIQADILKNKLS KQMVDVKENYQSTLPKAEAPREPEQGEATRSEFQPMIATDTELLRQQRR YNSPRVLLSDSTPLEPPPLYLMEDYVGNPVVTNRTSPRRKR (SEQ. ID. NO: 55) | YAEHKSHRGEYSVCDSESLWVTDKSSAIDIRGHQVTVLGEI KTGNSPVKQYFYETRCKEARPVKNGCRGIDDKHWNSQCKTS QTYVRALTSENNKLVGWRWIRIDTSCVCALSRKIGRT (SEQ. ID. NO: 56) |
| Mouse (CAA37348) | MSILFYVIFLAYLRGIQGNSMDQRSLPEDSLNSLIIKLIQADILKNKLS KQMVDVKENYQSTLPKAEAPREPEQGEATRSEFQPMIATDTELLRQQRR YNSPRVLLSDSTPLEPPPLYLMEDYVGNPVVANRTSPRRKR (SEQ. ID. NO: 57) | YAEHKSHRGEYSVCDSESLWVTDKSSAIDIRGHQVTVLGEI KTGNSPVKQYFYETRCKEARPVKNGCRGIDDKHWNSQCKTS QTYVRALTSENNKLVGWRWIRIDTSCVCALSRKIGRT (SEQ. ID. NO: 58) |
| Chick (AAA68880) | MSILFYVIFLAYLRGIQSTNMDQRSLPEDSMNSLIIKLIRADILKNKLS KQVMDVKENYQNIVQKVEDHQEMDGDENVKSDFQPVISMDTDLLRQQRR YNSPRVLLSDNTPLEPPPLYLTEDYVGSSVVLNRTSRRKR (SEQ. ID. NO: 59) | YAEHKSHRGEYSVCDSESLWVTDKSSAIDIRGHQVTVLGEI KTGNSPVKQYFYETRCKEAKPVKNGCRGIDDKHWNSQCKTS QTYVRALTSENNKLVGWRWIRIDTSCVCALSRKIGRT (SEQ. ID. NO: 60) |
| Xenopus (AAB17723) | MSILFYVMFLPYLCGIHATNMDKRNLPENSMNSLFIKLIQADLLKNKIS KQTVDTKENHQSTIPKPQILLDLDGDDNMKQDFQPVISLEAELVKQQKQ RRYKSPRVLLSDSLPLEPPPLYLMDDYIGHSTVVNNRTSRRKR (SEQ. ID. NO: 61) | FAEHKGHRGEYSVCDSESLWVTDKMNAIDIRGHQVTVLGEI KTGNSPVKQYFYETRCKEARPVKNGCRGIDDKHWNSQCKTS QTYVRALTSENNKMVGWRWIRIDTSCVCALSRKIGRSKNYL DAANNSMRVRR (SEQ. ID. NO: 62) |

D: Sequences of Representative Pro and Mature Domains of Pro-NT-4/5 (Major Cleavage Sites are Underlined)

| Species (GenBank Accession Number) | Pro-NT-4/5 Domain | Mature NT-4/5 Domain |
|---|---|---|
| Human (AAA60154) | MLPLPSCSLPILLLFLLPSVPIESQPPPSTLPPFLAPEWDLLSPRVVLS RGAPAGPPLLFLLEAGAFRESAGAPANRSRR (SEQ. ID. NO: 63) | GVSETAPASRRGELAVCDAVSGWVTDRRTAVDLRGREVEVLG EVPAAGGSPLRQYFFETRCKADNAEEGGPGAGGGGCRGVDRR HWVSECKAKQSYVRALTADAQGRVGWRWIRIDTACVCTLLSR TGRA (SEQ. ID. NO: 64) |
| Rat (AAA41728) | MLPRHSCSLLLFLLLLPSVPMEPQPPSSTLPPFLAPEWDLLSPRVALSR GTPAGPPLLFLLEAGAYGEPAGAPANRSRR (SEQ. ID. NO: 65) | GVSETAPASRRGELAVCDAVSGWVTDRRTAVDLRGREVEVLG EVPAAGGSPLRQYFFETRCKAESAGEGGPGVGGGGCRGVDRR HWLSECKAKQSYVRALTADSQGRVGWRWIRIDTACVCTLLSR TGRA (SEQ. ID. NO: 66) |
| Xenopus (CAA82906) | MILRLYAMVISYCCAICAAPFQSRTTDLDYGPDKTSEASDRQSVPNNFS HVLQNGFFPDLSSTYSSMAGKDWNLYSPRVTLSSEEPSGPPLLFLSEET VVHPEPANKTSRLKR (SEQ. ID. NO: 67) | ASGSDSVSLSRRGELSVCDSVNVWVTDKRTAVDDRGKIVTVM SEIQTLTGPLKQYFFETKCNPSGSTTRGCRGVDKKQWISECK AKQSYVRALTIDANKLVGWRWIRIDTACVCTLLSRTGRT (SEQ. ID. NO: 68) |

In another embodiment, the invention comprises a protein having at least a pro-domain of a proneurotrophin. Any of the pro-domains described above are suitable. The protein may be used as an intermediate to make the modified proneurotrophins described above, or may be used by itself as a substitute for the modified proneurotrophins in the methods of use described below. The protein optionally comprises additional amino acid residues, and may lack a mature domain. The protein further optionally contains a connector, as described above, and/or a major proneurotrophin cleavage site.

The pro-domain and the mature domain of the proteins of the invention may further comprise one or more groups commonly associated with amino acid chains. The groups may, for example, result from acetylation, phosphorylation, sulfation, glycosylation or lipidation. Further, the amino acid chain may be chemically bonded to additional peptide and non-peptide moieties. The non-peptide moiety may, for example, be a detectable label, a purification tag, such as a His tag, or a biologically active moiety such as an enzyme or a toxin.

The proneurotrophins of the invention include homologs of naturally occurring or native proneurotrophins. A homolog of a native proneurotrophin may be, for example, a substitution mutant, a mutant having an addition or insertion, or a deletion mutant of the protein. Substitutions in a sequence of amino acids are preferably with equivalent amino acids. Groups of amino acids known to be of equivalent character are listed below:

(a) Ala(A), Ser(S), Thr(T), Pro(P), Gly(G);
(b) Asn(N), Asp(D), Glu(E), Gln(O);
(c) His(H), Arg(R), Lys(K);
(d) Met(M), Leu(L), Ile(I), Val(V); and
(e) Phe(F), Tyr(Y), Trp(W).

Any substitutions, additions, and/or deletions in an amino acid sequence are permitted provided that the protein of the invention continues to satisfy the functional criteria described herein. An amino acid sequence that is substantially identical to another sequence, but that differs from the other sequence by means of one or more substitutions, additions, and/or deletions, is considered to be an equivalent sequence.

In order to compare a first amino acid or nucleic acid sequence to a second amino acid or nucleic acid sequence for the purpose of determining homology, the sequences are aligned so as to maximize the number of identical amino acid residues or nucleotides. The sequences of highly homologous proteins and nucleic acid molecules can usually be aligned by visual inspection. If visual inspection is insufficient, the nucleic acid molecules may be aligned in accordance with methods known in the art. Examples of suitable methods include those described by George, D. G. et al., in *Macromolecular Sequencing and Synthesis, Selected Methods and Applications*, pages 127-149, Alan R. Liss, Inc. (1988), such as formula 4 at page 137 using a match score of 1, a mismatch score of 0, and a gap penalty of −1.

Preferably, less than 15%, more preferably less than 10%, and still more preferably less than 5% of the number of amino acid residues in the sequence of a pro-domain or a mature domain are different (i.e., substituted for, inserted into, or deleted from) from the amino acid residues in the sequence of the corresponding domain of a naturally occurring proneurotrophin to yield the high affinity p75-binding protein of the invention. More preferably still, less than 3%, yet more preferably less than 2% and optimally less than 1% of the number of amino acid residues in a sequence are different from those in a naturally occurring sequence.

The proteins of the invention, including the modified proneurotrophins of the invention, are isolated. As used herein, the term "isolated" means substantially free from other biological components, as well as from materials that are used in preparation, isolation, characterization or purification of proteins. Some examples of other biological components include cellular components, culture media or components (including conditioned media and components thereof), affinity binding agents, such as immunoconjugates or antibodies and other serum components. Examples of materials that are used in preparation, isolation, or purification of proteins include separation media or membranes, such as nitrocellulose, chromatographic matrices, and electrophoretic gel media, including for instance, polyacrylamide and detergents, such as sodium dodecyl sulfate (SDS).

Preferably, the isolated material is at least about 25% to about 90% pure, i.e. free from other proteins and nucleic acid molecules. More preferably, the isolated material is at least about 50% to about 90% pure. Optimally, the isolated material is at least about 75% to about 90% pure.

Most preferably, the proteins of the invention, including the modified proneurotrophin, are purified. As used herein, the term "purified" means essentially pure as demonstrated by single band purity on electrophoresis in SDS-polyacrylamide gels (SDS PAGE). Preferably, the purified material is at least about 90% to about 99.9% pure. More preferably, the purified material is at least about 95% to about 99.9% pure. Optimally, the purified material is at least about 99% to about 99.9% pure.

Nucleic Acids Encoding Proneurotrophins, Vectors, Hosts, Site Directed Mutagenesis:

In a particular embodiment, the invention provides a nucleic acid molecule that encodes any of the proteins mentioned above, such as the pro-domains and the modified proneurotrophin resistant to cleavage by one or more proteases. Preferably, the sequence of the nucleic acid molecule exists in nature, preferably in a mammalian organism, more preferably, in a human. The encoded protein optionally further comprises a signal sequence and may or may not also include all or part of the mature neurotrophin domain. The nucleic acid may be a DNA molecule, such as for example cDNA or genomic DNA, or alternatively the nucleic acid may be an RNA molecule, such as for example mRNA.

The nucleic acid of the invention may be incorporated into a recombinant vector for replication to amplify the nucleic acid, or for expression and isolation/purification of the encoded protein. The recombinant vector may be any recombinant vector, such as a plasmid, a cosmid or a phage. Recombinant vectors have an origin of replication from which copying of the vector and incorporated nucleic acid sequences is initiated. The vector may further include a selectable marker, such as for instance a drug resistance marker, a detectable gene marker or an origin of replication for a second host cell and also a multiple cloning site for ease of manipulation of the inserted nucleic acid.

Pharmaceutical Compositions:

In a preferred embodiment, the proteins of the invention, including the pro-domains and the cleavage resistant proneurotrophins described above, are incorporated in pharmaceutical compositions suitable for use as a medicament, for human or animal use. The pharmaceutical compositions may be for instance, in an injectable formulation, a liquid, cream or lotion for topical application, an aerosol, a powder, granules, tablets, suppositories or capsules, such as for instance, enteric coated capsules etc. The pharmaceutical compositions may also be delivered in or on a lipid formulation, such as for instance an emulsion or a liposome preparation. The pharmaceutical compositions are preferably sterile, non-pyrogenic and isotonic preparations, optionally with one or more of the pharmaceutically acceptable additives listed below.

Pharmaceutical compositions of the cleavage resistant proteins of the invention are preferably stable compositions which may comprise one or more of the following: a stabilizer, a surfactant, preferably a nonionic surfactant, and optionally a salt and/or a buffering agent. The pharmaceutical composition may be in the form of an aqueous solution, or in a lyophilized form.

The stabilizer may, for example, be an amino acid, such as for instance, glycine; or an oligosaccharide, such as for example, sucrose, tetralose, lactose or a dextram. Alternatively, the stabilizer may be a sugar alcohol, such as for instance, mannitol; or a combination thereof. Preferably the stabilizer or combination of stabilizers constitutes from about 0.1% to about 10% weight for weight of the proneurotrophin.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The pharmaceutical compositions of the present invention may additionally contain one or more conventional additive. Some examples of such additives include a solubilizer such as for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

Methods of Use

The proteins of the invention, especially when incorporated into pharmaceutical compositions as described above, are useful in methods for the treatment of certain conditions in a mammal. The conditions are mediated by, or involve, cells that express the p75 receptor. The mammal may be a farm animal, such as a goat, horse, pig, or cow; a pet animal, such as a dog or cat; a laboratory animal, such as a mouse, rat, or guinea pig; or a primate, such as a monkey, orangutan, ape, chimpanzee, or human.

For conditions characterized by undesirable cell growth, it is beneficial to induce apoptosis. For conditions characterized by undesirable cell death, it is beneficial to inhibit apoptosis. The invention includes both types of methods.

Methods to Induce Apoptosis

In one embodiment, the invention relates to a method for preventing or inhibiting growth of unwanted cells that express p75 receptors. Unwanted cell growth occurs, for example, in malignant cells, such as tumor cells, and in atherosclerotic plaques, especially in the smooth muscle cells of atherosclerotic plaques and vascular ischemias. The malignant cells may, for example, be melanoma cells, lymphoma cells, leukemic cells, prostate cells, pancreatic cells, cells of the testis, lung, brain or heart, or cells of the nervous system, such as cells of the central or peripheral nervous systems. Malignant nervous system cells include malignant neurons and glia cells, such as, for example, medulloblastomas, astrocytomas, and malignant oligodendrocytes.

Without wishing to be bound by theory, it is believed that the cleavage resistant proteins bind the p75 receptor on the unwanted cells, initiating a commitment to programmed cell death (apoptosis). The invention provides methods of treatment of conditions that are mediated by, or that involve, cells that express the p75 receptor. At least three embodiments of the methods lead to enhanced apoptosis:

The first embodiment involves the administration of a protein of the invention in vivo to a human or animal undergoing treatment or otherwise in need thereof. As mentioned above, the proteins of the invention either lack a mature domain or are resistant to one or more proteases that would otherwise be effective in the cleavage of the protein to a mature neurotrophin or to a neurotrophin form with residual trk-binding activity. The protein binds the p75 receptor on the surface of cells that are involved in or mediate the condition. The binding of the cleavage resistant proneurotrophin to the p75 receptor induces apoptosis of the cell.

The second embodiment involves the administration to a mammal of an inhibitor of a protease that cleaves the major protease cleavage site and/or other cleavage sites of a proneurotrophin. The inhibition reduces or prevents the processing of proneurotrophin to mature neurotrophin. The proneurotrophin binds the p75 receptors on the surface of the cells involved in or mediating the condition, disease or disorder being treated. Binding of the proneurotrophin to the p75 receptors induces apoptosis, as described above.

The third embodiment involves a combination of one of the above embodiments with administration of an inhibitor of trk activation. This additional treatment inhibits signaling initiated by any trk receptors that may be present. Activation is initiated by neurotrophin binding and autophosphorylation of the trk receptor. The inhibitor of trk activation blocks trk autophosphorylation, and thereby also blocks subsequent kinase activation in the signal transduction pathways activated by trk.

These methods are effective for any cells that express trk receptors as well as those that express the p75 receptor. As shown in Example 7, for example, superior cervical ganglia neurons coexpress both p75 and trk A receptors. Treatment of the neurons with pro-NGF resulted in cell death. Treatment with mature NGF resulted in very little cell death. Therefore, any of the molecules of the invention are capable of inducing p75-mediated apoptosis in vitro and in vivo in both the presence and absence of trk.

The methods are especially effective in cells in which trk receptors, if present, are not activated. The level of expression of the p75 receptor may be a normal level of expression, a higher than normal level of expression or even a lower than normal level of expression of p75.

A normal level of p75 receptor expression on the surface of a cell is from about 50,000 to about 100,000 such receptors per cell. A higher than normal level of p75 receptor expression includes all cells expressing more than about 100,000 p75 receptors per cell, preferably more than about 150,000 of the p75 receptors per cell; more preferably more than about 200,000 p75 receptors per cell; still more preferably more than about 250,000 p75 receptors per cell and optimally up to about 1,000,000 or more p75 receptors per cell. Cells expressing a lower than normal level of p75 receptors typically have from about 100 to about 50,000 p75 receptors per cell.

In yet another particular embodiment, the invention provides a method for inhibiting activation of the trk receptors of a cell of a mammal in need of such treatment. The method includes the step of administering an effective amount of an inhibitor that inhibits a protease that cleaves the major protease cleavage site of a proneurotrophin. The inhibition of the cleavage of proneurotrophin to mature neurotrophin has the effect of preventing the activation of the cognate trk receptors of the cell by the mature neurotrophin.

The protease inhibitor in any of the methods mentioned above may be any inhibitor that inhibits a protease that cleaves the major protease cleavage site of a proneurotrophin. Some classes of proteases include serine proteases, or proprotein convertases, such as for instance a furin. Alternatively, the protease that cleaves the major protease cleavage site of a proneurotrophin may be plasmin, (activated by a plasminogen activator such as tissue plasminogen activator or urinary plasminogen activator) or a matrix metalloproteinase, such as for instance, MMP-3 or MMP-7.

Some examples of furin inhibitors include, for example, Furin Inhibitor I (Decanoyl-Arg-Val-Lys-Arg-CMK) and Furin Inhibitor II (hexa-(D) arginine), both of which are available from Calbiochem. Some examples of plasmin inhibitors include, for example, epsilon amino caproic acid, tramexanic acid, alpha-2 macroglobulin or aprotinin (See *Anes. Anal.* 2001, 92: 775 and *Ann Thorac. Surg.* 2000, 70: 1300 for details of these inhibitors). Some examples of inhibitors of matrix metalloproteinases include tetracycline derivatives and other non-peptidic inhibitors such as AG3340 (from Agouron), BAY 12-9566 (from Bayer), BMS-275291 (from Bristol-Myers Squibb) and CGS 27023A (from Novartis) or the peptidomimetics marimastat and Batimastat (from British Biotech), and the MMP-3 (stromelysin-1) inhibitor, Ac-RCGVPD-NH$_2$ available from Calbiochem (San Diego, Calif.). See Hidalgo et al. 2001. *J. Natl. Can. Inst.* 93: 178-93 for a review of MMP inhibitors in cancer therapy.

In yet another embodiment, the invention provides a method for inducing apoptosis of a cell of a mammal in need thereof, the cell being susceptible to initiation of apoptosis by the binding of proneurotrophin to p75 receptors. The method includes the step of administering to the mammal an effective amount of a combination of a protein of the invention along with an inhibitor of trk activation. The inhibitor of trk activation may be any inhibitor of trk activation. Some examples of trk activation include a kinase inhibitor such as for instance, an indolecarbazole derivative. Examples of indolecarbazole derivatives include the kinase inhibitor K252a described by Ruggeri et al. 1999. *Curr. Med. Chem.* 6:845-57. The compound K252a from Cephalon is currently in clinical trials as a candidate for the treatment of pathological conditions of the prostate gland, e.g., benign prostatic hypertrophy or prostate cancer.

In yet a further embodiment, the invention provides a method for cleaving a proneurotrophin protein to yield a mature neurotrophin. The method comprises contacting the proneurotrophin protein with a particular matrix metalloproteinase. Specifically, the proneurotrophin protein is contacted with MMP-3 or MMP-7. Alternatively, the proneurotrophin protein is contacted with plasmin. Preferably, the proneurotrophin protein is pro-BDNF.

In a further particular embodiment, the invention provides a pharmaceutical composition comprising a protein of the present invention in combination with an inhibitor that inhibits a protease that cleaves the major protease cleavage site of a proneurotrophin. The combination is preferably in a formulation suitable for use as a medicament for human or animal use as described above.

In another further particular embodiment, the invention provides a method of treating a condition, disease or disorder mediated by or involving cells with any appreciable level of p75 receptor expression. The method involves administering an effective amount of a pharmaceutical composition comprising the above-recited combination of a protein of the invention in combination with an inhibitor that inhibits a protease that cleaves the major protease cleavage site of a proneurotrophin.

In yet a further particular embodiment, the invention provides a method of treating a condition, disease or disorder mediated by or involving cells with any appreciable level of p75 receptor expression, by administering an effective amount of a pharmaceutical composition comprising a protein of the invention in combination with an inhibitor that inhibits trk activation.

Methods of Inhibiting Apoptosis

In another embodiment, the invention relates to a method for inhibiting apoptosis of a cell in a mammal in need thereof. The method comprises inhibiting unwanted binding of a proneurotrophin to a p75 receptor.

The proneurotrophin may be any pro-neurotrophin, e.g., pro-NGF, pro-BDNF, pro-NT-3, or pro-NT-4/5. In this specification, a proneurotrophin refers to an entire proneurotrophin, or to any of the proneurotrophin isoforms that results from cleavage of a pro-domain, such as the isoforms described above.

The cell may be any cell that expresses p75, and that undergoes p75-mediated apoptosis. Some examples of suitable cells include cells of the nervous system, testis, lung, brain, and heart, such as cardiomyocytes.

Cells of the nervous system include the various cells of the central nervous system and of the peripheral nervous system. For example, the cells may be neurons or glia cells. Some examples of glia cells include oligodendrocytes, Schwann cells and astrocytes.

Moreover, p75 receptors are present in hair follicles of humans. Typically, the p75 receptors are on keratinocytes and epithelial cells of the outer root sheath.

In a further embodiment, the present invention relates to a method for inhibiting and treating apoptosis-mediated hair follicle regression (e.g. hair loss and baldness) in a human in need thereof. The method comprising administering to the human an effective amount of a molecule that inhibits the binding of a proneurotrophin to a p75 receptor. Other than the part of the body treated, the methods described elsewhere in this application for inhibiting apoptosis, including modes of administration, may be used in the present embodiment. The preferred mode of administration is topical administration to the skin in the area of the hair follicle regression.

The method comprises administering to a mammal a molecule that inhibits the binding of a proneurotrophin to a p75 receptor. A molecule is considered to inhibit the binding of a proneurotrophin to a p75 receptor if the molecule causes a significant reduction in such binding, and the reduction in binding causes a significant reduction in apoptosis. A reduction is considered significant, for example, if the reduction is at least about 10%, preferably at least about 25%, more preferably at least about 75%, and most preferably at least about 90%.

The molecule may be any molecule that inhibits the binding of a proneurotrophin to a p75 receptor. In one embodiment, the molecule binds specifically to the p75 receptor, and thereby blocks binding of the proneurotrophin to a p75 receptor, but does not activate the p75 receptor.

Some suitable examples of such molecules comprise an antibody hypervariable region that binds specifically to p75 receptors. The hypervariable region may be used alone, or may be part of an entire antibody variable region. The variable region may further comprise an antibody constant region. These molecules may be in the form of antibodies, or any fragment of antibodies, as described above.

The molecule that binds specifically to the p75 receptor may also be a small molecule or an oligopeptide. The small molecule or oligopeptide binds specifically to the p75 receptor, blocks binding of the proneurotrophin to a p75 receptor, but does not lead to the biological activity that is caused by binding of the p75 receptor to the proneurotrophin.

Such small molecules and oligopeptides can be discovered by methods well known in the art. Typically, discovering such molecules involves providing a cell that expresses p75, providing a small molecule or oligopeptide to be tested, and determining whether the small molecule or oligopeptide to be tested binds to a p75 receptor and, optionally, results in the biological activity caused by binding of a proneurotrophin to a p75 receptor. If the molecule binds with high affinity to the p75 receptor, it is a candidate for use in inhibiting apoptosis. If the molecule binds to the p75 receptor with high affinity and blocks binding of the proneurotrophin to a p75 receptor, it is a stronger candidate. If, in addition to blocking binding, the molecule also fails to cause the biological activity expected from activating a p75 receptor, e.g. apoptosis, the molecule is a candidate for pre-clinical or clinical trials.

The oligopeptide has at least approximately four amino acid residues, preferably at least approximately five amino acid residues, and more preferably at least approximately six amino acid residues. The maximum number of amino acid residues is not important, as long as the oligopeptide has the desirable properties mentioned above. The oligopeptide may be linear or cyclic. A cyclic peptide is a linear protein in which a carboxy group, usually the C-terminal carboxy group, forms an amide bond with an amino group, usually the N-terminal amino group.

Some examples of oligopeptides include:

S/T-P/S-R-V-(Z)$_z$ (SEQ. ID. NO: 115)

S/T-P/S-R-V-L/M/V-(Z)$_z$ (SEQ. ID. NO: 116)

S/T-P/S-R-V-L/M/V-F/L-(Z)$_z$ (SEQ. ID. NO: 117)

S/T-P/S-R-V-L/M/V-F/L-S-(Z)$_z$ (SEQ. ID. NO: 118)

Wherein Z represents any alpha amino acid and z represents any number from 0 to approximately 20, preferably from 0 to approximately 10, and more preferably from 0 to approximately 5. Any of these oligopeptides may be cyclic.

Small molecules include organic compounds, organometallic compounds, salts of organic and organometallic compounds, saccharides, amino acids, and nucleotides. Small molecules typically have molecular weights less than approximately 450 Daltons. Small molecules include compounds that are found in nature as well as synthetic compounds.

In addition to molecules that bind specifically to p75 receptors, the present invention includes molecules that bind specifically to the proneurotrophin. The proneurotrophin can be any proneurotrophin, such as the native proneurotrophin molecules identified above. The molecules preferably bind with substantially greater affinity, and preferably bind exclusively, to a proneurotrophin, relative to a mature neurotrophin.

Some suitable examples of molecules that bind specifically to proneurotrophins include molecules that comprise the extracellular domain of a p75 receptor, but that lack the intracellular and trans-membrane domains of a p75 receptor. The extracellular domain may be in a soluble form, or in the form of receptor-Ig chimeras known as receptor bodies or receptobodies. Preferred receptor bodies are divalent homodimers that contain the ligand-binding domain of a receptor followed by the hinge and Fc region of an Ig, such as Ig1. The Ig is preferably human Ig. Receptor bodies can be made by methods well known in the art. See, for example, Binder et al. 1999. *J. Neurosci.* 19:1424-1436 and Marcus et al. 1996. *Dev. Biol.* 180:786-789.

Alternatively, the molecule that binds specifically to the proneurotrophin may comprise an antibody hypervariable region that binds specifically to a proneurotrophin. The hypervariable region may further comprise an entire antibody variable region. The antibody variable region may further comprise an antibody constant region. Accordingly, the molecule that comprises an antibody hypervariable region may be any of the antibodies (including chimerized and humanized antibodies) and antibody fragments (including single chain antibodies) described below.

The molecules described above that bind specifically to proneurotrophins, such as the extracellular p75 receptors and molecules containing a hypervariable region described above, may be designed to bind to proneurotrophin monomers or to proneurotrophin multimers. The multimer may be any of the homomultimers and heteromultimers described above.

Administration of a cocktail of more than one molecule that inhibits the binding of a proneurotrophin to a p75 receptor is especially desirable. The molecules in the cocktail may comprise receptor bodies, antibodies, or a combination of receptor bodies and antibodies.

The cocktail may, for example, comprise one or more molecules that bind specifically to one, two, three, or all of the proneurotrophins. The cocktail may further comprise one or more molecules that binds specifically to the p75 receptor.

In another embodiment, the molecule that inhibits the binding of a proneurotrophin to a p75 receptor is a protease that cleaves the proneurotrophin to form a mature neurotrophin. The protease may be any of the proteases that cleave proneurotrophins, such as those described above.

The mammal in need of inhibiting apoptosis is generally a human who suffers from a condition associated with undesired apoptosis due to binding of a proneurotrophin to a p75 receptor. In this specification, a condition means any pathological state, such as, for example, a disease, an injury, or any other state that varies from a normal, proper, or healthy state. A condition associated with undesired apoptosis means any condition to which apoptosis contributes either primarily or secondarily, or either directly or indirectly.

The condition may involve normal expression in the mammal of the p75 receptor and the proneurotrophin. Usually, the condition involves overexpression of the proneurotrophin or of the p75 receptor in the cell undergoing apoptosis, or both.

Conditions suitable for treatment in accordance with this embodiment of the invention, may, for example, be the result of a nervous system injury or an environmental insult. The condition may, for example, be the result of hypoxic ischemia. Hypoxic ischemia may, for example, be caused by a stroke or by a heart attack.

The condition amenable to treatment by the present invention may be caused by a viral infection or a microbial infection. The microbial infection may be a bacterial infection. Some example of conditions caused by a viral infection or a microbial infection include meningitis, encephalitis, or abscesses.

Further examples of conditions that can be treated by the present invention include neurodegenerative and autoimmune disorders. Some examples of such disorders include Alzheimer's Disease, multiple sclerosis, familial dysautonomia, ataxia telangectasia, Charcot-Marie-Tooth disease, Adreno leuko dystrophy, spinal muscular atrophy, Friedriech's ataxia.

The condition may also be a condition that causes convulsions. An example of such a condition is epilepsy.

Antibodies

The present invention provides antibodies raised against the proteins, conjugates, and complexes described above. In this specification, an antibody is defined broadly as a protein that binds specifically to an epitope. Antibodies that bind specifically to an epitope may comprise an antibody hypervariable region. The hypervariable region may further comprise an entire antibody variable region. The antibody variable region may further comprise an antibody constant region. The molecule that comprises an antibody hypervariable region may be an antibody including a whole antibody, an antibody fragment, a chimerized antibody or a humanized antibody. The antibody may be polyclonal or monoclonal.

Suitable variable and hypervariable regions of non-human antibodies may be derived from antibodies produced by any non-human mammal in which monoclonal antibodies are made. Suitable examples of mammals other than humans include, for example, rabbits, rats, mice, horses, goats, or primates. Preferably, the antibodies are human antibodies. The antibodies may be produced in a transgenic mouse. An example of such a mouse is the so-called XenoMouse™ (Abgenix, Freemont, Calif.) described by Green, L L., "Antibody Engineering Via Genetic Engineering of the Mouse: XenoMouse Stains are a Vehicle for the Facile Generation of Therapeutic Human Monoclonal Antibodies," *J. Immunol. Methods*," 10; 231(1-2):11-23(1999).

Antibody fragments have binding characteristics that are the same as, or are comparable to, those of the whole antibody. Suitable fragments of the antibody include any fragment that comprises a sufficient portion of the hypervariable (i.e. complementary determining) region to bind specifically, and with sufficient affinity, to proneutrophins or p75.

The preferred fragments are single chain antibodies. Single chain antibodies are polypeptides that comprise at least the variable region of the heavy chain of the antibody and the variable region of the light chain, with or without an interconnecting linker.

A chimerized antibody comprises the variable region of a non-human antibody and the constant region of a human antibody. A humanized antibody comprises the hypervariable region (CDRs) of a non-human antibody. The variable region other than the hypervariable region, e.g. the framework variable region, and the constant region of a humanized antibody are those of a human antibody.

The antibodies and functional equivalents may be members of any class of immunoglobins, such as: IgG, IgM, IgA, IgD or IgE, and the subclass thereof. The functional equivalents may also be equivalents of combinations of any of the above classes and subclasses.

Modes of Administration

An effective amount of the protein of the invention, preferably in a pharmaceutical composition, may be administered to a human or an animal in need thereof by any of a number of well-known methods for use in any of the therapeutic methods described above. For example, the protein may be administered systemically or locally, for example by injection.

The systemic administration of a protein of the invention may be by intravenous, subcutaneous, intraperitoneal, intramuscular or intrathecal administration for treatment of a neural cell condition. Some examples of neural conditions include medulloblastoma, astrocytoma, a malignant dendrocyte or other cancerous condition of a neural cell of either the central nervous system (CNS) or the peripheral nervous system.

Alternatively, the protein of the invention may be applied topically in appropriate situations. Such situations include, exposed tissue to be treated. Some examples of exposed tissue include exposed metastatic tissue, as for example in a melanoma. Other exposed cancerous tissue includes cancerous breast tissue. The protein may also be delivered to the scalp of a person to inhibit hair loss due to p75-mediated hair follicle regression.

Alternatively, nucleic acid molecules of the invention may be incorporated into recombinant vectors suitable for use in gene therapy. The vector suitable for use in gene therapy may be any vector that comprises a nucleic acid sequence capable of expressing a protein of the invention in a mammal, especially a human, in need of such therapy. The suitable vector may be for example a viral vector, such as an adenovirus vector or an adeno-associated virus (AAV) vector. See for example: Ledley 1996. *Pharmaceutical Research* 13:1595-1614 and Verma et al. *Nature* 1997. 387:239-242.

In another alternative method, nucleic acid molecules of the invention may be administered as naked DNA. The naked DNA may be administered directly to the cells of an organ, tissue or anatomical region most affected by a disorder, condition or disease mediated by or involving cells expressing the p75 receptor. The expressed protein binds to the p75 receptor and induces apoptosis of the cell, thereby preventing any further pathological growth or proliferation of the cell.

An effective amount of a pharmaceutical composition of the invention is any amount that is effective to reduce, stabilize or ameliorate the progression of the condition to be treated. The relevant amount, usually expressed in mg/kg is determined by routine methods in clinical trials by those of skill in the art.

Screening for Conditions

In another embodiment, the invention relates to a method for screening a human patient for a condition associated with undesired apoptosis. The method comprises using a probe to determine the level of at least one proneurotrophin or a proneurotrophin-p75 conjugate in a biological sample.

The biological sample can be any sample taken from the human patient. The biological sample may, for example, be blood, urine, hair, cheek scrapings, semen, tissue biopsy, or saliva.

The proneurotrophin may be any pro-neurotrophin, e.g., pro-NGF, pro-BDNF, pro-NT-3, or pro-NT-4/5. In this specification, a proneurotrophin refers to an entire proneurotrophin, or to any of the proneurotrophin isoforms that results from cleavage of a pro-domain. See above.

The proneurotrophin-p75 conjugate is any proneurotrophin associated with the p75 receptor.

The method comprises determining whether elevated levels of proneurotrophin or proneurotrophin-p75 conjugates are present in the biological sample. The elevated levels indicate the existence of the suspected condition.

In this specification, an elevated level of proneurotrophins means a significantly greater level relative to a human who does not have the condition. A level is significantly greater if the level is at least about 10%, preferably at least about 25%, more preferably at least about 50%, even more preferably at least about 75%, and most preferably at least about 100% greater than a human who does not have the condition. It is not necessary to determine the level of proneurotrophins in a human who does not have the condition each time.

The probe recognizes at least one proneurotrophin or proneurotrophin-p75 conjugate. In this specification, a probe may, for example, be an antibody, a soluble p75 receptor or a receptor body as described elsewhere in this specification.

Screening Probes

The probe used to determine the level of at least one proneurotrophin or a proneurotrophin-p75 conjugate in a biological sample may be any molecule that binds specifically to a proneurotrophin or a conjugate. Some examples of probes that recognize proteins include antibodies, soluble receptors or receptor bodies as described elsewhere in this specification.

Alternatively, the probe may detect nucleic acid molecules that encode a proneurotrophin. The probe may be an oligonucleotide complementary to the nucleic acid sequence that encodes a proneurotrophin. These oligonucleotide probes are typically designed to detect proneurotrophin mRNA. It should be noted, however, that elevated levels of proneurotrophin mRNA suggest, but are not necessary indicative of, elevated levels of proneurotrophins. The possibility of cleavage of the proneurotrophins into mature neurotrophin must be considered.

The probes described above are optionally labelled in accordance with methods known in the art. The label may be a radioactive atom, an enzyme, or a chromophoric moiety.

Methods for labelling antibodies have been described, for example, by Hunter and Greenwood 1962. *Nature* 144:945 and by David et al. 1974. *Biochemistry* 13:1014-1021. Additional methods for labelling antibodies have been described in U.S. Pat. Nos. 3,940,475 and 3,645,090 and in Harlow, E. and Lane, D., Using Antibodies, A Laboratory Manual, Cold Spring Harbor Laboratory Press, Cold Spring Harbor, N.Y. (1999).

Methods for labelling oligonucleotide probes have been described, for example, by Leary et al., 1983. *Proc. Natl. Acad. Sci. USA* 80:4045; Renz and Kurz 1984. *Nucl. Acids Res.* 12:3435; Richardson and Gumport 1983. *Nucl. Acids Res.* 11:6167; Smith et al. 1985. *Nucl. Acids Res.* 13:2399; Meinkoth and Wahl, Anal. 1984. *Biochem.* 138:267; and Ausubel, F. M. et al. (Eds.) Current Protocols in Molecular Biology, John Wiley & Sons, Inc., New York, 1999.

The label may be radioactive. Some examples of useful radioactive labels include $^{32}P$, $^{125}I$, $^{131}I$, $^{35}S$, $^{14}C$, and $^{3}H$. Use of radioactive labels have been described in U. K. 2,034,323, U.S. Pat. No. 4,358,535, and U.S. Pat. No. 4,302,204.

Some examples of non-radioactive labels include enzymes, chromophores, atoms and molecules detectable by electron microscopy, and metal detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, in Ausubel, F. M. et al. (Eds.), Current Protocols in Molecular Biology, John Wiley & Sons, Inc., New York (1999), and by Rotman 1961. *Proc. Natl. Acad. Sci. USA* 47:1981-1991.

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

Kits

The invention further includes a kit useful in the method for screening a human patient for a condition associated with undesired apoptosis. The kit comprises a probe, and at least one of the following: a label, buffers, standards containing proneurotrophin and its conjugates, materials for developing calorimetric labels, materials for stopping calorimetric reactions, etc.

GENERAL METHODS

The proteins of the present invention may be prepared by methods that are well known in the art. One such method includes isolating or synthesizing DNA encoding the pro-domains and/or mature domains of the proteins of the invention, and producing the recombinant protein by expressing the DNA, optionally in a recombinant vector, in a suitable host cell.

The proteins of the invention may also be made synthetically, i.e. from individual amino acids, or semisynthetically, i.e. from oligopeptide units or a combination of oligopeptide units and individual amino acids. Suitable methods for synthesizing proteins are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997).

Nucleic acids encoding the proteins of the invention may also be synthesized in vitro. Suitable methods for synthesizing DNA are described by Caruthers et al. 1985. *Science* 230:281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992).

Nucleic acid molecules encoding the proneurotrophins of the invention may be designed or assembled from known nucleic acid sequences encoding neurotrophins or neurotrophin pro-domains or mature domains. The GenBank accession numbers for NGF, BDNF, NT-3, and NT-4/5 are M14805, M61176, M37763, and M86528, respectively. Alternatively, the nucleic acid sequence may be derived from a known proneurotrophin amino acid sequence using the genetic code, as is routine to those of skill in the art.

Databases and analytical software for the detection of proteins and nucleic acids having or encoding a particular sequence, pattern or motif are also readily available to the public, and provide useful protein or nucleic acid sequences for adaptation or modification for incorporation into the proneurotrophins of the present invention. For example the National Center for Biotechnology Information (NCBI) of the National Library of Medicine provides databases of protein and nucleic acid sequences and analytical and alignment software.

The proteins of the invention may be isolated from soluble or membrane fractions of preparations, such as for example cell-free lysates, conditioned media or other biological samples containing them by standard methods of protein isolation and purification. Some suitable methods include precipitation and liquid/chromatographic protocols such as for example, high performance liquid chromatography (HPLC), ion exchange, hydrophobic interaction chromatography, immunoprecipitation, lipid extraction, affinity chromatography and gel filtration to name but a few. See, for example, Guide to Protein Purification, Deutscher, M. P. (Ed.) Methods Enzymol., 182, Academic Press, Inc., New York (1990) and also Scopes, R. K. and Cantor, C. R. (Eds.), Protein Purification (3d), Springer-Verlag, New York (1994).

The methods, constructs and host cells suitable for production of desired proneurotrophin in standard small-scale culture systems, as well as large-scale production systems, include fermenter systems, hollow fiber culture systems, tumbler systems, and suspension culture systems to name but a few.

Methods and procedures for the manipulation of nucleic acids, polymerase chain reaction (PCR) methods for amplification of nucleic acids, construction of expression vectors, transformation of host cells, and the culture of transformed cells for the production of protein are known. These and many more relevant methods may be found in a variety of laboratory manuals, texts and guides. For a general guide, see, for instance, Sambrook & Russel, (2001) Molecular Cloning, Third edition, Cold Spring Harbor Press. Other useful sources include: Ausubel et al., 1992 Short Protocols in Molecular Biology, Second edition, John Wiley & Son; Gene Expression Technology, Methods in Enzymology Vol. 185 (ed. David Goeddel et al., Academic Press, Inc., London, 1991); Gene Structure and Expression, Second Edition, J. D. Hawkins (Cambridge University Press, London, 1991); PCR Protocols: A Guide to Methods and Applications (Innis, et al. 1990, Academic Press, San Diego, Calif.); Methods in Molecular Biology (Vol. 7), Gene Transfer and Expression Protocols, (ed. E. J. Murray, 1991, The Humana Press Inc., Clifton, N.J.).

Replication and Expression of Nucleic Acids Encoding Proteins of the Invention:

The nucleic acid encoding the proneurotrophins of the invention may be replicated and expressed in a suitable host cell. Suitable host cells include prokaryotic host cells and eukaryotic host cells. Suitable prokaryotic host cells include *E. coli* cells which are preferred. Suitable eukaryotic host cells include yeast cells, insect cells and mammalian cells, the latter being preferred.

Recombinant proneurotrophins are expressed in eukaryotic hosts in preference to prokaryotic hosts in cases where the protein must be post-transcriptionally modified. Examples of post-transcriptional modification include glycosylation, phosphorylation, disulfide bond formation, oligomerization and specific cleavage of the transcribed protein product.

Prokaryotic hosts do not perform certain post-transcriptional modifications of proneurotrophins of the invention, such as for instance glycosylation. For this reason expression in eukaryotic systems is preferred despite the higher costs associated with production of biologics in eukaryotic systems as compared with the costs of biologics produced in prokaryotic host systems.

Prokaryotic host systems are preferred for expression and production of recombinant proneurotrophins of the invention that do not require post-transcriptional modifications that are unique to eukaryotic systems and where the recombinant proneurotrophins are correctly folded or may be refolded in vitro.

Many standard well known cloning and expression and isolation/purification techniques that reflect the state of the art in recombinant DNA and protein methods are described in detail in Sambrook & Russel, *Molecular Cloning. A Laboratory Manual*, Third Edition, Cold Spring Harbor Laboratory Press, Cold Spring Harbor, N.Y. (2001). Techniques for expression of cloned genes in *E. coli* and in mammalian cells is described in detail in Chapters 15 and 16-17, respectively of the Sambrook & Russel Laboratory Manual (Id).

Site Directed Mutagenesis of Nucleic Acids Encoding the Proneurotrophins:

One technique for preparing nucleic acid molecules encoding the proteins of the invention is site directed mutagenesis. Procedures and kits for performing site directed mutagenesis are known in the art. Basically, the nucleic acid sequence of a target sequence within the nucleic acid sequence encoding a native (naturally occurring) proneurotrophin, a chimeric or non-natural proneurotrophin or neurotrophin or fragment of any of the above, may be specifically targeted at will to yield either a random sequence or a predetermined sequence. The available methods for such site directed mutagenesis include chemical mutagenesis of isolated restriction fragments encoding the target region or sequence, polymerase chain reaction (PCR) mediated mutagenesis of specific sequences and semisynthetic replacement of portions of a coding sequence. Several methods commonly used for site directed mutagenesis are described in detail in the Sambrook & Russel, A Laboratory Manual, at Chapter 13 (Id).

Antibodies

Methods for making monoclonal antibodies include, for example, the immunological method described by Kohler and Milstein 1975. *Nature* 256:495-497 and by Camplbell in "Monoclonal Antibody Technology, The Production and Characterization of Rodent and Human Hybridomas" in Burdon, et al., Eds, Laboratory Techniques in Biochemistry and Molecular Biology, Volume 13, Elsevier Science Publishers, Amsterdam (1985). The recombinant DNA method described by Huse, et al. 1989 *Science* 246:1275-1281 is also suitable.

Briefly, in order to produce monoclonal antibodies, a host mammal is inoculated with an antigen, such as p75 receptor, a proneurotrophin protein, or a proneurotrophin protein-p75 receptor conjugate, as described above, and then, optionally, boosted. In order to be useful, the receptor fragment must contain sufficient amino acid residues to define the epitope of the molecule being detected. If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule.

Spleens are collected from the inoculated mammals a few days after the final boost. Cell suspensions from the spleen are fused with a tumor cell. The resulting hybridoma cells that express the antibodies are isolated, grown and maintained in culture.

Suitable monoclonal antibodies as well as growth factor receptor tyrosine kinases for making them are also available from commercial sources, for example, from Upstate Biotechnology, Santa Cruz Biotechnology of Santa Cruz, Calif., Transduction Laboratories of Lexington, Ky., R&D Systems Inc of Minneapolis, Minn., and Dako Corporation of Carpinteria, Calif.

Methods for making chimeric and humanized antibodies are also known in the art. For example, methods for making chimeric antibodies include those described in U.S. patents by Boss (Celltech) and by Cabilly (Genentech). See U.S. Pat. Nos. 4,816,397 and 4,816,567, respectively. Methods for making humanized antibodies are described, for example, in Winter, U.S. Pat. No. 5,225,539.

Antibodies or antibody fragments can also be isolated from antibody phage libraries generated using techniques, for example, described in McCafferty et al. 1990. *Nature* 348: 552-554, using the antigen of interest to select for a suitable antibody or antibody fragment. Clackson et al. 1991. *Nature* 352: 624-628 and Marks et al. 1991. *J. Mol. Biol.* 222: 581-597 describe the isolation of murine and human antibodies, respectively, using phage libraries. Subsequent publications describe the production of high affinity (nM range) human antibodies by chain shuffling (Mark et al. 1992. *Bio/Technol.* 10: 779-783), as well as combinatorial infection and in vivo recombination as a strategy for constructing very large phage libraries (Waterhouse et al. 1993. *Nuc. Acids Res.* 21: 2265-2266). These techniques are viable alternatives to traditional monoclonal antibody hybridoma techniques for isolation of "monoclonal" antibodies (especially human antibodies).

The preferred method for the humanization of antibodies is called CDR-grafting. In CDR-grafting, the regions of a non-human mammalian antibodies, preferably a mouse antibody, that are directly involved in binding to antigen, the complementarity determining region or CDRs, are grafted into human variable regions to create "reshaped human" variable regions. These fully humanized variable regions are then joined to human constant regions to create complete "fully humanized" antibodies.

In order to create fully humanized antibodies that bind well to an antigen, it is advantageous to design the reshaped human variable regions carefully. The human variable regions into which the CDRs will be grafted should be carefully selected, and it is usually necessary to make a few amino acid changes at critical positions within the framework regions (FRs) of the human variable regions.

For example, the reshaped human variable regions may include up to ten amino acid changes in the FRs of the selected human light chain variable region, and as many as twelve amino acid changes in the FRs of the selected human heavy chain variable region. The DNA sequences coding for these reshaped human heavy and light chain variable region genes are joined to DNA sequences coding for the human heavy and light chain constant region genes, preferably γ1 and κ, respectively. The reshaped humanized antibody is then expressed in mammalian cells and its affinity for its target compared with that of the corresponding murine antibody and chimeric antibody.

Methods for selecting the residues of the humanized antibody to be substituted and for making the substitutions are well known in the art. See, for example, Co et al. 1993. *Nature* 351:501-502; Queen et al., 1989. *Proc. Natl. Acad. Sci.* 86: 10029-1003 and Rodrigues et al. 1992. *Int. J. Cancer*, Supplement 7: 45-50. A method for humanizing and reshaping the 225 anti-EGFR monoclonal antibody described by Goldstein et al. in PCT application WO 96/40210. This method can be adapted to humanizing and reshaping antibodies against other growth factor receptor tyrosine kinases.

Methods for making single chain antibodies are also known in the art. Such methods include screening phage libraries transfected with immunoglobulin genes described in U.S. Pat. No. 5,565,332; U.S. Pat. No. 5,5837,242; U.S. Pat. No. 5,855,885; U.S. Pat. No. 5,885,793; and U.S. Pat. No. 5,969,108. Another method includes the use of a computer-based system for designing linker peptides for converting two separate polypeptide chains into a single chain antibody described in U.S. Pat. No. 4,946,778; U.S. Pat. No. 5,260,203; U.S. Pat. No. 5,455,030; and U.S. Pat. No. 5,518,889.

Other methods for producing antibodies described above are disclosed by Wels et al. in European patent application EP 502 812 and *Int. J. Cancer* 60:137-144 (1995); PCT Application WO 93/21319; European Patent Application 239 400, PCT Application WO 89/09622; European Patent Application 338 745; U.S. Pat. No. 5,658,570; U.S. Pat. No. 5,693,780; and European Patent Application EP 332 424.

Labels

The labels may be conjugated to probes by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the antibodies or nucleotides by means of coupling agents, such as dialdehydes, carbodiimides, dimaleimides, and the like.

The label may also be conjugated to the probe by means of a ligand attached to the probe by a method described above and a receptor for that ligand attached to the label. Any of the known ligand-receptor combinations is suitable. Some suitable ligand-receptor pairs include, for example, biotin-avadin or -streptavadin, and antibody-antigen. The biotin-avidin combination is preferred.

The probe may be an antibody, preferably a monoclonal antibody. The antibodies may be prepared as described above.

Assays

The antibodies described above can be used in assays to detect the presence of the proteins, conjugates, and complexes. Such assays can be performed using known formats such as immunohistochemistry/immunocytochemistry of tissues (U.S. Pat. No. 5,846,749) and ELISA (Current Protocols in Immunology, Wiley Intersciences, New York, 1999).

Assays for detecting the presence of proteins with antibodies have been previously described, and follow known formats, such as standard blot and ELISA formats. These formats are normally based on incubating an antibody with a sample suspected of containing the protein and detecting the presence of a complex between the antibody and the protein. The antibody is labelled either before, during, or after the incubation step. The protein is preferably immobilized prior to detection. Immobilization may be accomplished by directly binding the protein to a solid surface, such as a microtiter well, or by binding the protein to immobilized antibodies.

In a preferred embodiment, a protein is immobilized on a solid support through an immobilized first antibody specific for the protein. The immobilized first antibody is incubated with a sample suspected of containing the protein. If present, the protein binds to the first antibody.

A second antibody, also specific for the protein, binds to the immobilized protein. The second antibody may be labelled by methods known in the art. Non-immobilized materials are washed away, and the presence of immobilized label indicates the presence of the protein. This and other immunoassays are described by David, et al. in U.S. Pat. No. 4,376,110 assigned to Hybritech, Inc., La Jolla, Calif.; by Coligan, J. E, et al. (Eds.), Current Protocols in Immunology, Wiley Intersciences, New York, 1999); and by Harlow, E. and Lane, D., Using Antibodies, A Laboratory Manual, Cold Spring Harbor Laboratory Press, Cold Spring Harbor, N.Y. (1999).

Immunoassays may involve one step or two steps. In a one-step assay, the target molecule, if it is present, is immobilized and incubated with a labelled antibody. The labelled antibody binds to the immobilized target molecule. After washing to remove unbound molecules, the sample is assayed for the presence of the label.

In a two-step assay, immobilized target molecule is incubated with an unlabelled first antibody. The target molecule-antibody complex, if present, is then bound to a second, labelled antibody that is specific for the unlabelled antibody. The sample is washed and assayed for the presence of the label, as described above.

The immunometric assays described above include simultaneous sandwich, forward sandwich, and reverse sandwich immunoassays. These terms are well known to those skilled in the art.

In each of the above immunoassays, the sample containing antigen, solid phase immunoabsorbent with immobilized antibody and labeled soluble antibody are incubated under conditions and for a period of time sufficient to allow antigen to bind to the immobilized antibodies and to the soluble antibodies. In general, it is desirable to provide incubation conditions sufficient to bind as much antigen as possible, since this maximizes the binding of labeled antibody to the solid phase, thereby increasing the signal. The specific concentrations of labeled and immobilized antibodies, the temperature and time of incubation, as well as other such assay conditions, can be varied, depending upon various factors including the concentration of antigen in the sample, the nature of the sample and the like. Those skilled in the art will be able to determine operative and optimal assay conditions for each determination by employing routine experimentation.

There are many solid phase immunoabsorbents which have been employed and which can be used in the present invention. Well known immunoabsorbents include beads formed from glass, polystyrene, polypropylene, dextran, nylon, and other material; and tubes formed from or coated with such materials, and the like. The immobilized antibodies may be covalently or physically bound to the solid phase immunoabsorbent, by techniques such as covalent bonding via an amide or ester linkage or by absorption.

EXAMPLES

The scope of the compositions and methods of the present invention may be better understood by those of skill in the art by reference to the following specific examples:

Example 1

Expression and Isolation of His-Tagged Cleavage Resistant NGF

Figure 6:
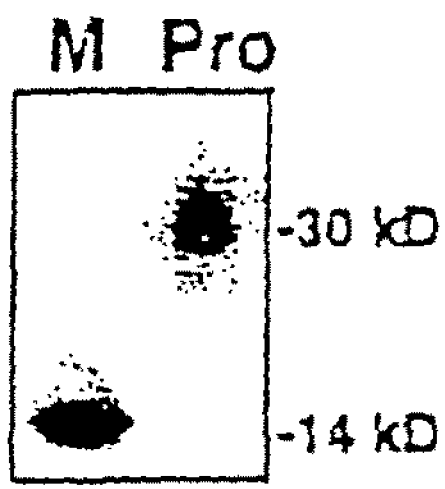
FIG. 6: Purification of His-tagged native (cleaved) NGF, and a His-tagged point mutant (proform) NGF. Media from 293 cells stably expressing constructs of native or mutant NGF incorporating a His tag at the carboxy-terminus, or the vector alone were purified using Ni-column chromatography. Proteins eluted with imidazole were subjected to SDS-PAGE and Western blotted with anti-His antisera. Mature (M), and cleavage resistant proform (Pro) are indicated.

To assess the biological activity of proneurotrophins, NGF cDNAs were stably expressed in 293 cells, to generate microgram quantities of His-tagged native NGF, which is completely processed to the mature form of 13.5 kDa in 293 media and a His-tagged point mutant of pro-NGF, in which the K-R cleavage site at 120,121 has been mutated to A-A. This renders the molecule cleavage resistant, and results in a proform of NGF of 30 kDa isolated from 293 cell media (FIG. 6).

Example 2

Figure 7:
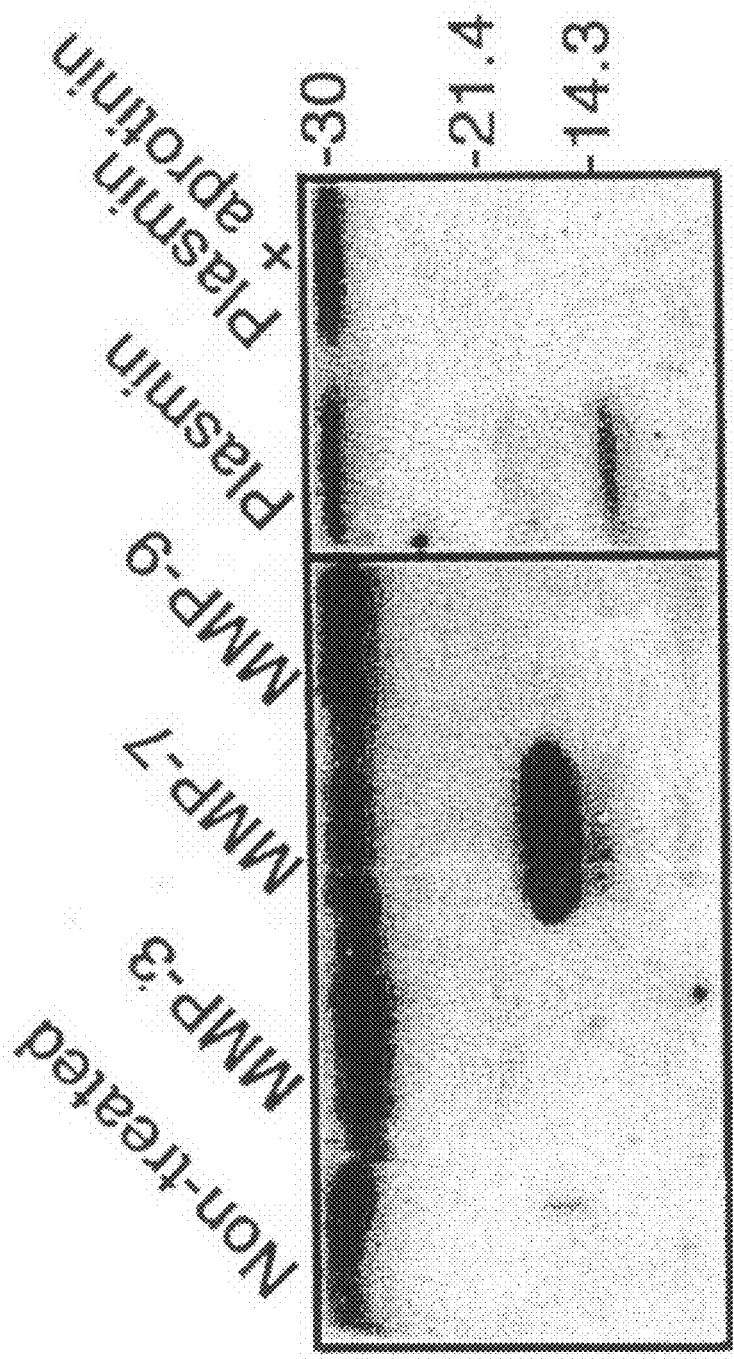
FIG. 7. Purified pro-NGF (0.8 μg/ml) was incubated with the indicated proteinases with or without inhibitors and proteolytic products detected by Western blot analysis with anti-NGF antibody.

Identification of Proteases for Cleavage of a Neurotrophin, NGF, to its Mature Form To determine if plasmin, MMP-3, MMP-7 or MMP-9 can cleave secreted pro-NGF, purified proNGF was incubated with the proteinases with or without inhibitors. Pro-NGF was cleaved by plasmin to a 13 kD form. Inhibition of plasmin activity upon addition of aprotinin inhibited cleavage of pro-NGF. In addition, incubation of the pro-NGF with MMP-7 but not MMP-2, -3, or -9 resulted in cleavage of the 30 kD proform of NGF to the 17 kD form (FIG. 7).

Example 3

Assays of the Biological Activity of Cleavage Resistant NGF

These proteins have been highly purified and utilized in (1) binding assays, (2) apoptosis assays using cells expressing only p75 and (3) assays of trk activity, using trk-mediated autophosphorylation in dose-response studies and PC12 cell neuritogenesis.

The cleavage resistant proform of NGF binds with higher affinity than the cleaved mature form of NGF to the p75 receptor. Competition binding assays were performed to determine the affinity of interaction of the uncleaved proform to p75 or to trk A. Commercially purchased, predominantly mature NGF (Enzo Products for Science, Farmingdale, N.Y.) was radiolabeled and incubated with cells expressing only p75, in the presence or absence of increasing concentrations of either unlabeled cleaved NGF, or of unlabeled cleavage resistant pro-NGF. As shown in FIG. 8A, the $IC_{50}$ of cleaved NGF is 1.0 nM, consistent with prior reports. However, the $IC_{50}$ of the uncleaved proform is 0.2 nM, indicating that the uncleaved proform is approximately 5 times as effective in binding p75 as is cleaved NGF. In contrast, competition curves generated using 293 cells expressing only trk A (FIG. 8B), demonstrate that the $IC_{50}$ of mature NGF is 1.2 nM, and the cleavage resistant pro-NGF is greater than 5 nM. Thus, the cleavage resistant pro-NGF proform binds less effectively to trk A.

Example 4

The Cleavage Resistant Pro-NGF is More Effective than Mature NGF in Inducing Apoptosis of Cells Expressing Only p75

To determine if the enhanced binding of cleavage resistant pro-NGF to p75 resulted in increased p75-mediated apoptosis, a vascular smooth muscle cell line expressing p75 (but not trk receptors) which exhibits dose dependent apoptosis upon NGF addition was used in the following experiments. Cells were exposed to His tagged mature NGF or His tagged uncleaved NGF purified from 293 cell media (see FIG. 6) or as controls, purified media from cells transfected with vector or commercial (predominantly mature) NGF. Apoptosis was assessed by TUNEL analysis at 18 h post-treatment (See FIG. 9A). Less than 5% of the control cells were TUNEL-positive. Commercial, mature NGF induced 20% TUNEL positive cells at 2 nM, consistent with prior reports, and purified media from vector transfected cells did not induce TUNEL positivity. Mature His-tagged NGF appeared similar to commercial NGF in inducing TUNEL positivity whereas the cleavage resistant pro-NGF was at least 10 times as effective in inducing apoptosis, with 18% TUNEL positive cells following treatment with 0.1 nM cleavage resistant pro-NGF. This result is in good agreement with the binding data (FIG. 8A), and indicates that occupancy of only 30% of the p75 receptors with uncleaved NGF can initiate apoptosis.

Example 5

The Cleavage Resistant Pro-NGF is Less Effective in Activating Trk

To determine the relative activities of mature NGF and cleavage resistant pro-NGF in activating trk-mediated cellular responses, the autophosphorylation of trk A in dose-response studies was examined. Mature NGF and commercial NGF induced trk A autophosphorylation at a concentration of 0.2 nM. However, cleavage resistant pro-NGF did not induce trk A phosphorylation even at concentrations of 1 nM. This result is in good agreement with the observed reduction in trkA binding (see FIG. 8A).

Example 6

Figure 9:
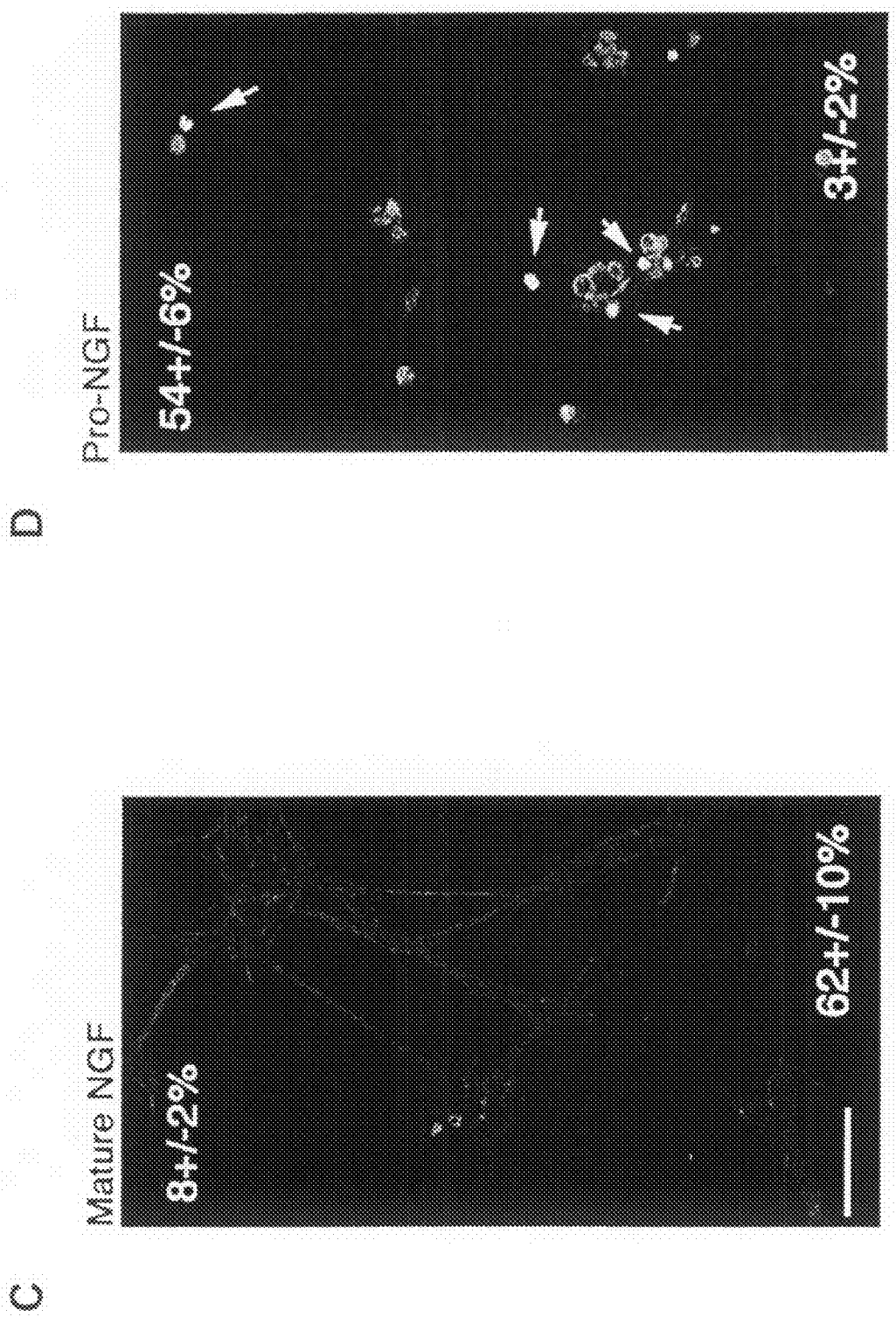
FIG. 9: Distinct biological activities are elicited by cleaved and uncleaved NGF. (A) Induction of apoptosis by NGF and pro-NGF using p75 expressing smooth muscle cells. Cells expressing p75 (p75Ts-Tag-SMC) were cultured at 39.5° C. for 96 h to permit differentiation, then incubated with the indicated concentration of commercial NGF (open circles), His-tagged NGF (filled circles), His-tagged pro-NGF (filled squares), or column eluates from vector transfected cells (open squares). After 18 h, cells were subjected to TUNEL analysis and were stained with DAPI to visualize nuclei. At least 400 cells/condition were counted, and the result is representative of two independent experiments with different preparations of NGFs. (B) Effects of mature NGF and pro-NGF on PC12 cell neuritogenesis. trk A-overexpressing PC12 cells were treated with His-tagged cleaved NGF, His-tagged uncleaved NGF, commercial NGF or column eluates from vector-transfected controls for 48 h in serum free media. Cells were scored for neurite processes greater than one cell body in length. (C and D) Effects of mature NGF (C) and pro-NGF (D) on superior cervical ganglia neurons. Superior cervical neurons were treated with 0.4 nM of mature or pro-NGF for 36 h and fixed. Cells were double-labeled for Trk immunoreactivity and TUNEL positivity with DAPI staining for the nuclei. The percentage of neurite expressing cells (white typeface) and apoptotic cells (green typeface) is indicated. Cells treated with diluent alone yielded 30±10% apoptosis. Scale bar, 30 μm. At least 200 cells per condition were scored, and results are representative of three independent experiments using different preparations of NGFs.

The Cleavage Resistant Pro-NGF is Less Effective than Mature NGF in Mediating Trk Dependent Neuritogenesis To determine the relative activities of uncleaved and cleaved NGF in activating trk receptors, PC12 cells were utilized in neuritogenesis assays (FIG. 9B). Treatment of these cells with His-tagged mature, or commercial (predominantly mature) NGF, induced neurites at 0.1 nM concentrations. However, no neurite outgrowth was observed in cells that were treated with the cleavage resistant pro-NGF even at concentrations up to 2 nM. PC12 cells treated with purified media from cells transfected with vector displayed no neurite outgrowth. As a control, TUNEL analysis was performed on replicate cultures; less than 2% cell death were observed under all conditions tested.

Example 7

Pro-NGF Induces Cell Death in Neurons Coexpressing p75 and Trk A

Superior cervical ganglia neurons coexpress both p75 and trk A receptors. The neurons were treated with either mature NGF or pro-NGF. Treatment of superior cervical ganglia neurons with pro-NGF resulted in cell death (FIG. 9D). Treatment with mature NGF resulted in very little cell death (FIG. 9C).

Example 8

Expression of BDNF in Eukaryotic Cells

Figure 10:
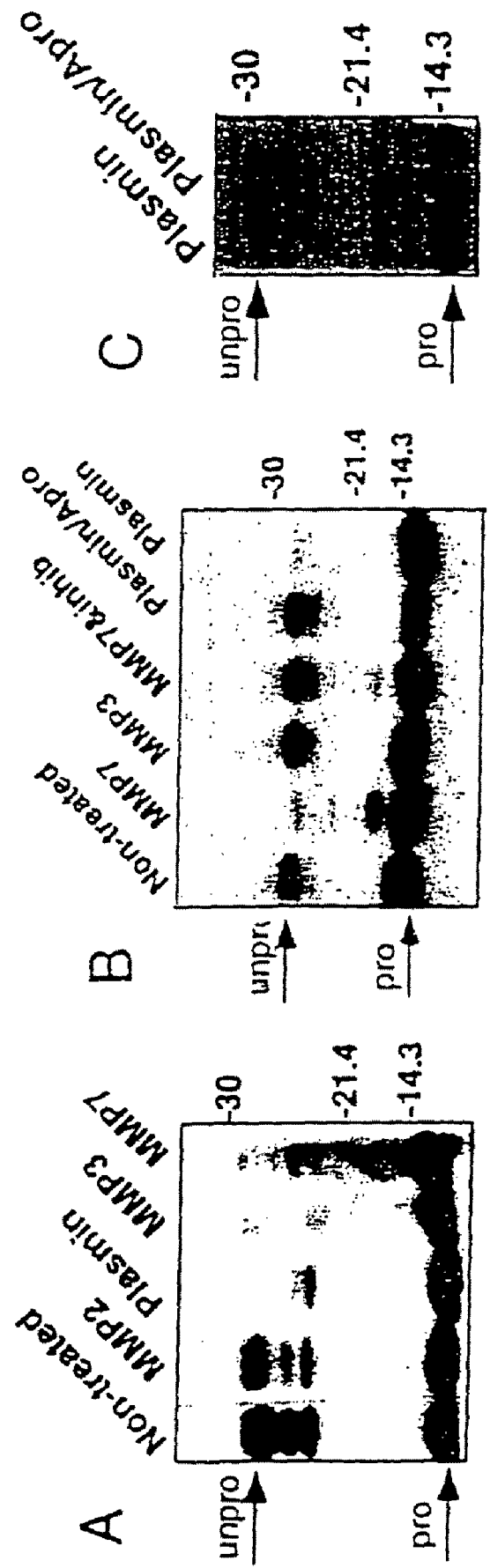
FIG. 10: Proteolytic cleavage of BDNF from Ad-infected (A) 293T or (B) murine endothelial cells by plasmin and MMPs in the supernatants of Ad-infected cells. Inhibition of cleavage by plasmin using the inhibitor aprotinin or peptide inhibitor of MMPs. (C) BDNF expressing endothelial cells were incubated with plasmin or plasmin plus aprotinin. Unpro=unprocessed form; Pro=processed form.

Recombinant adenovirus may be utilized to express rat BDNF in 293T cells, or endothelial cells, an in vivo source of BDNF in the CNS and extraneuronal sites (Donovan, M. J., et al. 2000. Development 127:4531-4540; Leventhal, C., et al. 1999. Mol. Cell. Neurosci. 13:450-464). Forty-eight hours following cell infection, BDNF released into the culture media is detected by Western blot using an antibody specific for epitopes in the mature BDNF protein. Immunoreactive proteins of 30 kDa, 28 kDa, 24 kDa and 14 kDa are secreted into the media of 293 cells (FIG. 10A), and products of 28 kDa and 14 kDa are detectable from media of endothelial cells (FIG. 10B). Approximately 1.1 microgram/ml/24 h is secreted by infected cells, as determined by ELISA analysis, using recombinant BDNF as a standard.

Example 9

Identification of Proteases that are Essential for the Cleavage of a Neurotrophin, BDNF, to its Mature Form To determine if plasmin, MMP-3 or MMP-7 can cleave secreted BDNF, recombinant proteases were added to the media from adenoviral infected cells, and all these enzymes led to a reduction in the proforms of 30 kDa in 293 cells while MMP-2 was without effect (FIG. 10A). In endothelial media, only plasmin and MMP-7 appeared to cleave the large proform (FIG. 10B), perhaps reflecting differences in TIMP by endothelial cells as compared to 293 cells. Treatment of the media with recombinant MMP7 resulted in a reduction in the high molecular weight isoforms of 30 kDa or 28 kDa, and the generation of a novel form of approximately 17 kDa. The specificity of proteolysis by plasmin was confirmed by concomitant incubation with its inhibitor aprotinin, or the inclusion of an MMP-7 inhibitory peptide, which in each case inhibited the cleavage of a proform of BDNF.

To confirm that cleavage of proforms to mature BDNF occurs extracellularly, adenovirally infected cultures were incubated with plasmin, or a combination of plasmin plus aprotinin in the media for 48 hours prior to media collection. As shown in FIG. 10C, inhibition of plasmin activity upon addition of aprotinin reduced the cleavage of high molecular weight forms of BDNF, strongly suggesting that these higher molecular weight proforms are released from cells, and that plasmin cleavage occurs on the surface of intact cells.

Recombinant native murine NGF, as well as NGF with the R-R (−1, 0) mutant to A-A constructs have been prepared. Because the NGF start site does not conform to a Kozak consensus sequence, impairing efficient translation, the 15 bases upstream of the NGF ATG (−14 to 0) was substituted for (−14 to 0) of the NT-3 sequence, yielding a cDNA which utilizes the NT-3 Kozak site and the entire NGF coding sequence. With this construct, secreted NGF from transiently transfected 293 cells are obtained at significant levels (0.5 micrograms/100 mm$^2$ plate/24 hr)., The dibasic site (R-R) at (−1, 0) is mutated to A-A using a PCR based Quik-Change method, and likewise the dibasic site at the carboxyl-terminus (+118,+119) is mutated to prevent cleavage of the His tag. Mutated cDNAs are subjected to complete bidirectional sequencing, and subcloned into the pcDNA expression vector.

Both native His-tagged NGF and the (R-R) to (A-A) mutant have been isolated from the media of transiently transfected 293 cells using a Ni-Sepharose column. The His-tagged NGF, migrating at 14 kDa, displays no loss of biological activity as compared to commercial recombinant NGF, as assessed in PC12 neurite outgrowth assays. These results suggest that the C-terminal His-tag does not impair NGF binding to trk A, and is consistent with the crystallographic structure of the NGF/trk A complex, in which the C-terminal tail of NGF is not involved in NGF/trk A interfaces.

Example 10

Binding Studies with Cleavage Resistant Neurotrophins

Binding of cleavage resistant neurotrophins may be compared to native, mature NGF or BDNF to either p75, or their cognate trk receptors, using competition displacement studies.

The methodology for these studies is well described in recent publications (Rydén, M., et al. 1997. The Journal of Biological Chemistry 272:16322-16328). In brief, mature-His tagged or cleavage resistant-His tagged neurotrophin is radioiodinated to a specific activity of approximately 2800 dpm/fmole. Iodinations using 0.5 µg of neurotrophin routinely generate material for approximately 20 binding studies (Hempstead, B. L., et al. 1991. Nature 350:678-683). For competition analysis, 3T3 cells stably expressing trk A or trk B, or 3T3 cells stably expressing p75 (lines with 75,000 receptors/cell are available, see for example Mahadeo, D., et al. 1994 J. Biol. Chem. 269:6884-91) are incubated concomitantly with radioiodinated neurotrophin (at $10^{-9}$ M) and unlabeled native neurotrophin at increasing concentrations ($10^{-10}$ to $10^{-8}$ M) at 4° C. for 2 hours. Bound ligand is separated from free by centrifugation of cells as described (Ryden M., et al., EMBO J. 14: 1979-90) and the binding properties of each mutant neurotrophin is determined by calculating the IC$_{50}$ (the concentration of inhibitor which reduces binding by 50%).

Example 11

Tissue Expression of Neurotrophins

Figure 11:
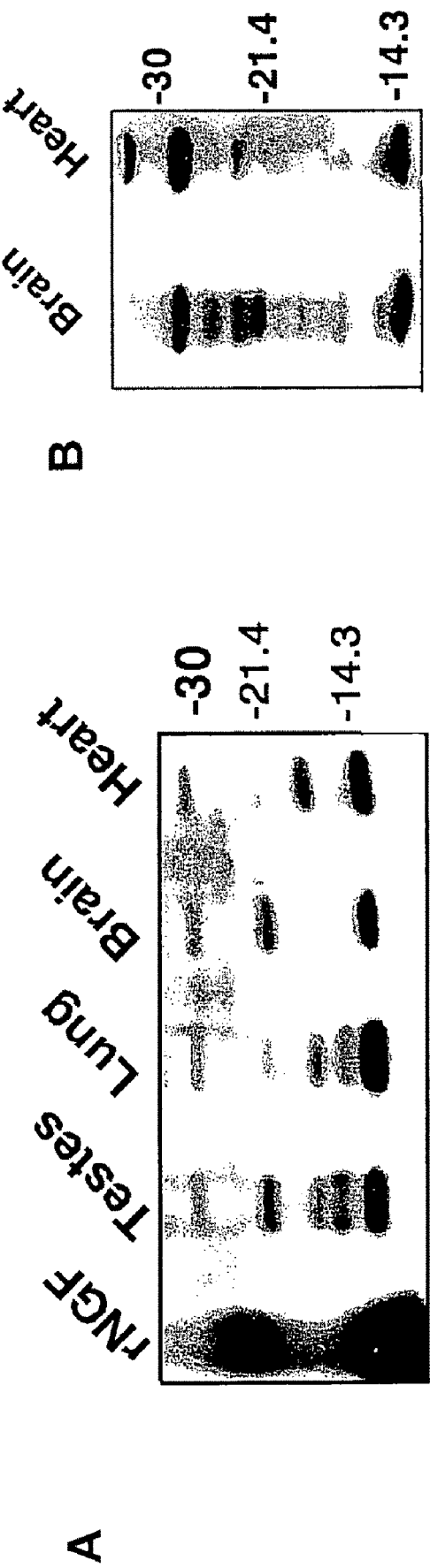
FIG. 11. Tissue expression of neurotrophins. Western blot analysis of adult mouse tissue (50 g) subjected to reduction with dithiotheitol and alkylation with iodoacetamide to inhibit neurotrophin dimerization, were proved with antiserum specific for epitopes in the mature forms of NGF (A) or BDNF (B).

To determine the tissue expression of neurotrophins, adult mouse tissues were probed with antibodies that recognize the mature region of NGF or BNDF. In adult tissues, both mature (approximately 14 kD) and larger preproisoforms of both NGF and BDNF were detected (FIGS. 11A and B). The larger isoforms of NGF were also present in the commercial preparations of recombinant NGF. In the tissue extracts from adult mice, the detectable neurotrophin proteins ranged in size from 14 kD (mature form) to approximately 30 kD (size of the unprocessed, preproform). Intermediately sized proteins of 16, 18, and 22 kD for NGF and 18, 22, 28, and 30 kD for BDNF were also detected. The data demonstrates that proforms of NGF and BDNF are expressed at significant levels in many adult tissues. In addition, the data shows that tissues process NGF and BDNF differently.

Example 12

Antibodies Specific to the Pro-Domain of Pro-BDNF and Pro-NGF

Figure 12:
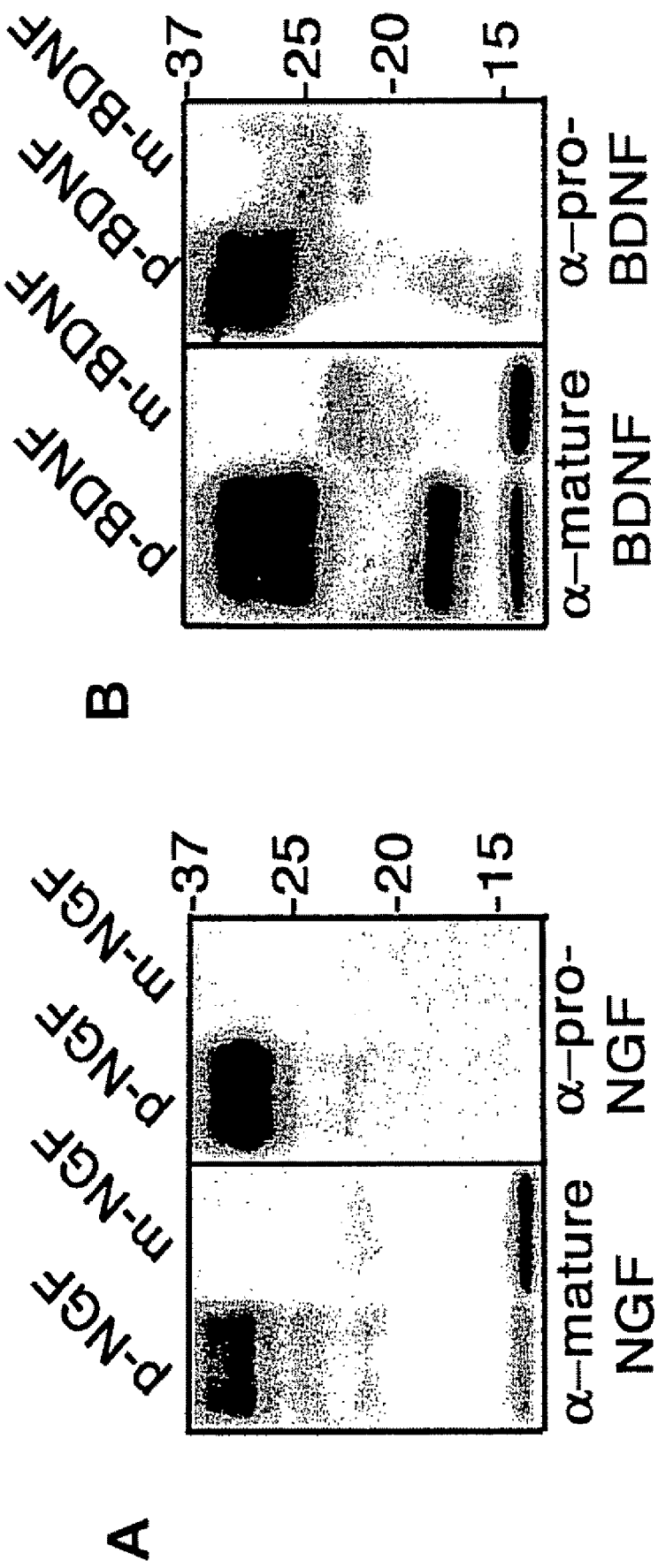
FIG. 12. Western blot analysis of pro-NGF and pro-BDNF specific antibodies. Recombinant human mature BDNF, or mature mouse NGF, and recombinant cleavage resistant mouse pro-BDNF or recombinant mouse pro-NGF were separated by SDS-polyacrylamide gel electrophoresis. Pro-BDNF was generated by infecting 293 cells with a recombinant adenovirus encoding murine BDNF (SEQ. ID. NO: 15) which had been mutated at positions 434-439. Blots were probed with the indicated antisera to NGF (A) or BDNF (B). Apparent molecular masses are indicated.

The antibodies available to date have been generated to the mature domain of the neurotrophins, thus recognizing both mature and pro-forms. To develop specific antibodies that are specific for the pro-domain of BDNF and NGF, and that can distinguish pro- from mature forms of BDNF and NGF, GST-fusion proteins encoding amino acids 20-80 of BDNF or amino acids 20-82 of NGF were generated and used as immunogens in chickens (for BDNF) or rabbits (for NGF). The antisera was affinity purified using columns of the immunogen. The antisera to pro-NGF detects pro-NGF, but not mature NGF (FIG. 12A). The antisera to pro-BDNF detects pro-BDNF, but not mature BDNF (FIG. 12B).

Example 13

Pro-BDNF and Pro-NGF are Expressed in Lesions of Vascular Injury

The expression and localization of the pro-forms and mature forms of NGF and BDNF in murine models of vascular injury was assessed. In lesions from Western-diet fed ApoE (−/−) animals, both the pro- and mature NGF were more highly expressed in the plaque, as compared to the medial smooth muscle cell layer. A similar pattern was detected with BDNF antisera. Both the pro- and mature BDNF immunoreactivity were preferentially expressed in the lesions, as compared to the media, with further restriction of the pro-BDNF immunoreactivity to the cellular area near the vessel lumen. Mature, but not pro-BDNF is expressed by endothelial cells in uninjured, normal adventitial vessels.

Example 14

Expression of Pro- and Mature NGF and BDNF in Human Atherosclerotic Lesions

Figure 13:
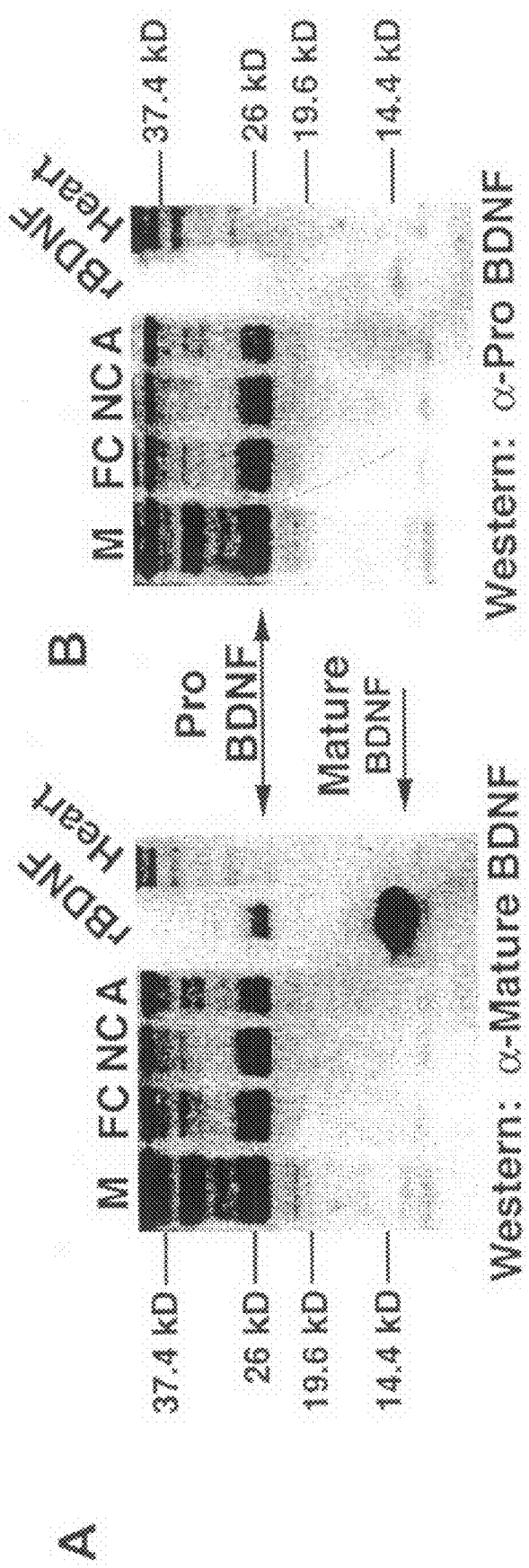
FIG. 13. Western blot analysis of human carotid atherectomy specimens to detect neurotrophin isoforms: (A) Mature BDNF, (B) Pro-BDNF, (C) Mature NGF, and (D) Pro-NGF. Atherectomy specimens in toto (A), or those subjected to microdissection of the media (M), fibrous cap (FC), necrotic core (NC) were solubilized in detergent, and 70 µg aliquots of total protein separated by SDS PAGE, along with recombinant BDNF (rBDNF), murine adult heart extracts (Heart), purified cleavage resistant proNGF (proNGF) or murine mature NGF (NGF). The schematic diagram of the medial, fibrous plaque and necrotic core regions are indicated (E).
Figure 13:
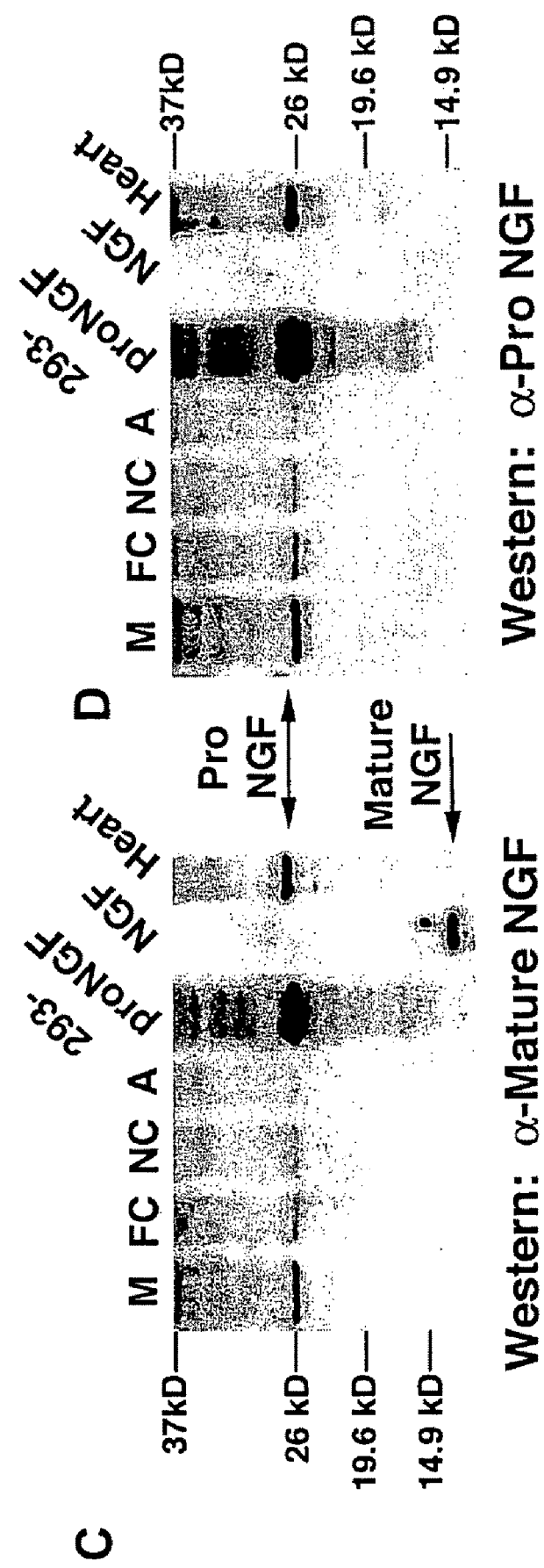
Figure 13E:
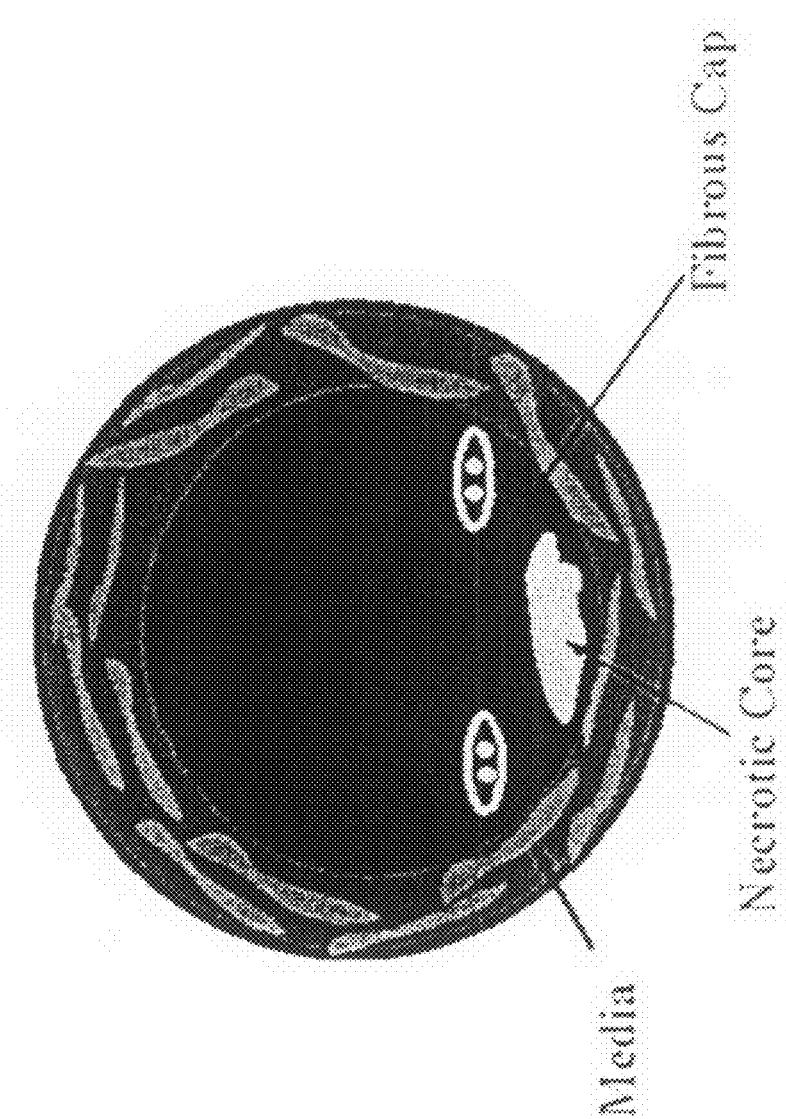

To assess the expression of NGF and BDNF isoforms in human atherosclerotic lesions, advanced plaques obtained at endarterectomy of symptomatic carotid lesions were microscopically dissected. Tissues from the media, the necrotic core, or the fibrous cap were subjected to detergent solubilization. In parallel, tissue consisting of all three regions was solubilized without dissection. Immunoreactive bands at approximately 26 kD were detected in extracts from human atherosclerotic lesions when probed with antisera to the mature (FIG. 13A) or pro-domain specific BDNF (FIG. 13B). The molecular size, and immunoreactivity with pro-domain specific antisera is consistent with pro-BDNF. Similarly, Western blot analysis using mature NGF (FIG. 13C) and pro-BDNF (FIG. 13D) antisera detected a 26-28 kd species, which is consistent with pro-BDNF.

Example 15

Construction of a Replication Deficient Recombinant Adenovirus Based on Human Serotype 5

Neurotrophin cDNA is subcloned in the shuttle vector (p.shuttle.cmv) and cotransformed with pAdEasy (containing the adenovirus serotype 5 genome with deletions in E1-E3 regions) in bacteria. Homologous recombination replaces the E1 region of pAdEasy with the mutant neurotrophin cDNA and plasmids are isolated and screened for neurotrophin cDNA expression by PCR. Recombinant plasmid is transfected into 293 cells and viral particles are plaque purified. High titer stocks are prepared, using cesium chloride ultracentrifugation, and the viral concentration determined by plaque titration. Viral stocks are used to infect 293 cells at a MOI of 10 for 90 min, and neurotrophins purified from the media 2 days after infection using Ni chromatography as outlined above. Purity is assessed by silver stain; if additional purification is necessary to obtain preparations which are >95% pure, reverse phase chromatography is performed (Ryden, M., et al. 1995. EMBO J 14:1979-90).

Equilibrium binding studies are performed using the radioiodinated cleavage resistant mutant neurotrophin, with or without excess unlabeled mutant neurotrophin to assess specific binding (see Hempstead, B. L., et al. 1991. Nature 350: 678-683. and Mahadeo, D., et al. 1994. J. Biol. Chem. 269: 6884-91 for detailed methods). In brief, samples of increasing concentrations ($10^{-11}$ to $10^{-8}$ M) of the radioiodinated ligand is incubated with a constant number of 3T3 cells expressing either p75 or trk, at 4° C. for 2 hours. Bound ligand is separated from free by cell centrifugation, and pellets counted for associated radioactivity. Specific binding is generally greater that 75% of total binding. Scatchard plot analysis allows calculations of the affinity of interaction ($K_D$), as well as assessment of a single or multiple affinity binding sites.

Example 16

Receptor Activation by Neurotrophin Mutants

Trk activation is assessed in 3T3 cells expressing either trk A, trk B or trk C. For a dose response analysis, cells are treated with mature or cleavage resistant neurotrophins ($10^{-10}$ to $10^{-8}$ M). The rapid trk autophosphorylation (within 5 min), and phorphorylation and activation of well defined downstream signaling events such as MAP kinase and PI-3 kinase may be assessed by standard methods. From cells lysed in detergent buffer containing phosphatase and protease inhibitors, trk, or MAP kinase are immunoprecipitated and Western blotted using anti-PY antisera. MAP and PI-3 kinase kinase activation is quantified using immunoprecipitation (IP)-kinase assays, as has been described (Hempstead, B. L., et al. 1992. Neuron 9:883-896). The dose response analysis of ligand binding to trk may then be compared with the induction of trk activation.

Parallel studies may be performed with cells expressing only p75 receptors. The quantitative assessment of p75 receptor activation is not as straightforward, as many of the downstream signaling cascades activated by p75 require that the cells are concomitantly stressed (JNK activation, and NFκB activation) or elicit only modest enhancements (ceramide production) following neurotrophin addition (reviewed in Casaccia-Bonnefil, P., et al. 1999: "The Functional Roles of Glial Cells in Health and Disease." Plenum, N.Y. However, ligand induced p75-TRAF6 interaction is suitable for quantitative analysis. See Khursigara, G., et al. 1999. J Biol Chem 274:2597-600.

293 cells transiently expressing p75 and TRAF6 may be used for dose-response analysis, by incubating cells with mature or cleavage resistant neurotrophin ($10^{-10}$ to $10^{-8}$ M) for 5 minutes. Cells are then lysed, and a co-immunoprecipitation analysis of p75:TRAF6 complexes performed by immunoprecipitating with anti-p75 and probing for FLAGtagged TRAF6. Based on prior studies (Kursigawa and Chao, 1999), the neurotrophins must be present at concentrations of 4 nM or greater to induce complex formation between p75 and TRAF6. Cleavage resistant neurotrophins which have enhanced binding affinity for p75 may be identified in this way.

Cleavage resistant mutants may also be characterized for binding and activation of p75 and trks independently and in cells which co-express both receptors. Using available 293 cell lines and PC12 cell lines which co-express either trk A/p75 or trk B/p75 at approximately 75,000 trk and 75,000 p75 receptors per cell, the dose responsiveness of these cells to mature and cleavage resistant neurotrophins may be determined using trk autophosphorylation, MAP kinase activation and PI-3 kinase activation as trk signaling predominates when both receptors are expressed (Casaccia-Bonnefil, P., et al. 1999. The Functional Roles of Glial Cells in Health and Disease. Plenum, N.Y.).

Example 17

Biological Effects of Cleavage Resistant Neurotrophins

To assess the relative potency of native and cleavage resistant neurotrophins to activate trk receptors, trk A or trk B expressing fibroblasts are used in cell proliferation analysis. These assays do not require p75 expression, and are highly quantitative (See Arevalo, J. C., et al. 2000. Mol Cell Biol 20:5908-16), thus allowing activation by native neurotrophins to be distinguished from those mutants which may exhibit reduced activity. In brief, cells cultured in serum free media are treated with or without increasing concentrations of native or cleavage resistant neurotrophins for 24 hr, then pulsed with $^3$H-thymidine. Thymidine incorporation, as a measurement of cell proliferation, is quantitated in a filter binding assay (Arevalo, J. C., id.). The cleavage resistant neurotrophins exhibit reduced proliferation when they are impaired in trk binding.

To assess p75 activation, two model systems are utilized in which native neurotrophins initiate an apoptotic response:

The first model is neurotrophin induced apoptosis of p75 expressing vascular smooth muscle cells (Wang, S., et al. 2000. Am J Pathol 157:1247-1258) which exhibit dose dependent increases in apoptosis using 2-5 nM NGF or BDNF, as quantitated by flow cytometric analysis of Annexin V binding. Concentrations of neurotrophin below 2 nM are not effective whereas dose responsiveness at 2-5 nM concentrations provides a quantitative analysis necessary to distinguish between ligands with reduced or enhanced activation of p75. p75 expressing vascular smooth muscle cells are treated with native or cleavage resistant neurotrophins for 18 hrs, and the proportion of cells exhibiting early or late apoptosis quantitated using flow cytometric analysis. Cells with Annexin V binding, but no propidium iodide uptake (early apoptosis) or both Annexin V binding and propidium iodide uptake (indicative of late apoptosis) are quantitated readily, as has been detailed (Wang, S., et al. 2000. Am J Pathol 157:1247-1258).

In addition, the rat neonatal oligodendrocyte assay, may be used (Casaccia-Bonnefil, P., et al. 1996. Nature 383:716-719). Cell cultured in oligodendrocyte differentiation media is switched to serum free media on neurotrophins (0.5 to 10 nM) and cell apoptosis is quantitated by TUNEL analysis at 8 hours.

Lastly, neuronal cultures may be used to compare the biological actions of native or cleavage resistant neurotrophins on cells which express both trk and p75, and exhibit responsiveness by neuritogenesis and survival. Primary cell cultures may be used, for example, cervical ganglion neurons, hippocampal neurons or dorsal root ganglion neurons. In addition, stable PC12 cell clones expressing either trk A or trk B at significant levels (approximately 70,000 receptors/cell) and have well characterized responses in terms of neurite extension (Hempstead, B. L., et al. 1992. Neuron 9:883-896) are preferred. Dose response studies ($0.5 \times 10^{-11}$ M) are performed using native or cleavage resistant proneurotrophin and neurite outgrowth at 48 hours is quantitated by counting cells with neurites of greater than two cell bodies in length. Cell survival assays may be performed, using neurons from rat dorsal root ganglia. These cells express either trk A and p75, or trk B and p75, and thus are useful in assessing the biological activities of mutant NGF or BDNF.

Results obtained using cells which co-express both p75 and trk receptors are interpreted in the context of those obtained using cells which express each receptor independently, as well as in the results of receptor binding studies. This careful analysis of biological activity, in conjunction with assessment of affinity constants and association and dissociation constants, allows clear identifications of the actions of larger proforms of the neurotrophins to (1) selectively bind p75 or trk receptors independently; (2) bind to high affinity multimeric receptor complexes and (3) distinguish between apoptotic and differentiation/survival activities in neurons and oligogendrocytes.

Taken together, these results indicate that the uncleaved, pro-form of neurotrophins is a preferred ligand for the pro-apoptotic p75 receptor, whereas the proteolytically cleaved mature neurotrophins is the preferred ligand for trk receptors. These results indicate that the regulated cleavage of proneurotrophins profoundly alters their biological actions, and that the proneurotrophins are higher affinity ligands for p75.

What is claimed is:

1. A method for inhibiting apoptosis of a cell, the method comprising exposing the cell to an effective amount of a molecule, wherein said molecule comprises the hypervariable region of an antibody, wherein said antibody binds to the pro-domain of a proneurotrophin and specifically inhibits the binding of said proneurotrophin to a p75 receptor.

2. A method according to claim 1, where said cell is a cell in a mammal, and the effective amount of said molecule is administered to said mammal.

3. The method according to claim 1, wherein the pro-neurotrophin is NGF.

4. The method according to claim 1, wherein the pro-neurotrophin is BDNF.

5. The method according to claim 1, wherein the pro-neurotrophin is NT-3.

6. The method according to claim 1, wherein the pro-neurotrophin is NT-4/5.

7. The method according to claim 1, wherein the cell is a cell of the nervous system.

8. The method according to claim 7, wherein the cell is a cell of the central nervous system.

9. The method according to claim 7, wherein the cell is a cell of the peripheral nervous system.

10. The method according to claim 7, wherein the cell is a neuron.

11. The method according to claim 1, wherein the molecule comprises the variable region of an antibody.

12. The method according to claim 1, wherein the molecule is an antibody.

13. The method according to claim 12, wherein the antibody is a chimeric antibody.

14. The method according to claim 12, wherein the antibody is a humanized antibody.

15. The method according to claim 12, wherein the molecule is a single chain antibody.

16. A method according to claim 2, wherein the mammal is a human.

17. The method according to claim 16, wherein the human suffers from a condition associated with undesired apoptosis due to binding of a proneurotrophin to a p75 receptor.

18. The method according to claim 17, wherein the p75 receptor, the proneurotrophin, or both are overexpressed in the human.

19. The method according to claim 17, wherein the condition is the result of an injury or an environmental insult.

20. The method according to claim 19, wherein the injury or environmental insult is a nervous system injury.

21. The method according to claim 20, wherein the condition is spinal cord injury.

22. The method according to claim 19, wherein the injury or environmental insult is caused by a chemical or radiation.

23. The method according to claim 19, wherein the injury or environmental insult occurs during treatment for cancer.

24. The method according to claim 17, wherein the condition is hypoxic ischemia.

25. The method according to claim 24, wherein the hypoxic ischemia is caused by a stroke.

26. The method according to claim 24, wherein the hypoxic ischemia is caused by a heart attack.

27. The method according to claim 17, wherein the condition is caused by a viral or microbial infection.

28. The method according to claim 27, wherein the condition is meningitis, encephalitis, or abscesses.

29. The method according to claim 27, wherein the microbial infection is a viral infection.

30. The method according to claim 27, wherein the microbial infection is a bacterial infection.

31. The method according to claim 17, wherein the condition is a neurodegenerative disorder.

32. The method according to claim 17, wherein the condition is Alzheimer's disease, familial dysautonomia, ataxia telangectasia, Charcot-Marie-Tooth disease, Adreno leuko dystrophy, spinal muscular atrophy, Friedriech's ataxia.

33. The method according to claim 17, wherein the condition is multiple sclerosis.

34. The method according to claim 17, wherein the condition causes convulsions.

35. The method according to claim 34, wherein the condition is epilepsy.

* * * * *

SEQUENCE LISTING

```
<160> NUMBER OF SEQ ID NOS: 118

<210> SEQ ID NO 1
<211> LENGTH: 241
<212> TYPE: PRT
<213> ORGANISM: Homo sapien

<400> SEQUENCE: 1

Met Ser Met Leu Phe Tyr Thr Leu Ile Thr Ala Phe Leu Ile Gly Ile
1               5                   10                  15
```

-continued

```
Gln Ala Glu Pro His Ser Glu Ser Asn Val Pro Ala Gly His Thr Ile
             20                  25                  30

Pro Gln Val His Trp Thr Lys Leu Gln His Ser Leu Asp Thr Ala Leu
         35                  40                  45

Arg Arg Ala Arg Ser Ala Pro Ala Ala Ile Ala Ala Arg Val Ala
 50                  55                  60

Gly Gln Thr Arg Asn Ile Thr Val Asp Pro Arg Leu Phe Lys Lys Arg
 65                  70                  75                  80

Arg Leu Arg Ser Pro Arg Val Leu Phe Ser Thr Gln Pro Pro Arg Glu
                 85                  90                  95

Ala Ala Asp Thr Gln Asp Leu Asp Phe Glu Val Gly Gly Ala Ala Pro
             100                 105                 110

Phe Asn Arg Thr His Arg Ser Lys Arg Ser Ser Ser His Pro Ile Phe
         115                 120                 125

His Arg Gly Glu Phe Ser Val Cys Asp Ser Val Ser Val Trp Val Gly
130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                 165                 170                 175

Thr Lys Cys Arg Asp Pro Asn Pro Val Asp Ser Gly Cys Arg Gly Ile
             180                 185                 190

Asp Ser Lys His Trp Asn Ser Tyr Cys Thr Thr Thr His Thr Phe Val
         195                 200                 205

Lys Ala Leu Thr Met Asp Gly Lys Gln Ala Ala Trp Arg Phe Ile Arg
210                 215                 220

Ile Asp Thr Ala Cys Val Cys Val Leu Ser Arg Lys Ala Val Arg Arg
225                 230                 235                 240

Ala

<210> SEQ ID NO 2
<211> LENGTH: 247
<212> TYPE: PRT
<213> ORGANISM: Homo sapien

<400> SEQUENCE: 2

Met Thr Ile Leu Phe Leu Thr Met Val Ile Ser Tyr Phe Gly Cys Met
 1               5                  10                  15

Lys Ala Ala Pro Met Lys Glu Ala Asn Ile Arg Gly Gln Gly Gly Leu
             20                  25                  30

Ala Tyr Pro Gly Val Arg Thr His Gly Thr Leu Glu Ser Val Asn Gly
         35                  40                  45

Pro Lys Ala Gly Ser Arg Gly Leu Thr Ser Leu Ala Asp Thr Phe Glu
 50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                 85                  90                  95

Ser Ser Gln Val Pro Leu Glu Pro Pro Leu Leu Phe Leu Leu Glu Glu
             100                 105                 110

Tyr Lys Asn Tyr Leu Asp Ala Ala Asn Met Ser Met Arg Val Arg Arg
         115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
```

```
                 145                 150                 155                 160
Gly Gly Thr Val Thr Val Leu Glu Lys Val Pro Val Ser Lys Gly Gln
                165                 170                 175
Leu Lys Gln Tyr Phe Tyr Glu Thr Lys Cys Asn Pro Met Gly Tyr Thr
            180                 185                 190
Lys Glu Gly Cys Arg Gly Ile Asp Lys Arg His Trp Asn Ser Gln Cys
        195                 200                 205
Arg Thr Thr Gln Ser Tyr Val Arg Ala Leu Thr Met Asp Ser Lys Lys
    210                 215                 220
Arg Ile Gly Trp Arg Phe Ile Arg Ile Asp Thr Ser Cys Val Cys Thr
225                 230                 235                 240
Leu Thr Ile Lys Arg Gly Arg
                245

<210> SEQ ID NO 3
<211> LENGTH: 257
<212> TYPE: PRT
<213> ORGANISM: Homo sapien

<400> SEQUENCE: 3

Met Ser Ile Leu Phe Tyr Val Ile Phe Leu Ala Tyr Leu Arg Gly Ile
1               5                   10                  15
Gln Gly Asn Asn Met Asp Gln Arg Ser Leu Pro Glu Asp Ser Leu Asn
            20                  25                  30
Ser Leu Ile Ile Lys Leu Ile Gln Ala Asp Ile Leu Lys Asn Lys Leu
        35                  40                  45
Ser Lys Gln Met Val Asp Val Lys Glu Asn Tyr Gln Ser Thr Leu Pro
    50                  55                  60
Lys Ala Glu Ala Pro Arg Glu Pro Glu Arg Gly Gly Pro Ala Lys Ser
65                  70                  75                  80
Ala Phe Gln Pro Val Ile Ala Met Asp Thr Glu Leu Leu Arg Gln Gln
                85                  90                  95
Arg Arg Tyr Asn Ser Pro Arg Val Leu Leu Ser Asp Ser Thr Pro Leu
            100                 105                 110
Glu Pro Pro Pro Leu Tyr Leu Met Glu Asp Tyr Val Gly Ser Pro Val
        115                 120                 125
Val Ala Asn Arg Thr Ser Arg Arg Lys Arg Tyr Ala Glu His Lys Ser
    130                 135                 140
His Arg Gly Glu Tyr Ser Val Cys Asp Ser Glu Ser Leu Trp Val Thr
145                 150                 155                 160
Asp Lys Ser Ser Ala Ile Asp Ile Arg Gly His Gln Val Thr Val Leu
                165                 170                 175
Gly Glu Ile Lys Thr Gly Asn Ser Pro Val Lys Gln Tyr Phe Tyr Glu
            180                 185                 190
Thr Arg Cys Lys Glu Ala Arg Pro Val Lys Asn Gly Cys Arg Gly Ile
        195                 200                 205
Asp Asp Lys His Trp Asn Ser Gln Cys Lys Thr Ser Gln Thr Tyr Val
    210                 215                 220
Arg Ala Leu Thr Ser Glu Asn Asn Lys Leu Val Gly Trp Arg Trp Ile
225                 230                 235                 240
Arg Ile Asp Thr Ser Cys Val Cys Ala Leu Ser Arg Lys Ile Gly Arg
                245                 250                 255
Thr

<210> SEQ ID NO 4
```

```
<211> LENGTH: 210
<212> TYPE: PRT
<213> ORGANISM: Homo sapien

<400> SEQUENCE: 4

Met Leu Pro Leu Pro Ser Cys Ser Leu Pro Ile Leu Leu Phe Leu
1               5                   10                  15

Leu Pro Ser Val Pro Ile Glu Ser Gln Pro Pro Ser Thr Leu Pro
                20                  25                  30

Pro Phe Leu Ala Pro Glu Trp Asp Leu Leu Ser Pro Arg Val Leu
            35                  40                  45

Ser Arg Gly Ala Pro Ala Gly Pro Pro Leu Leu Phe Leu Leu Glu Ala
50                      55                  60

Gly Ala Phe Arg Glu Ser Ala Gly Ala Pro Ala Asn Arg Ser Arg Arg
65              70                  75                      80

Gly Val Ser Glu Thr Ala Pro Ala Ser Arg Arg Gly Glu Leu Ala Val
                85                  90                  95

Cys Asp Ala Val Ser Gly Trp Val Thr Asp Arg Arg Thr Ala Val Asp
            100                 105                 110

Leu Arg Gly Arg Glu Val Glu Val Leu Gly Glu Val Pro Ala Ala Gly
        115                 120                 125

Gly Ser Pro Leu Arg Gln Tyr Phe Phe Glu Thr Arg Cys Lys Ala Asp
130                 135                 140

Asn Ala Glu Glu Gly Gly Pro Gly Ala Gly Gly Gly Cys Arg Gly
145             150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
            180                 185                 190

Ile Arg Ile Asp Thr Ala Cys Val Cys Thr Leu Leu Ser Arg Thr Gly
        195                 200                 205

Arg Ala
    210

<210> SEQ ID NO 5
<211> LENGTH: 427
<212> TYPE: PRT
<213> ORGANISM: Homo sapien

<400> SEQUENCE: 5

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
65              70                  75                      80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125
```

```
Glu Ala Gly Ser Gly Leu Val Phe Ser Cys Gln Asp Lys Gln Asn Thr
            130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Glu Gly Ser Asp Ser Thr
            195                 200                 205

Ala Pro Ser Thr Gln Glu Pro Glu Ala Pro Pro Glu Gly Asp Leu Ile
            210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
                260                 265                 270

Lys Arg Trp Asn Ser Cys Lys Gln Asn Lys Gln Gly Ala Asn Ser Arg
            275                 280                 285

Pro Val Asn Gln Thr Pro Pro Pro Glu Gly Glu Lys Leu His Ser Asp
            290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
                340                 345                 350

Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
            370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

<210> SEQ ID NO 6
<211> LENGTH: 241
<212> TYPE: PRT
<213> ORGANISM: Homo sapien

<400> SEQUENCE: 6

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
                20                  25                  30

Pro Gln Val His Trp Thr Lys Leu Gln His Ser Leu Asp Thr Ala Leu
                35                  40                  45

Arg Arg Ala Arg Ser Ala Pro Ala Ala Ile Ala Ala Arg Val Ala
            50                  55                  60

Gly Gln Thr Arg Asn Ile Thr Val Asp Pro Arg Leu Phe Lys Lys Arg
65                  70                  75                  80
```

```
Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser His Pro Ile Phe
        115                 120                 125

His Arg Gly Glu Phe Ser Val Cys Asp Ser Val Ser Val Trp Val Gly
130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
210                 215                 220

Ile Asp Thr Ala Cys Val Cys Val Leu Ser Arg Lys Ala Val Arg Arg
225                 230                 235                 240

Ala

<210> SEQ ID NO 7
<211> LENGTH: 241
<212> TYPE: PRT
<213> ORGANISM: Gorilla gorilla

<400> SEQUENCE: 7

Met Ser Met Leu Phe Tyr Thr Leu Ile Thr Ala Phe Leu Ile Gly Ile
1               5                   10                  15

Gln Ala Glu Leu His Ser Glu Ser Asn Val Pro Ala Gly His Thr Ile
                20                  25                  30

Pro Gln Ala His Trp Thr Lys Leu Gln His Ser Leu Asp Thr Ala Leu
            35                  40                  45

Arg Arg Ala Arg Ser Ala Pro Ala Ala Ala Ile Ala Ala Arg Val Ala
        50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser His Pro Ile Phe
        115                 120                 125

His Arg Gly Glu Phe Ser Val Cys Asp Ser Val Ser Val Trp Val Gly
130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
```

```
                    210                 215                 220
Ile Asp Thr Ala Cys Val Cys Val Leu Ser Arg Lys Ala Val Arg Arg
225                 230                 235                 240

Ala

<210> SEQ ID NO 8
<211> LENGTH: 241
<212> TYPE: PRT
<213> ORGANISM: Rattus norvegicus

<400> SEQUENCE: 8

Met Ser Met Leu Phe Tyr Thr Leu Ile Thr Ala Phe Leu Ile Gly Val
1               5                   10                  15

Gln Ala Glu Pro Tyr Thr Asp Ser Asn Val Pro Glu Gly Asp Ser Val
                20                  25                  30

Pro Glu Ala His Trp Thr Lys Leu Gln His Ser Leu Asp Thr Ala Leu
            35                  40                  45

Arg Arg Ala Arg Ser Ala Pro Ala Glu Pro Ile Ala Ala Arg Val Thr
    50                  55                  60

Gly Gln Thr Arg Asn Ile Thr Val Asp Pro Lys Leu Phe Lys Lys Arg
65                  70                  75                  80

Arg Leu Arg Ser Pro Arg Val Leu Phe Ser Thr Gln Pro Pro Pro Thr
                85                  90                  95

Ser Ser Asp Thr Leu Asp Leu Asp Phe Gln Ala His Gly Thr Ile Ser
                100                 105                 110

Phe Asn Arg Thr His Arg Ser Lys Arg Ser Ser Thr His Pro Val Phe
            115                 120                 125

His Met Gly Glu Phe Ser Val Cys Asp Ser Val Ser Val Trp Val Gly
    130                 135                 140

Asp Lys Thr Thr Ala Thr Asp Ile Lys Gly Lys Glu Val Thr Val Leu
145                 150                 155                 160

Gly Glu Val Asn Ile Asn Asn Ser Val Phe Lys Gln Tyr Phe Phe Glu
                165                 170                 175

Thr Lys Cys Arg Ala Pro Asn Pro Val Glu Ser Gly Cys Arg Gly Ile
                180                 185                 190

Asp Ser Lys His Trp Asn Ser Tyr Cys Thr Thr Thr His Thr Phe Val
            195                 200                 205

Lys Ala Leu Thr Thr Asp Lys Gln Ala Ala Trp Arg Phe Ile Arg
    210                 215                 220

Ile Asp Thr Ala Cys Val Cys Val Leu Ser Arg Lys Ala Ala Arg Arg
225                 230                 235                 240

Gly

<210> SEQ ID NO 9
<211> LENGTH: 241
<212> TYPE: PRT
<213> ORGANISM: Mus musculus

<400> SEQUENCE: 9

Met Ser Met Leu Phe Tyr Thr Leu Ile Thr Ala Phe Leu Ile Gly Val
1               5                   10                  15

Gln Ala Glu Pro Tyr Thr Asp Ser Asn Val Pro Glu Gly Asp Ser Val
                20                  25                  30

Pro Glu Ala His Trp Thr Lys Leu Gln His Ser Leu Asp Thr Ala Leu
            35                  40                  45

Arg Arg Ala Arg Ser Ala Pro Thr Ala Pro Ile Ala Ala Arg Val Thr
```

```
            50                  55                  60
Gly Gln Thr Arg Asn Ile Thr Val Asp Pro Arg Leu Phe Lys Lys Arg
 65                  70                  75                  80

Arg Leu His Ser Pro Arg Val Leu Phe Ser Thr Gln Pro Pro Pro Thr
                 85                  90                  95

Ser Ser Asp Thr Leu Asp Leu Asp Phe Gln Ala His Gly Thr Ile Pro
            100                 105                 110

Phe Asn Arg Thr His Arg Ser Lys Arg Ser Ser Thr His Pro Val Phe
                115                 120                 125

His Met Gly Glu Phe Ser Val Cys Asp Ser Val Ser Val Trp Val Gly
130                 135                 140

Asp Lys Thr Thr Ala Thr Asp Ile Lys Gly Lys Glu Val Thr Val Leu
145                 150                 155                 160

Ala Glu Val Asn Ile Asn Asn Ser Val Phe Arg Gln Tyr Phe Phe Glu
                165                 170                 175

Thr Lys Cys Arg Ala Ser Asn Pro Val Glu Ser Gly Cys Arg Gly Ile
            180                 185                 190

Asp Ser Lys His Trp Asn Ser Tyr Cys Thr Thr His Thr Phe Val
            195                 200                 205

Lys Ala Leu Thr Thr Asp Glu Lys Gln Ala Trp Arg Phe Ile Arg
210                 215                 220

Ile Asp Thr Ala Cys Val Cys Val Leu Ser Arg Lys Ala Thr Arg Arg
225                 230                 235                 240

Gly

<210> SEQ ID NO 10
<211> LENGTH: 231
<212> TYPE: PRT
<213> ORGANISM: Bos taurus

<400> SEQUENCE: 10

Ala Phe Leu Ile Gly Ile Gln Ala Ala Pro His Thr Glu Ser Asn Val
 1               5                  10                  15

Pro Ala Gly His Ala Ile Pro Gln Ala His Trp Ile Lys Leu Gln His
                20                  25                  30

Ser Leu Asp Thr Val Leu Arg Arg Ala His Ser Ala Pro Ala Gly Pro
            35                  40                  45

Ile Ala Ala Arg Val Ala Gly Gln Thr His Asn Ile Thr Val Asp Pro
 50                  55                  60

Lys Leu Phe Lys Lys Arg Arg Leu Arg Ser Arg Val Leu Phe Ser
 65                  70                  75                  80

Thr Gln Pro Pro Val Ala Ala Asp Thr Gln Asp Leu Asp Phe Glu
                 85                  90                  95

Ala Gly Gly Ala Ser Ser Phe Asn Arg Thr His Arg Ser Lys Arg Ser
            100                 105                 110

Ser Ser His Pro Val Leu His Arg Gly Glu Phe Ser Val Cys Asp Ser
            115                 120                 125

Ile Ser Val Trp Val Gly Asp Lys Thr Thr Ala Thr Asp Ile Lys Gly
130                 135                 140

Lys Glu Val Met Val Leu Gly Glu Val Asn Ile Asn Asn Ser Val Phe
145                 150                 155                 160

Arg Gln Tyr Phe Phe Glu Thr Lys Cys Arg Asp Pro Asn Pro Val Asp
                165                 170                 175

Ser Gly Cys Arg Gly Ile Asp Ala Lys His Trp Asn Ser Tyr Cys Thr
            180                 185                 190
```

```
Thr Thr His Thr Phe Val Lys Ala Leu Thr Met Asp Gly Lys Gln Ala
        195                 200                 205

Ala Trp Arg Phe Ile Arg Ile Asp Thr Ala Cys Val Cys Val Leu Ser
    210                 215                 220

Arg Lys Thr Gly Gln Ala Pro
225                 230

<210> SEQ ID NO 11
<211> LENGTH: 243
<212> TYPE: PRT
<213> ORGANISM: Gallus gallus

<400> SEQUENCE: 11

Met His Ser Val Met Ser Met Leu Tyr Tyr Thr Leu Ile Ile Ala Phe
1               5                   10                  15

Leu Ile Gly Thr Gln Ala Ala Pro Lys Ser Glu Asp Asn Gly Pro Leu
            20                  25                  30

Glu Tyr Pro Ala Glu His Ser Leu Pro Ser Thr Gln Ser Asn Gly
        35                  40                  45

Gln His Ile Ala Lys Ala Ala Pro Gln Thr Thr His Gly Arg Phe Ala
    50                  55                  60

Trp Met Pro Asp Gly Thr Glu Asp Leu Asn Ile Ala Met Asp Gln Asn
65                  70                  75                  80

Phe Phe Lys Lys Lys Arg Phe Arg Ser Ser Arg Val Leu Phe Ser Thr
                85                  90                  95

Gln Pro Pro Pro Val Ser Arg Lys Gly Gln Ser Thr Gly Phe Leu Ser
            100                 105                 110

Ser Ala Val Ser Leu Asn Arg Thr Ala Arg Thr Lys Arg Thr Ala His
        115                 120                 125

Pro Val Leu His Arg Gly Glu Phe Ser Val Cys Asp Ser Val Ser Met
    130                 135                 140

Trp Val Gly Asp Lys Thr Thr Ala Thr Asp Ile Lys Gly Lys Glu Val
145                 150                 155                 160

Thr Val Leu Gly Glu Val Asn Ile Asn Asn Val Phe Lys Gln Tyr
                165                 170                 175

Phe Phe Glu Thr Lys Cys Arg Asp Pro Arg Pro Val Ser Ser Gly Cys
            180                 185                 190

Arg Gly Ile Asp Ala Lys His Trp Asn Ser Tyr Cys Thr Thr Thr His
        195                 200                 205

Thr Phe Val Lys Ala Leu Thr Met Glu Gly Lys Gln Ala Ala Trp Arg
    210                 215                 220

Phe Ile Arg Ile Asp Thr Ala Cys Val Cys Val Leu Ser Arg Lys Ser
225                 230                 235                 240

Gly Arg Pro

<210> SEQ ID NO 12
<211> LENGTH: 235
<212> TYPE: PRT
<213> ORGANISM: Xenopus laevis

<400> SEQUENCE: 12

Val Asp Arg Val Met Ser Met Leu Tyr Tyr Thr Leu Leu Ile Ala Ile
1               5                   10                  15

Leu Ile Ser Val Gln Ala Ala Pro Lys Thr Lys Asp His Ala Pro Ala
            20                  25                  30

Arg Ser Ser Ala Lys Ser Arg Ile Pro His His Thr His Arg Thr Lys
```

```
                 35                  40                  45
Ser Leu His His Ser His Gly Lys Leu Glu Ala Lys Glu Pro Ser Tyr
 50                  55                  60

Phe Arg Asn Val Thr Val Asp Pro Lys Leu Phe Arg Lys Arg Lys Phe
 65                  70                  75                  80

Arg Ser Pro Arg Val Leu Phe Ser Thr Gln Pro Pro Leu Ser Glu
                 85                  90                  95

Asp Phe Gln His Leu Glu Tyr Leu Asp Asp Glu Glu Ser Leu Asn Lys
                100                 105                 110

Thr Ile Arg Ala Lys Arg Thr Val His Pro Val Leu His Lys Gly Glu
                115                 120                 125

Tyr Ser Val Cys Asp Ser Val Ser Met Trp Val Gly Glu Lys Thr Lys
130                 135                 140

Ala Thr Asp Ile Lys Gly Lys Glu Val Thr Val Leu Gly Glu Val Asn
145                 150                 155                 160

Ile Asn Asn Ser Val Phe Lys Gln Tyr Phe Glu Thr Lys Cys Arg
                165                 170                 175

Asp Pro Lys Pro Val Ser Ser Gly Cys Arg Gly Ile Asp Ala Lys His
                180                 185                 190

Trp Asn Ser Tyr Cys Thr Thr Thr His Thr Phe Val Lys Ala Leu Thr
                195                 200                 205

Met Glu Gly Lys Gln Ala Ala Trp Arg Phe Ile Arg Ile Asp Thr Ala
210                 215                 220

Cys Val Cys Val Leu Ser Arg Lys Gly Arg Thr
225                 230                 235

<210> SEQ ID NO 13
<211> LENGTH: 248
<212> TYPE: PRT
<213> ORGANISM: bos taurus

<400> SEQUENCE: 13

Ile Leu Phe Leu Thr Met Val Ile Ser Tyr Phe Gly Cys Met Lys Ala
1               5                   10                  15

Ala Pro Met Lys Glu Ala Asn Leu Arg Ala Gln Gly Ser Leu Thr Tyr
                20                  25                  30

Pro Gly Val Arg Thr His Gly Thr Leu Glu Ser Met Asn Gly Pro Lys
                35                  40                  45

Val Gly Ser Arg Gly Leu Thr Ser Ser Ser Leu Ala Asp Thr Phe
 50                  55                  60

Glu His Val Ile Glu Glu Leu Leu Asp Glu Asp Gln Lys Val Arg Pro
 65                  70                  75                  80

Ser Glu Glu Asn Asn Lys Asp Ala Asp Met Tyr Thr Ser Arg Val Met
                85                  90                  95

Leu Ser Ser Gln Val Pro Leu Glu Pro Pro Leu Leu Phe Leu Leu Glu
                100                 105                 110

Glu Tyr Lys Asn Tyr Leu Asp Ala Ala Asn Met Ser Met Arg Val Arg
                115                 120                 125

Arg His Ser Asp Pro Ala Arg Arg Gly Glu Leu Ser Val Cys Asp Ser
                130                 135                 140

Ile Ser Glu Trp Val Thr Ala Ala Asp Lys Arg Leu Ala Val Asp Met
145                 150                 155                 160

Ser Gly Gly Thr Val Thr Val Leu Glu Lys Val Pro Val Ser Lys Gly
                165                 170                 175

Gln Leu Lys Gln Tyr Phe Tyr Glu Thr Lys Cys Asn Pro Met Gly Tyr
```

```
                          180                 185                 190
Thr Lys Glu Gly Cys Arg Gly Ile Asp Lys Arg His Trp Asn Ser Gln
            195                 200                 205

Cys Arg Thr Thr Gln Ser Tyr Val Arg Ala Leu Thr Met Asp Ser Lys
        210                 215                 220

Lys Arg Ile Gly Trp Arg Phe Ile Arg Ile Asp Thr Ser Cys Val Cys
225                 230                 235                 240

Thr Leu Thr Ile Lys Arg Gly Arg
                245

<210> SEQ ID NO 14
<211> LENGTH: 249
<212> TYPE: PRT
<213> ORGANISM: Rattus norvegicus

<400> SEQUENCE: 14

Met Thr Ile Leu Phe Leu Thr Met Val Ile Ser Tyr Phe Gly Cys Met
1               5                   10                  15

Lys Ala Ala Pro Met Lys Glu Ala Asn Val His Gly Gln Gly Asn Leu
            20                  25                  30

Ala Tyr Pro Ala Val Arg Thr His Gly Thr Leu Glu Ser Val Asn Gly
        35                  40                  45

Pro Arg Ala Gly Ser Arg Gly Leu Thr Thr Thr Ser Leu Ala Asp Thr
    50                  55                  60

Phe Glu His Val Ile Glu Glu Leu Leu Asp Glu Asp Gln Lys Val Arg
65                  70                  75                  80

Pro Asn Glu Glu Asn His Lys Asp Ala Asp Leu Tyr Thr Ser Arg Val
                85                  90                  95

Met Leu Ser Ser Gln Val Pro Leu Glu Pro Pro Leu Leu Phe Leu Leu
            100                 105                 110

Glu Glu Tyr Lys Asn Tyr Leu Asp Ala Ala Asn Met Ser Met Arg Val
        115                 120                 125

Arg Arg His Ser Asp Pro Ala Arg Arg Gly Glu Leu Ser Val Cys Asp
    130                 135                 140

Ser Ile Ser Glu Trp Val Thr Ala Ala Asp Lys Lys Thr Ala Val Asp
145                 150                 155                 160

Met Ser Gly Gly Thr Val Thr Val Leu Glu Lys Val Pro Val Ser Lys
                165                 170                 175

Gly Gln Leu Lys Gln Tyr Phe Tyr Glu Thr Lys Cys Asn Pro Met Gly
            180                 185                 190

Tyr Thr Lys Glu Gly Cys Arg Gly Ile Asp Lys Arg His Trp Asn Ser
        195                 200                 205

Gln Cys Arg Thr Thr Gln Ser Tyr Val Arg Ala Leu Thr Met Asp Ser
    210                 215                 220

Lys Lys Arg Ile Gly Trp Arg Phe Ile Arg Ile Asp Thr Ser Cys Val
225                 230                 235                 240

Cys Thr Leu Thr Ile Lys Arg Gly Arg
                245

<210> SEQ ID NO 15
<211> LENGTH: 249
<212> TYPE: PRT
<213> ORGANISM: Mus musculus

<400> SEQUENCE: 15

Met Thr Ile Leu Phe Leu Thr Met Val Ile Ser Tyr Phe Gly Cys Met
1               5                   10                  15
```

Lys Ala Ala Pro Met Lys Glu Val Asn Val His Gly Gln Gly Asn Leu
            20                  25                  30

Ala Tyr Pro Gly Val Arg Thr His Gly Thr Leu Glu Ser Val Asn Gly
        35                  40                  45

Pro Arg Ala Gly Ser Arg Gly Leu Thr Thr Thr Ser Leu Ala Asp Thr
50                  55                  60

Phe Glu His Val Ile Glu Leu Leu Asp Glu Asp Gln Lys Val Arg
65                  70                  75                  80

Pro Asn Glu Glu Asn His Lys Asp Ala Asp Leu Tyr Thr Ser Arg Val
                85                  90                  95

Met Leu Ser Ser Gln Val Pro Leu Glu Pro Pro Leu Leu Phe Leu Leu
            100                 105                 110

Glu Glu Tyr Lys Asn Tyr Leu Asp Ala Ala Asn Met Ser Met Arg Val
            115                 120                 125

Arg Arg His Ser Asp Pro Ala Arg Arg Gly Glu Leu Ser Val Cys Asp
        130                 135                 140

Ser Ile Ser Glu Trp Val Thr Ala Ala Asp Lys Lys Thr Ala Val Asp
145                 150                 155                 160

Met Ser Gly Gly Thr Val Thr Val Leu Glu Lys Val Pro Val Ser Lys
                165                 170                 175

Gly Gln Leu Lys Gln Tyr Phe Tyr Glu Thr Lys Cys Asn Pro Met Gly
            180                 185                 190

Tyr Thr Lys Glu Gly Cys Arg Gly Ile Asp Lys Arg His Trp Asn Ser
            195                 200                 205

Gln Cys Arg Thr Thr Gln Ser Tyr Val Arg Ala Leu Thr Met Asp Ser
        210                 215                 220

Lys Lys Arg Ile Gly Trp Arg Phe Ile Arg Ile Asp Thr Ser Cys Val
225                 230                 235                 240

Cys Thr Leu Thr Ile Lys Arg Gly Arg
                245

<210> SEQ ID NO 16
<211> LENGTH: 246
<212> TYPE: PRT
<213> ORGANISM: Gallus gallus

<400> SEQUENCE: 16

Met Thr Ile Leu Phe Leu Thr Met Val Ile Ser Tyr Phe Ser Cys Met
1               5                   10                  15

Lys Ala Ala Pro Met Lys Glu Ala Ser Val Arg Gly His Gly Ser Leu
            20                  25                  30

Ala Tyr Pro Gly Leu Arg Thr His Gly Thr Leu Glu Ser Leu Thr Gly
        35                  40                  45

Pro Asn Ala Gly Ser Arg Gly Leu Thr Ser Leu Ala Asp Thr Phe Glu
50                  55                  60

His Val Ile Glu Glu Leu Leu Asp Glu Asp Gln Asp Ile Gln Pro Ser
65                  70                  75                  80

Glu Glu Asn Lys Asp Ala Asp Leu Tyr Thr Ser Arg Val Met Leu Ser
            85                  90                  95

Ser Gln Val Pro Leu Glu Pro Pro Leu Leu Phe Leu Leu Glu Glu Tyr
            100                 105                 110

Lys Asn Tyr Leu Asp Ala Ala Asn Met Ser Met Arg Val Arg Arg His
        115                 120                 125

Ser Asp Pro Ala Arg Arg Gly Glu Leu Ser Val Cys Asp Ser Thr Ser
    130                 135                 140

```
Glu Trp Val Thr Ala Ala Glu Lys Lys Thr Ala Val Asp Met Ser Gly
145                 150                 155                 160

Ala Thr Val Thr Val Leu Glu Lys Val Pro Val Pro Lys Gly Gln Leu
            165                 170                 175

Lys Gln Tyr Phe Tyr Glu Thr Lys Cys Asn Pro Lys Gly Tyr Thr Lys
        180                 185                 190

Glu Gly Cys Arg Gly Ile Asp Lys Arg His Trp Asn Ser Gln Cys Arg
    195                 200                 205

Thr Thr Gln Ser Tyr Val Arg Ala Leu Thr Met Asp Asn Lys Lys Arg
        210                 215                 220

Val Gly Trp Arg Phe Ile Arg Ile Asp Thr Ser Cys Val Cys Thr Leu
225                 230                 235                 240

Thr Ile Lys Arg Gly Arg
                245

<210> SEQ ID NO 17
<211> LENGTH: 258
<212> TYPE: PRT
<213> ORGANISM: Rattus norvegicus

<400> SEQUENCE: 17

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Glu Gln Gly Glu Ala Thr Arg Ser
65                  70                  75                  80

Glu Phe Gln Pro Met Ile Ala Thr Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Asn Pro Val
        115                 120                 125

Val Thr Asn Arg Thr Ser Pro Arg Arg Lys Arg Tyr Ala Glu His Lys
130                 135                 140

Ser His Arg Gly Glu Tyr Ser Val Cys Asp Ser Glu Ser Leu Trp Val
145                 150                 155                 160

Thr Asp Lys Ser Ser Ala Ile Asp Ile Arg Gly His Gln Val Thr Val
                165                 170                 175

Leu Gly Glu Ile Lys Thr Gly Asn Ser Pro Val Lys Gln Tyr Phe Tyr
            180                 185                 190

Glu Thr Arg Cys Lys Glu Ala Arg Pro Val Lys Asn Gly Cys Arg Gly
        195                 200                 205

Ile Asp Asp Lys His Trp Asn Ser Gln Cys Lys Thr Ser Gln Thr Tyr
    210                 215                 220

Val Arg Ala Leu Thr Ser Glu Asn Asn Lys Leu Val Gly Trp Arg Trp
225                 230                 235                 240

Ile Arg Ile Asp Thr Ser Cys Val Cys Ala Leu Ser Arg Lys Ile Gly
                245                 250                 255

Arg Thr
```

<210> SEQ ID NO 18
<211> LENGTH: 258
<212> TYPE: PRT
<213> ORGANISM: Mus musculus

<400> SEQUENCE: 18

Met Ser Ile Leu Phe Tyr Val Ile Phe Leu Ala Tyr Leu Arg Gly Ile
1               5                   10                  15

Gln Gly Asn Ser Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Glu Gln Gly Glu Ala Thr Arg Ser
65                  70                  75                  80

Glu Phe Gln Pro Met Ile Ala Thr Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Asn Pro Val
        115                 120                 125

Val Ala Asn Arg Thr Ser Pro Arg Arg Lys Arg Tyr Ala Glu His Lys
130                 135                 140

Ser His Arg Gly Glu Tyr Ser Val Cys Asp Ser Glu Ser Leu Trp Val
145                 150                 155                 160

Thr Asp Lys Ser Ser Ala Ile Asp Ile Arg Gly His Gln Val Thr Val
                165                 170                 175

Leu Gly Glu Ile Lys Thr Gly Asn Ser Pro Val Lys Gln Tyr Phe Tyr
            180                 185                 190

Glu Thr Arg Cys Lys Glu Ala Arg Pro Val Lys Asn Gly Cys Arg Gly
        195                 200                 205

Ile Asp Asp Lys His Trp Asn Ser Gln Cys Lys Thr Ser Gln Thr Tyr
210                 215                 220

Val Arg Ala Leu Thr Ser Glu Asn Asn Lys Leu Val Gly Trp Arg Trp
225                 230                 235                 240

Ile Arg Ile Asp Thr Ser Cys Val Cys Ala Leu Ser Arg Lys Ile Gly
                245                 250                 255

Arg Thr

<210> SEQ ID NO 19
<211> LENGTH: 257
<212> TYPE: PRT
<213> ORGANISM: Gallus gallus

<400> SEQUENCE: 19

Met Ser Ile Leu Phe Tyr Val Ile Phe Leu Ala Tyr Leu Arg Gly Ile
1               5                   10                  15

Gln Ser Thr Asn Met Asp Gln Arg Ser Leu Pro Glu Asp Ser Met Asn
            20                  25                  30

Ser Leu Ile Ile Lys Leu Ile Arg Ala Asp Ile Leu Lys Asn Lys Leu
        35                  40                  45

Ser Lys Gln Val Met Asp Val Lys Glu Asn Tyr Gln Asn Ile Val Gln
50                  55                  60

Lys Val Glu Asp His Gln Glu Met Asp Gly Asp Glu Asn Val Lys Ser
65                  70                  75                  80

```
Asp Phe Gln Pro Val Ile Ser Met Asp Thr Asp Leu Leu Arg Gln Gln
                85                  90                  95

Arg Arg Tyr Asn Ser Pro Arg Val Leu Leu Ser Asp Asn Thr Pro Leu
            100                 105                 110

Glu Pro Pro Leu Tyr Leu Thr Glu Asp Tyr Val Gly Ser Ser Val
        115                 120                 125

Val Leu Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Lys Pro Val Lys Asn Gly Cys Arg Gly Ile
        195                 200                 205

Asp Asp Lys His Trp Asn Ser Gln Cys Lys Thr Ser Gln Thr Tyr Val
210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 20
<211> LENGTH: 260
<212> TYPE: PRT
<213> ORGANISM: Xenopus laevis

<400> SEQUENCE: 20

Met Ser Ile Leu Phe Tyr Val Met Phe Leu Pro Tyr Leu Cys Gly Ile
1               5                   10                  15

His Ala Thr Asn Met Asp Lys Arg Asn Leu Pro Glu Asn Ser Met Asn
            20                  25                  30

Ser Leu Phe Ile Lys Leu Ile Gln Ala Asp Leu Leu Lys Asn Lys Ile
        35                  40                  45

Ser Lys Gln Thr Val Asp Thr Lys Glu Asn His Gln Ser Thr Ile Pro
    50                  55                  60

Lys Pro Gln Ile Leu Leu Asp Leu Asp Gly Asp Asp Asn Met Lys Gln
65                  70                  75                  80

Asp Phe Gln Pro Val Ile Ser Leu Glu Ala Glu Leu Val Lys Gln Gln
                85                  90                  95

Lys Gln Arg Arg Tyr Lys Ser Pro Arg Val Leu Leu Ser Asp Ser Leu
            100                 105                 110

Pro Leu Glu Pro Pro Leu Tyr Leu Met Asp Asp Tyr Ile Gly His
        115                 120                 125

Ser Thr Val Val Asn Asn Arg Thr Ser Arg Arg Lys Arg Phe Ala Glu
130                 135                 140

His Lys Gly His Arg Gly Glu Tyr Ser Val Cys Asp Ser Glu Ser Leu
145                 150                 155                 160

Trp Val Thr Asp Lys Met Asn Ala Ile Asp Ile Arg Gly His Gln Val
                165                 170                 175

Thr Val Leu Gly Glu Ile Lys Thr Gly Asn Ser Pro Val Lys Gln Tyr
            180                 185                 190
```

```
Phe Tyr Glu Thr Arg Cys Lys Glu Ala Arg Pro Val Lys Asn Gly Cys
            195                 200                 205

Arg Gly Ile Asp Asp Lys His Trp Asn Ser Gln Cys Lys Thr Ser Gln
        210                 215                 220

Thr Tyr Val Arg Ala Leu Thr Ser Glu Asn Asn Lys Met Val Gly Trp
225                 230                 235                 240

Arg Trp Ile Arg Ile Asp Thr Ser Cys Val Cys Ala Leu Ser Arg Lys
                245                 250                 255

Ile Gly Arg Ser
            260

<210> SEQ ID NO 21
<211> LENGTH: 209
<212> TYPE: PRT
<213> ORGANISM: Rattus norvegicus

<400> SEQUENCE: 21

Met Leu Pro Arg His Ser Cys Ser Leu Leu Phe Leu Leu Leu Leu Leu
1               5                   10                  15

Pro Ser Val Pro Met Glu Pro Gln Pro Ser Ser Thr Leu Pro Pro
            20                  25                  30

Phe Leu Ala Pro Glu Trp Asp Leu Leu Ser Pro Arg Val Ala Leu Ser
        35                  40                  45

Arg Gly Thr Pro Ala Gly Pro Pro Leu Leu Phe Leu Leu Glu Ala Gly
    50                  55                  60

Ala Tyr Gly Glu Pro Ala Gly Ala Pro Ala Asn Arg Ser Arg Arg Gly
65                  70                  75                  80

Val Ser Glu Thr Ala Pro Ala Ser Arg Arg Gly Glu Leu Ala Val Cys
                85                  90                  95

Asp Ala Val Ser Gly Trp Val Thr Asp Arg Arg Thr Ala Val Asp Leu
            100                 105                 110

Arg Gly Arg Glu Val Glu Val Leu Gly Glu Val Pro Ala Ala Gly Gly
        115                 120                 125

Ser Pro Leu Arg Gln Tyr Phe Phe Glu Thr Arg Cys Lys Ala Glu Ser
    130                 135                 140

Ala Gly Glu Gly Gly Pro Gly Val Gly Gly Gly Cys Arg Gly Val
145                 150                 155                 160

Asp Arg Arg His Trp Leu Ser Glu Cys Lys Ala Lys Gln Ser Tyr Val
                165                 170                 175

Arg Ala Leu Thr Ala Asp Ser Gln Gly Arg Val Gly Trp Arg Trp Ile
            180                 185                 190

Arg Ile Asp Thr Ala Cys Val Cys Thr Leu Leu Ser Arg Thr Gly Arg
        195                 200                 205

Ala

<210> SEQ ID NO 22
<211> LENGTH: 236
<212> TYPE: PRT
<213> ORGANISM: Xenopus laevis

<400> SEQUENCE: 22

Met Ile Leu Arg Leu Tyr Ala Met Val Ile Ser Tyr Cys Cys Ala Ile
1               5                   10                  15

Cys Ala Ala Pro Phe Gln Ser Arg Thr Thr Asp Leu Asp Tyr Gly Pro
            20                  25                  30

Asp Lys Thr Ser Glu Ala Ser Asp Arg Gln Ser Val Pro Asn Asn Phe
        35                  40                  45
```

```
Ser His Val Leu Gln Asn Gly Phe Phe Pro Asp Leu Ser Ser Thr Tyr
        50                  55                  60
Ser Ser Met Ala Gly Lys Asp Trp Asn Leu Tyr Ser Pro Arg Val Thr
 65                  70                  75                  80
Leu Ser Ser Glu Glu Pro Ser Gly Pro Pro Leu Leu Phe Leu Ser Glu
                 85                  90                  95
Glu Thr Val Val His Pro Glu Pro Ala Asn Lys Thr Ser Arg Leu Lys
                100                 105                 110
Arg Ala Ser Gly Ser Asp Ser Val Ser Leu Ser Arg Arg Gly Glu Leu
                115                 120                 125
Ser Val Cys Asp Ser Val Asn Val Trp Val Thr Asp Lys Arg Thr Ala
130                 135                 140
Val Asp Asp Arg Gly Lys Ile Val Thr Val Met Ser Glu Ile Gln Thr
145                 150                 155                 160
Leu Thr Gly Pro Leu Lys Gln Tyr Phe Phe Glu Thr Lys Cys Asn Pro
                165                 170                 175
Ser Gly Ser Thr Thr Arg Gly Cys Arg Gly Val Asp Lys Lys Gln Trp
                180                 185                 190
Ile Ser Glu Cys Lys Ala Lys Gln Ser Tyr Val Arg Ala Leu Thr Ile
                195                 200                 205
Asp Ala Asn Lys Leu Val Gly Trp Arg Trp Ile Arg Ile Asp Thr Ala
210                 215                 220
Cys Val Cys Thr Leu Leu Ser Arg Thr Gly Arg Thr
225                 230                 235

<210> SEQ ID NO 23
<211> LENGTH: 4
<212> TYPE: PRT
<213> ORGANISM: Homo sapien

<400> SEQUENCE: 23

Arg Ser Lys Arg
1

<210> SEQ ID NO 24
<211> LENGTH: 4
<212> TYPE: PRT
<213> ORGANISM: Homo sapien

<400> SEQUENCE: 24

Arg Val Arg Arg
1

<210> SEQ ID NO 25
<211> LENGTH: 4
<212> TYPE: PRT
<213> ORGANISM: Homo sapien

<400> SEQUENCE: 25

Arg Arg Lys Arg
1

<210> SEQ ID NO 26
<211> LENGTH: 4
<212> TYPE: PRT
<213> ORGANISM: Homo sapien

<400> SEQUENCE: 26

Arg Ser Arg Arg
1
```

```
<210> SEQ ID NO 27
<211> LENGTH: 4
<212> TYPE: PRT
<213> ORGANISM: Artificial sequence
<220> FEATURE:
<223> OTHER INFORMATION: Synthetic Oligopeptide

<400> SEQUENCE: 27

Arg Ser Ala Thr
1

<210> SEQ ID NO 28
<211> LENGTH: 4
<212> TYPE: PRT
<213> ORGANISM: Artificial sequence
<220> FEATURE:
<223> OTHER INFORMATION: Synthetic Oligopeptide

<400> SEQUENCE: 28

Gly Gly Ala Pro
1

<210> SEQ ID NO 29
<211> LENGTH: 4
<212> TYPE: PRT
<213> ORGANISM: Artificial sequence
<220> FEATURE:
<223> OTHER INFORMATION: Synthetic Oligopeptide

<400> SEQUENCE: 29

Ser Ser Thr Pro
1

<210> SEQ ID NO 30
<211> LENGTH: 4
<212> TYPE: PRT
<213> ORGANISM: Artificial sequence
<220> FEATURE:
<223> OTHER INFORMATION: Synthetic Oligopeptide

<400> SEQUENCE: 30

Arg Ser Ala Ala
1

<210> SEQ ID NO 31
<211> LENGTH: 4
<212> TYPE: PRT
<213> ORGANISM: Artificial sequence
<220> FEATURE:
<223> OTHER INFORMATION: Synthetic Oligopeptide

<400> SEQUENCE: 31

Arg Val Ala Ala
1

<210> SEQ ID NO 32
<211> LENGTH: 4
<212> TYPE: PRT
<213> ORGANISM: Artificial sequence
<220> FEATURE:
<223> OTHER INFORMATION: Synthetic Oligopeptide

<400> SEQUENCE: 32

Ala Ala Ala Ala
1
```

```
<210> SEQ ID NO 33
<211> LENGTH: 121
<212> TYPE: PRT
<213> ORGANISM: Homo sapien

<400> SEQUENCE: 33

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ile Ala Ala Arg Val Ala
50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg
        115                 120

<210> SEQ ID NO 34
<211> LENGTH: 120
<212> TYPE: PRT
<213> ORGANISM: Homo sapien

<400> SEQUENCE: 34

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 35
<211> LENGTH: 125
<212> TYPE: PRT
<213> ORGANISM: Rattus norvegicus

<400> SEQUENCE: 35

Val His Ser Val Met Ser Met Leu Phe Tyr Thr Leu Ile Thr Ala Phe
1               5                   10                  15

Leu Ile Gly Val Gln Ala Glu Pro Tyr Thr Asp Ser Asn Val Pro Glu
            20                  25                  30

Gly Asp Ser Val Pro Glu Ala His Trp Thr Lys Leu Gln His Ser Leu
        35                  40                  45
```

-continued

Asp Thr Ala Leu Arg Arg Ala Arg Ser Ala Pro Ala Glu Pro Ile Ala
         50                  55                  60

Ala Arg Val Thr Gly Gln Thr Arg Asn Ile Thr Val Asp Pro Lys Leu
 65                  70                  75                  80

Phe Lys Lys Arg Arg Leu Arg Ser Pro Arg Val Leu Phe Ser Thr Gln
                 85                  90                  95

Pro Pro Pro Thr Ser Ser Asp Thr Leu Asp Leu Asp Phe Gln Ala His
             100                 105                 110

Gly Thr Ile Ser Phe Asn Arg Thr His Arg Ser Lys Arg
             115                 120                 125

<210> SEQ ID NO 36
<211> LENGTH: 120
<212> TYPE: PRT
<213> ORGANISM: Rattus norvegicus

<400> SEQUENCE: 36

Ser Ser Thr His Pro Val Phe His Met Gly Glu Phe Ser Val Cys Asp
 1               5                  10                  15

Ser Val Ser Val Trp Val Gly Asp Lys Thr Thr Ala Thr Asp Ile Lys
                20                  25                  30

Gly Lys Glu Val Thr Val Leu Gly Glu Val Asn Ile Asn Asn Ser Val
             35                  40                  45

Phe Lys Gln Tyr Phe Phe Glu Thr Lys Cys Arg Ala Pro Asn Pro Val
 50                  55                  60

Glu Ser Gly Cys Arg Gly Ile Asp Ser Lys His Trp Asn Ser Tyr Cys
 65                  70                  75                  80

Thr Thr Thr His Thr Phe Val Lys Ala Leu Thr Thr Asp Asp Lys Gln
                 85                  90                  95

Ala Ala Trp Arg Phe Ile Arg Ile Asp Thr Ala Cys Val Cys Val Leu
             100                 105                 110

Ser Arg Lys Ala Ala Arg Gly
             115                 120

<210> SEQ ID NO 37
<211> LENGTH: 121
<212> TYPE: PRT
<213> ORGANISM: Mus musculus

<400> SEQUENCE: 37

Met Ser Met Leu Phe Tyr Thr Leu Ile Thr Ala Phe Leu Ile Gly Val
 1               5                  10                  15

Gln Ala Glu Pro Tyr Thr Asp Ser Asn Val Pro Glu Gly Asp Ser Val
                20                  25                  30

Pro Glu Ala His Trp Thr Lys Leu Gln His Ser Leu Asp Thr Ala Leu
             35                  40                  45

Arg Arg Ala Arg Ser Ala Pro Thr Ala Pro Ile Ala Ala Arg Val Thr
 50                  55                  60

Gly Gln Thr Arg Asn Ile Thr Val Asp Pro Arg Leu Phe Lys Lys Arg
 65                  70                  75                  80

Arg Leu His Ser Pro Arg Val Leu Phe Ser Thr Gln Pro Pro Pro Thr
                 85                  90                  95

Ser Ser Asp Thr Leu Asp Leu Asp Phe Gln Ala His Gly Thr Ile Pro
             100                 105                 110

Phe Asn Arg Thr His Arg Ser Lys Arg
             115                 120

<210> SEQ ID NO 38
<211> LENGTH: 120
<212> TYPE: PRT
<213> ORGANISM: Mus musculus

<400> SEQUENCE: 38

Ser Ser Thr His Pro Val Phe His Met Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Thr Val Leu Ala Glu Val Asn Ile Asn Asn Ser Val
        35                  40                  45

Phe Arg Gln Tyr Phe Phe Glu Thr Lys Cys Arg Ala Ser Asn Pro Val
    50                  55                  60

Glu Ser Gly Cys Arg Gly Ile Asp Ser Lys His Trp Asn Ser Tyr Cys
65                  70                  75                  80

Thr Thr Thr His Thr Phe Val Lys Ala Leu Thr Thr Asp Glu Lys Gln
                85                  90                  95

Ala Ala Trp Arg Phe Ile Arg Ile Asp Thr Ala Cys Val Cys Val Leu
            100                 105                 110

Ser Arg Lys Ala Thr Arg Arg Gly
        115                 120

<210> SEQ ID NO 39
<211> LENGTH: 125
<212> TYPE: PRT
<213> ORGANISM: Gallus gallus

<400> SEQUENCE: 39

Val His Ser Val Met Ser Met Leu Tyr Tyr Thr Leu Ile Ile Ala Phe
1               5                   10                  15

Leu Ile Gly Thr Gln Ala Ala Pro Lys Ser Glu Asp Asn Gly Pro Leu
            20                  25                  30

Glu Tyr Pro Ala Glu His Ser Leu Pro Ser Thr Gln Gln Ser Asn Gly
        35                  40                  45

Gln His Ile Ala Lys Ala Ala Pro Gln Thr Thr His Gly Arg Phe Ala
    50                  55                  60

Trp Met Pro Asp Gly Thr Glu Asp Leu Asn Ile Ala Met Asp Gln Asn
65                  70                  75                  80

Phe Phe Lys Lys Lys Arg Phe Arg Ser Ser Arg Val Leu Phe Ser Thr
                85                  90                  95

Gln Pro Pro Pro Val Ser Arg Lys Gly Gln Ser Thr Gly Phe Leu Ser
            100                 105                 110

Ser Ala Val Ser Leu Asn Arg Thr Ala Arg Thr Lys Arg
        115                 120                 125

<210> SEQ ID NO 40
<211> LENGTH: 118
<212> TYPE: PRT
<213> ORGANISM: Gallus gallus

<400> SEQUENCE: 40

Thr Ala His Pro Val Leu His Arg Gly Glu Phe Ser Val Cys Asp Ser
1               5                   10                  15

Val Ser Met Trp Val Gly Asp Lys Thr Thr Ala Thr Asp Ile Lys Gly
            20                  25                  30

Lys Glu Val Thr Val Leu Gly Glu Val Asn Ile Asn Asn Asn Val Phe
        35                  40                  45

```
Lys Gln Tyr Phe Phe Glu Thr Lys Cys Arg Asp Pro Arg Pro Val Ser
 50                  55                  60

Ser Gly Cys Arg Gly Ile Asp Ala Lys His Trp Asn Ser Tyr Cys Thr
 65                  70                  75                  80

Thr Thr His Thr Phe Val Lys Ala Leu Thr Met Glu Gly Lys Gln Ala
                 85                  90                  95

Ala Trp Arg Phe Ile Arg Ile Asp Thr Ala Cys Val Cys Val Leu Ser
                100                 105                 110

Arg Lys Ser Gly Arg Pro
                115
```

<210> SEQ ID NO 41
<211> LENGTH: 118
<212> TYPE: PRT
<213> ORGANISM: Xenopus laevis

<400> SEQUENCE: 41

```
Val Asp Arg Val Met Ser Met Leu Tyr Tyr Thr Leu Leu Ile Ala Ile
 1               5                  10                  15

Leu Ile Ser Val Gln Ala Ala Pro Lys Thr Lys Asp His Ala Pro Ala
                 20                  25                  30

Arg Ser Ser Ala Lys Ser Arg Ile Pro His His Thr His Arg Thr Lys
             35                  40                  45

Ser Leu His His Ser His Gly Lys Leu Glu Ala Lys Glu Pro Ser Tyr
 50                  55                  60

Phe Arg Asn Val Thr Val Asp Pro Lys Leu Phe Arg Lys Arg Lys Phe
 65                  70                  75                  80

Arg Ser Pro Arg Val Leu Phe Ser Thr Gln Pro Pro Pro Leu Ser Glu
                 85                  90                  95

Asp Phe Gln His Leu Glu Tyr Leu Asp Asp Glu Ser Leu Asn Lys
                100                 105                 110

Thr Ile Arg Ala Lys Arg
                115
```

<210> SEQ ID NO 42
<211> LENGTH: 117
<212> TYPE: PRT
<213> ORGANISM: Xenopus laevis

<400> SEQUENCE: 42

```
Thr Val His Pro Val Leu His Lys Gly Glu Tyr Ser Val Cys Asp Ser
 1               5                  10                  15

Val Ser Met Trp Val Gly Glu Lys Thr Lys Ala Thr Asp Ile Lys Gly
                 20                  25                  30

Lys Glu Val Thr Val Leu Gly Glu Val Asn Ile Asn Asn Ser Val Phe
             35                  40                  45

Lys Gln Tyr Phe Phe Glu Thr Lys Cys Arg Asp Pro Lys Pro Val Ser
 50                  55                  60

Ser Gly Cys Arg Gly Ile Asp Ala Lys His Trp Asn Ser Tyr Cys Thr
 65                  70                  75                  80

Thr Thr His Thr Phe Val Lys Ala Leu Thr Met Glu Gly Lys Gln Ala
                 85                  90                  95

Ala Trp Arg Phe Ile Arg Ile Asp Thr Ala Cys Val Cys Val Leu Ser
                100                 105                 110

Arg Lys Gly Arg Thr
                115
```

```
<210> SEQ ID NO 43
<211> LENGTH: 128
<212> TYPE: PRT
<213> ORGANISM: Homo sapien

<400> SEQUENCE: 43

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

<210> SEQ ID NO 44
<211> LENGTH: 119
<212> TYPE: PRT
<213> ORGANISM: Homo sapien

<400> SEQUENCE: 44

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 45
<211> LENGTH: 130
<212> TYPE: PRT
<213> ORGANISM: Rattus norvegicus

<400> SEQUENCE: 45

Met Thr Ile Leu Phe Leu Thr Met Val Ile Ser Tyr Phe Gly Cys Met
1               5                   10                  15

Lys Ala Ala Pro Met Lys Glu Ala Asn Val His Gly Gln Gly Asn Leu
            20                  25                  30

Ala Tyr Pro Ala Val Arg Thr His Gly Thr Leu Glu Ser Val Asn Gly
        35                  40                  45
```

```
Pro Arg Ala Gly Ser Arg Gly Leu Thr Thr Thr Ser Leu Ala Asp Thr
    50                  55                  60

Phe Glu His Val Ile Glu Leu Leu Asp Glu Asp Gln Lys Val Arg
65                  70                  75                  80

Pro Asn Glu Glu Asn His Lys Asp Ala Asp Leu Tyr Thr Ser Arg Val
                85                  90                  95

Met Leu Ser Ser Gln Val Pro Leu Glu Pro Pro Leu Leu Phe Leu Leu
            100                 105                 110

Glu Glu Tyr Lys Asn Tyr Leu Asp Ala Ala Asn Met Ser Met Arg Val
                115                 120                 125

Arg Arg
    130

<210> SEQ ID NO 46
<211> LENGTH: 119
<212> TYPE: PRT
<213> ORGANISM: Rattus norvegicus

<400> SEQUENCE: 46

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 47
<211> LENGTH: 130
<212> TYPE: PRT
<213> ORGANISM: Mus musculus

<400> SEQUENCE: 47

Met Thr Ile Leu Phe Leu Thr Met Val Ile Ser Tyr Phe Gly Cys Met
1               5                   10                  15

Lys Ala Ala Pro Met Lys Glu Val Asn Val His Gly Gln Gly Asn Leu
            20                  25                  30

Ala Tyr Pro Gly Val Arg Thr His Gly Thr Leu Glu Ser Val Asn Gly
        35                  40                  45

Pro Arg Ala Gly Ser Arg Gly Leu Thr Thr Thr Ser Leu Ala Asp Thr
    50                  55                  60

Phe Glu His Val Ile Glu Leu Leu Asp Glu Asp Gln Lys Val Arg
65                  70                  75                  80

Pro Asn Glu Glu Asn His Lys Asp Ala Asp Leu Tyr Thr Ser Arg Val
                85                  90                  95

Met Leu Ser Ser Gln Val Pro Leu Glu Pro Pro Leu Leu Phe Leu Leu
            100                 105                 110

Glu Glu Tyr Lys Asn Tyr Leu Asp Ala Ala Asn Met Ser Met Arg Val
```

```
<210> SEQ ID NO 48
<211> LENGTH: 119
<212> TYPE: PRT
<213> ORGANISM: Mus musculus

<400> SEQUENCE: 48

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 49
<211> LENGTH: 127
<212> TYPE: PRT
<213> ORGANISM: Gallus gallus

<400> SEQUENCE: 49

Met Thr Ile Leu Phe Leu Thr Met Val Ile Ser Tyr Phe Ser Cys Met
1               5                   10                  15

Lys Ala Ala Pro Met Lys Glu Ala Ser Val Arg Gly His Gly Ser Leu
            20                  25                  30

Ala Tyr Pro Gly Leu Arg Thr His Gly Thr Leu Glu Ser Leu Thr Gly
        35                  40                  45

Pro Asn Ala Gly Ser Arg Gly Leu Thr Ser Leu Ala Asp Thr Phe Glu
    50                  55                  60

His Val Ile Glu Glu Leu Leu Asp Glu Asp Gln Ile Gln Pro Ser
65                  70                  75                  80

Glu Glu Asn Lys Asp Ala Asp Leu Tyr Thr Ser Arg Val Met Leu Ser
                85                  90                  95

Ser Gln Val Pro Leu Glu Pro Pro Leu Leu Phe Leu Leu Glu Glu Tyr
            100                 105                 110

Lys Asn Tyr Leu Asp Ala Ala Asn Met Ser Met Arg Val Arg Arg
        115                 120                 125

<210> SEQ ID NO 50
<211> LENGTH: 119
<212> TYPE: PRT
<213> ORGANISM: Gallus gallus

<400> SEQUENCE: 50

His Ser Asp Pro Ala Arg Arg Gly Glu Leu Ser Val Cys Asp Ser Thr
1               5                   10                  15
```

```
Ser Glu Trp Val Thr Ala Ala Glu Lys Lys Thr Ala Val Asp Met Ser
            20                  25                  30

Gly Ala Thr Val Thr Val Leu Glu Lys Val Pro Val Pro Lys Gly Gln
            35                  40                  45

Leu Lys Gln Tyr Phe Tyr Glu Thr Lys Cys Asn Pro Lys Gly Tyr Thr
        50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Asn Lys Lys
                85                  90                  95

Arg Val Gly Trp Arg Phe Ile Arg Ile Asp Thr Ser Cys Val Cys Thr
            100                 105                 110

Leu Thr Ile Lys Arg Gly Arg
        115

<210> SEQ ID NO 51
<211> LENGTH: 129
<212> TYPE: PRT
<213> ORGANISM: Bos taurus

<400> SEQUENCE: 51

Ile Leu Phe Leu Thr Met Val Ile Ser Tyr Phe Gly Cys Met Lys Ala
1               5                   10                  15

Ala Pro Met Lys Glu Ala Asn Leu Arg Ala Gln Gly Ser Leu Thr Tyr
            20                  25                  30

Pro Gly Val Arg Thr His Gly Thr Leu Glu Ser Met Asn Gly Pro Lys
        35                  40                  45

Val Gly Ser Arg Gly Leu Thr Ser Ser Ser Leu Ala Asp Thr Phe
    50                  55                  60

Glu His Val Ile Glu Glu Leu Leu Asp Glu Asp Gln Lys Val Arg Pro
65                  70                  75                  80

Ser Glu Glu Asn Asn Lys Asp Ala Asp Met Tyr Thr Ser Arg Val Met
                85                  90                  95

Leu Ser Ser Gln Val Pro Leu Glu Pro Pro Leu Leu Phe Leu Leu Glu
            100                 105                 110

Glu Tyr Lys Asn Tyr Leu Asp Ala Ala Asn Met Ser Met Arg Val Arg
        115                 120                 125

Arg

<210> SEQ ID NO 52
<211> LENGTH: 119
<212> TYPE: PRT
<213> ORGANISM: Bos taurus

<400> SEQUENCE: 52

His Ser Asp Pro Ala Arg Arg Gly Glu Leu Ser Val Cys Asp Ser Ile
1               5                   10                  15

Ser Glu Trp Val Thr Ala Ala Asp Lys Arg Leu Ala Val Asp Met Ser
            20                  25                  30

Gly Gly Thr Val Thr Val Leu Glu Lys Val Pro Val Ser Lys Gly Gln
            35                  40                  45

Leu Lys Gln Tyr Phe Tyr Glu Thr Lys Cys Asn Pro Met Gly Tyr Thr
        50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95
```

-continued

```
Arg Ile Gly Trp Arg Phe Ile Arg Ile Asp Thr Ser Cys Val Cys Thr
                100                 105                 110
Leu Thr Ile Lys Arg Gly Arg
        115

<210> SEQ ID NO 53
<211> LENGTH: 138
<212> TYPE: PRT
<213> ORGANISM: Homo sapien

<400> SEQUENCE: 53

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
                100                 105                 110

Glu Pro Pro Pro Leu Tyr Leu Met Glu Asp Tyr Val Gly Ser Pro Val
                115                 120                 125

Val Ala Asn Arg Thr Ser Arg Arg Lys Arg
            130                 135

<210> SEQ ID NO 54
<211> LENGTH: 119
<212> TYPE: PRT
<213> ORGANISM: Homo sapien

<400> SEQUENCE: 54

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
                100                 105                 110

Ser Arg Lys Ile Gly Arg Thr
        115

<210> SEQ ID NO 55
<211> LENGTH: 139
<212> TYPE: PRT
<213> ORGANISM: Rattus norvegicus
```

-continued

<400> SEQUENCE: 55

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Glu Gln Gly Glu Ala Thr Arg Ser
65                  70                  75                  80

Glu Phe Gln Pro Met Ile Ala Thr Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Asn Pro Val
        115                 120                 125

Val Thr Asn Arg Thr Ser Pro Arg Arg Lys Arg
130                 135

<210> SEQ ID NO 56
<211> LENGTH: 119
<212> TYPE: PRT
<213> ORGANISM: Rattus norvegicus

<400> SEQUENCE: 56

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115

<210> SEQ ID NO 57
<211> LENGTH: 139
<212> TYPE: PRT
<213> ORGANISM: Mus musculus

<400> SEQUENCE: 57

Met Ser Ile Leu Phe Tyr Val Ile Phe Leu Ala Tyr Leu Arg Gly Ile
1               5                   10                  15

Gln Gly Asn Ser Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

-continued

```
Lys Ala Glu Ala Pro Arg Glu Pro Gln Gly Glu Ala Thr Arg Ser
 65                  70                  75                  80

Glu Phe Gln Pro Met Ile Ala Thr Asp Thr Glu Leu Leu Arg Gln Gln
                 85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Asn Pro Val
        115                 120                 125

Val Ala Asn Arg Thr Ser Pro Arg Arg Lys Arg
130                 135

<210> SEQ ID NO 58
<211> LENGTH: 119
<212> TYPE: PRT
<213> ORGANISM: Mus musculus

<400> SEQUENCE: 58

Tyr Ala Glu His Lys Ser His Arg Gly Glu Tyr Ser Val Cys Asp Ser
  1               5                  10                  15

Glu Ser Leu Trp Val Thr Asp Lys Ser Ser Ala Ile Asp Ile Arg Gly
                 20                  25                  30

His Gln Val Thr Val Leu Gly Glu Ile Lys Thr Gly Asn Ser Pro Val
             35                  40                  45

Lys Gln Tyr Phe Tyr Glu Thr Arg Cys Lys Glu Ala Arg Pro Val Lys
 50                  55                  60

Asn Gly Cys Arg Gly Ile Asp Asp Lys His Trp Asn Ser Gln Cys Lys
 65                  70                  75                  80

Thr Ser Gln Thr Tyr Val Arg Ala Leu Thr Ser Glu Asn Asn Lys Leu
                 85                  90                  95

Val Gly Trp Arg Trp Ile Arg Ile Asp Thr Ser Cys Val Cys Ala Leu
            100                 105                 110

Ser Arg Lys Ile Gly Arg Thr
        115

<210> SEQ ID NO 59
<211> LENGTH: 138
<212> TYPE: PRT
<213> ORGANISM: Gallus gallus

<400> SEQUENCE: 59

Met Ser Ile Leu Phe Tyr Val Ile Phe Leu Ala Tyr Leu Arg Gly Ile
  1               5                  10                  15

Gln Ser Thr Asn Met Asp Gln Arg Ser Leu Pro Glu Asp Ser Met Asn
                 20                  25                  30

Ser Leu Ile Ile Lys Leu Ile Arg Ala Asp Ile Leu Lys Asn Lys Leu
             35                  40                  45

Ser Lys Gln Val Met Asp Val Lys Glu Asn Tyr Gln Asn Ile Val Gln
 50                  55                  60

Lys Val Glu Asp His Gln Glu Met Asp Gly Asp Glu Asn Val Lys Ser
 65                  70                  75                  80

Asp Phe Gln Pro Val Ile Ser Met Asp Thr Asp Leu Leu Arg Gln Gln
                 85                  90                  95

Arg Arg Tyr Asn Ser Pro Arg Val Leu Leu Ser Asp Asn Thr Pro Leu
            100                 105                 110

Glu Pro Pro Pro Leu Tyr Leu Thr Glu Asp Tyr Val Gly Ser Ser Val
        115                 120                 125
```

```
Val Leu Asn Arg Thr Ser Arg Arg Lys Arg
    130                 135
```

<210> SEQ ID NO 60
<211> LENGTH: 119
<212> TYPE: PRT
<213> ORGANISM: Gallus gallus

<400> SEQUENCE: 60

```
Tyr Ala Glu His Lys Ser His Arg Gly Glu Tyr Ser Val Cys Asp Ser
1               5                  10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Lys Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115
```

<210> SEQ ID NO 61
<211> LENGTH: 141
<212> TYPE: PRT
<213> ORGANISM: Xenopus laevis

<400> SEQUENCE: 61

```
Met Ser Ile Leu Phe Tyr Val Met Phe Leu Pro Tyr Leu Cys Gly Ile
1               5                  10                  15

His Ala Thr Asn Met Asp Lys Arg Asn Leu Pro Glu Asn Ser Met Asn
            20                  25                  30

Ser Leu Phe Ile Lys Leu Ile Gln Ala Asp Leu Leu Lys Asn Lys Ile
        35                  40                  45

Ser Lys Gln Thr Val Asp Thr Lys Glu Asn His Gln Ser Thr Ile Pro
    50                  55                  60

Lys Pro Gln Ile Leu Leu Asp Leu Asp Gly Asp Asn Met Lys Gln
65                  70                  75                  80

Asp Phe Gln Pro Val Ile Ser Leu Glu Ala Glu Leu Val Lys Gln Gln
                85                  90                  95

Lys Gln Arg Arg Tyr Lys Ser Pro Arg Val Leu Leu Ser Asp Ser Leu
            100                 105                 110

Pro Leu Glu Pro Pro Leu Tyr Leu Met Asp Asp Tyr Ile Gly His
        115                 120                 125

Ser Thr Val Val Asn Asn Arg Thr Ser Arg Lys Arg
    130                 135                 140
```

<210> SEQ ID NO 62
<211> LENGTH: 134
<212> TYPE: PRT
<213> ORGANISM: Xenopus laevis

<400> SEQUENCE: 62

```
Phe Ala Glu His Lys Gly His Arg Gly Glu Tyr Ser Val Cys Asp Ser
1               5                  10                  15
```

```
Glu Ser Leu Trp Val Thr Asp Lys Met Asn Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Met
                85                  90                  95

Val Gly Trp Arg Trp Ile Arg Ile Asp Thr Ser Cys Val Cys Ala Leu
            100                 105                 110

Ser Arg Lys Ile Gly Arg Ser Lys Asn Tyr Leu Asp Ala Ala Asn Met
        115                 120                 125

Ser Met Arg Val Arg Arg
    130

<210> SEQ ID NO 63
<211> LENGTH: 80
<212> TYPE: PRT
<213> ORGANISM: Homo sapien

<400> SEQUENCE: 63

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Ser Thr Leu Pro Pro
            20                  25                  30

Pro Phe Leu Ala Pro Glu Trp Asp Leu Leu Ser Pro Arg Val Val Leu
        35                  40                  45

Ser Arg Gly Ala Pro Ala Gly Pro Pro Leu Leu Phe Leu Leu Glu Ala
    50                  55                  60

Gly Ala Phe Arg Glu Ser Ala Gly Ala Pro Ala Asn Arg Ser Arg Arg
65                  70                  75                  80

<210> SEQ ID NO 64
<211> LENGTH: 130
<212> TYPE: PRT
<213> ORGANISM: Homo sapien

<400> SEQUENCE: 64

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
            20                  25                  30

Leu Arg Gly Arg Glu Val Glu Val Leu Gly Glu Val Pro Ala Ala Gly
        35                  40                  45

Gly Ser Pro Leu Arg Gln Tyr Phe Phe Glu Thr Arg Cys Lys Ala Asp
    50                  55                  60

Asn Ala Glu Glu Gly Gly Pro Gly Ala Gly Gly Gly Cys Arg Gly
65                  70                  75                  80

Val Asp Arg Arg His Trp Val Ser Glu Cys Lys Ala Lys Gln Ser Tyr
                85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125
```

Arg Ala
    130

<210> SEQ ID NO 65
<211> LENGTH: 79
<212> TYPE: PRT
<213> ORGANISM: Rattus norvegicus

<400> SEQUENCE: 65

Met Leu Pro Arg His Ser Cys Ser Leu Leu Phe Leu Leu Leu Leu
1               5                   10                  15

Pro Ser Val Pro Met Glu Pro Gln Pro Ser Ser Thr Leu Pro Pro
                20                  25                  30

Phe Leu Ala Pro Glu Trp Asp Leu Leu Ser Pro Arg Val Ala Leu Ser
            35                  40                  45

Arg Gly Thr Pro Ala Gly Pro Pro Leu Leu Phe Leu Leu Glu Ala Gly
        50                  55                  60

Ala Tyr Gly Glu Pro Ala Gly Ala Pro Ala Asn Arg Ser Arg Arg
65                  70                  75

<210> SEQ ID NO 66
<211> LENGTH: 130
<212> TYPE: PRT
<213> ORGANISM: Rattus norvegicus

<400> SEQUENCE: 66

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
                20                  25                  30

Leu Arg Gly Arg Glu Val Glu Val Leu Gly Glu Val Pro Ala Ala Gly
            35                  40                  45

Gly Ser Pro Leu Arg Gln Tyr Phe Phe Glu Thr Arg Cys Lys Ala Glu
        50                  55                  60

Ser Ala Gly Glu Gly Gly Pro Gly Val Gly Gly Gly Cys Arg Gly
65                  70                  75                  80

Val Asp Arg Arg His Trp Leu Ser Glu Cys Lys Ala Lys Gln Ser Tyr
                    85                  90                  95

Val Arg Ala Leu Thr Ala Asp Ser Gln Gly Arg Val Gly Trp Arg Trp
                100                 105                 110

Ile Arg Ile Asp Thr Ala Cys Val Cys Thr Leu Leu Ser Arg Thr Gly
            115                 120                 125

Arg Ala
    130

<210> SEQ ID NO 67
<211> LENGTH: 113
<212> TYPE: PRT
<213> ORGANISM: Xenopus laevis

<400> SEQUENCE: 67

Met Ile Leu Arg Leu Tyr Ala Met Val Ile Ser Tyr Cys Cys Ala Ile
1               5                   10                  15

Cys Ala Ala Pro Phe Gln Ser Arg Thr Thr Asp Leu Asp Tyr Gly Pro
                20                  25                  30

Asp Lys Thr Ser Glu Ala Ser Asp Arg Gln Ser Val Pro Asn Asn Phe
            35                  40                  45

Ser His Val Leu Gln Asn Gly Phe Phe Pro Asp Leu Ser Ser Thr Tyr
        50                  55                  60

```
Ser Ser Met Ala Gly Lys Asp Trp Asn Leu Tyr Ser Pro Arg Val Thr
 65                  70                  75                  80

Leu Ser Ser Glu Glu Pro Ser Gly Pro Pro Leu Leu Phe Leu Ser Glu
                 85                  90                  95

Glu Thr Val Val His Pro Glu Pro Ala Asn Lys Thr Ser Arg Leu Lys
                100                 105                 110

Arg

<210> SEQ ID NO 68
<211> LENGTH: 123
<212> TYPE: PRT
<213> ORGANISM: Xenopus laevis

<400> SEQUENCE: 68

Ala Ser Gly Ser Asp Ser Val Ser Leu Ser Arg Arg Gly Glu Leu Ser
 1               5                  10                  15

Val Cys Asp Ser Val Asn Val Trp Val Thr Asp Lys Arg Thr Ala Val
                20                  25                  30

Asp Asp Arg Gly Lys Ile Val Thr Val Met Ser Glu Ile Gln Thr Leu
             35                  40                  45

Thr Gly Pro Leu Lys Gln Tyr Phe Phe Glu Thr Lys Cys Asn Pro Ser
     50                  55                  60

Gly Ser Thr Thr Arg Gly Cys Arg Gly Val Asp Lys Lys Gln Trp Ile
 65                  70                  75                  80

Ser Glu Cys Lys Ala Lys Gln Ser Tyr Val Arg Ala Leu Thr Ile Asp
                 85                  90                  95

Ala Asn Lys Leu Val Gly Trp Arg Trp Ile Arg Ile Asp Thr Ala Cys
                100                 105                 110

Val Cys Thr Leu Leu Ser Arg Thr Gly Arg Thr
                115                 120

<210> SEQ ID NO 69
<211> LENGTH: 117
<212> TYPE: PRT
<213> ORGANISM: Homo sapiens

<400> SEQUENCE: 69

Met Ser Met Leu Phe Tyr Thr Leu Ile Thr Ala Phe Leu Ile Gly Ile
 1               5                  10                  15

Gln Ala Glu Pro His Ser Glu Ser Asn Val Pro Ala Gly His Thr Ile
                20                  25                  30

Pro Gln Val His Trp Thr Lys Leu Gln His Ser Leu Asp Thr Ala Leu
             35                  40                  45

Arg Arg Ala Arg Ser Ala Pro Ala Ala Ile Ala Ala Arg Val Ala
     50                  55                  60

Gly Gln Thr Arg Asn Ile Thr Val Asp Pro Arg Leu Phe Lys Lys Arg
 65                  70                  75                  80

Arg Leu Arg Ser Pro Arg Val Leu Phe Ser Thr Gln Pro Pro Arg Glu
                 85                  90                  95

Ala Ala Asp Thr Gln Asp Leu Asp Phe Glu Val Gly Gly Ala Ala Pro
                100                 105                 110

Phe Asn Arg Thr His
            115

<210> SEQ ID NO 70
<211> LENGTH: 124
<212> TYPE: PRT
```

<213> ORGANISM: Homo sapiens

<400> SEQUENCE: 70

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Phe Leu Leu Glu Glu
            100                 105                 110

Tyr Lys Asn Tyr Leu Asp Ala Ala Asn Met Ser Met
            115                 120

<210> SEQ ID NO 71
<211> LENGTH: 134
<212> TYPE: PRT
<213> ORGANISM: Homo sapiens

<400> SEQUENCE: 71

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
            115                 120                 125

Val Ala Asn Arg Thr Ser
            130

<210> SEQ ID NO 72
<211> LENGTH: 76
<212> TYPE: PRT
<213> ORGANISM: Homo sapiens

<400> SEQUENCE: 72

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Ser Thr Leu Pro
            20                  25                  30

Pro Phe Leu Ala Pro Glu Trp Asp Leu Leu Ser Pro Arg Val Val Leu
        35                  40                  45

-continued

Ser Arg Gly Ala Pro Ala Gly Pro Pro Leu Leu Phe Leu Leu Glu Ala
            50                  55                  60

Gly Ala Phe Arg Glu Ser Ala Gly Ala Pro Ala Asn
65                  70                  75

<210> SEQ ID NO 73
<211> LENGTH: 20
<212> TYPE: PRT
<213> ORGANISM: Homo sapiens

<400> SEQUENCE: 73

Lys Arg Arg Leu Arg Ser Pro Arg Val Leu Phe Ser Thr Gln Pro Pro
1               5                   10                  15

Arg Glu Ala Ala
            20

<210> SEQ ID NO 74
<211> LENGTH: 15
<212> TYPE: PRT
<213> ORGANISM: Homo sapiens

<400> SEQUENCE: 74

Thr Ser Arg Val Met Leu Ser Ser Gln Val Pro Leu Glu Pro Pro
1               5                   10                  15

<210> SEQ ID NO 75
<211> LENGTH: 15
<212> TYPE: PRT
<213> ORGANISM: Homo sapiens

<400> SEQUENCE: 75

Ser Pro Arg Val Leu Leu Ser Asp Ser Thr Pro Leu Glu Pro Pro
1               5                   10                  15

<210> SEQ ID NO 76
<211> LENGTH: 15
<212> TYPE: PRT
<213> ORGANISM: Homo sapiens

<400> SEQUENCE: 76

Ser Pro Arg Val Val Leu Ser Arg Gly Ala Pro Ala Gly Pro Pro
1               5                   10                  15

<210> SEQ ID NO 77
<211> LENGTH: 19
<212> TYPE: PRT
<213> ORGANISM: Homo sapiens

<400> SEQUENCE: 77

Asp Thr Gln Asp Leu Asp Phe Glu Val Gly Gly Ala Ala Pro Phe Asn
1               5                   10                  15

Arg Thr His

<210> SEQ ID NO 78
<211> LENGTH: 19
<212> TYPE: PRT
<213> ORGANISM: Homo sapiens

<400> SEQUENCE: 78

Leu Leu Phe Leu Leu Glu Glu Tyr Lys Asn Tyr Leu Asp Ala Ala Asn
1               5                   10                  15

Met Ser Met

```
<210> SEQ ID NO 79
<211> LENGTH: 19
<212> TYPE: PRT
<213> ORGANISM: Homo sapiens

<400> SEQUENCE: 79

Pro Leu Tyr Leu Met Glu Asp Tyr Val Gly Ser Pro Val Val Ala Asn
1               5                   10                  15

Arg Thr Ser

<210> SEQ ID NO 80
<211> LENGTH: 19
<212> TYPE: PRT
<213> ORGANISM: Homo sapiens

<400> SEQUENCE: 80

Leu Leu Phe Leu Leu Glu Ala Gly Ala Phe Arg Glu Ser Ala Gly Ala
1               5                   10                  15

Pro Ala Asn

<210> SEQ ID NO 81
<211> LENGTH: 13
<212> TYPE: PRT
<213> ORGANISM: Homo sapiens

<400> SEQUENCE: 81

Gln Thr Arg Asn Ile Thr Val Asp Pro Arg Leu Phe Lys
1               5                   10

<210> SEQ ID NO 82
<211> LENGTH: 18
<212> TYPE: PRT
<213> ORGANISM: Homo sapiens

<400> SEQUENCE: 82

Glu Asp Gln Lys Val Arg Pro Asn Glu Glu Asn Asn Lys Asp Ala Asp
1               5                   10                  15

Leu Tyr

<210> SEQ ID NO 83
<211> LENGTH: 18
<212> TYPE: PRT
<213> ORGANISM: Homo sapiens

<400> SEQUENCE: 83

Gln Pro Val Ile Ala Met Asp Thr Glu Leu Leu Arg Gln Gln Arg Arg
1               5                   10                  15

Tyr Asn

<210> SEQ ID NO 84
<211> LENGTH: 18
<212> TYPE: PRT
<213> ORGANISM: Homo sapiens

<400> SEQUENCE: 84

Gln Pro Pro Pro Ser Thr Leu Pro Pro Phe Leu Ala Pro Glu Trp Asp
1               5                   10                  15

Leu Leu

<210> SEQ ID NO 85
<211> LENGTH: 20
<212> TYPE: PRT
<213> ORGANISM: Homo sapiens
```

<400> SEQUENCE: 85

Thr Ala Leu Arg Arg Ala Arg Ser Ala Pro Ala Ala Ile Ala Ala
1               5                   10                  15

Arg Val Ala Gly
            20

<210> SEQ ID NO 86
<211> LENGTH: 16
<212> TYPE: PRT
<213> ORGANISM: Homo sapiens

<400> SEQUENCE: 86

Thr Ser Leu Ala Asp Thr Phe Glu His Val Ile Glu Glu Leu Leu Asp
1               5                   10                  15

<210> SEQ ID NO 87
<211> LENGTH: 22
<212> TYPE: PRT
<213> ORGANISM: Homo sapiens

<400> SEQUENCE: 87

Ser Thr Leu Pro Lys Ala Glu Ala Pro Arg Glu Pro Glu Arg Gly Gly
1               5                   10                  15

Pro Ala Lys Ser Ala Phe
            20

<210> SEQ ID NO 88
<211> LENGTH: 72
<212> TYPE: PRT
<213> ORGANISM: Homo sapiens

<400> SEQUENCE: 88

Thr Ala Leu Arg Arg Ala Arg Ser Ala Pro Ala Ala Ile Ala Ala
1               5                   10                  15

Arg Val Ala Gly Gln Thr Arg Asn Ile Thr Val Asp Pro Arg Leu Phe
            20                  25                  30

Lys Lys Arg Arg Leu Arg Ser Pro Arg Val Leu Phe Ser Thr Gln Pro
        35                  40                  45

Pro Arg Glu Ala Ala Asp Thr Gln Asp Leu Asp Phe Glu Val Gly Gly
    50                  55                  60

Ala Ala Pro Phe Asn Arg Thr His
65                  70

<210> SEQ ID NO 89
<211> LENGTH: 68
<212> TYPE: PRT
<213> ORGANISM: Homo sapiens

<400> SEQUENCE: 89

Thr Ser Leu Ala Asp Thr Phe Glu His Val Ile Glu Glu Leu Leu Asp
1               5                   10                  15

Glu Asp Gln Lys Val Arg Pro Asn Glu Glu Asn Asn Lys Asp Ala Asp
            20                  25                  30

Leu Tyr Thr Ser Arg Val Met Leu Ser Ser Gln Val Pro Leu Glu Pro
        35                  40                  45

Pro Leu Leu Phe Leu Leu Glu Glu Tyr Lys Asn Tyr Leu Asp Ala Ala
    50                  55                  60

Asn Met Ser Met
65

<210> SEQ ID NO 90
<211> LENGTH: 74
<212> TYPE: PRT
<213> ORGANISM: Homo sapiens

<400> SEQUENCE: 90

Ser Thr Leu Pro Lys Ala Glu Ala Pro Arg Glu Pro Glu Arg Gly Gly
1               5                   10                  15

Pro Ala Lys Ser Ala Phe Gln Pro Val Ile Ala Met Asp Thr Glu Leu
            20                  25                  30

Leu Arg Gln Gln Arg Arg Tyr Asn Ser Pro Arg Val Leu Leu Ser Asp
        35                  40                  45

Ser Thr Pro Leu Glu Pro Pro Pro Leu Tyr Leu Met Glu Asp Tyr Val
    50                  55                  60

Gly Ser Pro Val Val Ala Asn Arg Thr Ser
65                  70

<210> SEQ ID NO 91
<211> LENGTH: 52
<212> TYPE: PRT
<213> ORGANISM: Homo sapiens

<400> SEQUENCE: 91

Gln Pro Pro Pro Ser Thr Leu Pro Pro Phe Leu Ala Pro Glu Trp Asp
1               5                   10                  15

Leu Leu Ser Pro Arg Val Val Leu Ser Arg Gly Ala Pro Ala Gly Pro
            20                  25                  30

Pro Leu Leu Phe Leu Leu Glu Ala Gly Ala Phe Arg Glu Ser Ala Gly
        35                  40                  45

Ala Pro Ala Asn
    50

<210> SEQ ID NO 92
<211> LENGTH: 18
<212> TYPE: PRT
<213> ORGANISM: Homo sapiens

<400> SEQUENCE: 92

Met Ser Met Leu Phe Tyr Thr Leu Ile Thr Ala Phe Leu Ile Gly Ile
1               5                   10                  15

Gln Ala

<210> SEQ ID NO 93
<211> LENGTH: 18
<212> TYPE: PRT
<213> ORGANISM: Homo sapiens

<400> SEQUENCE: 93

Met Thr Ile Leu Phe Leu Thr Met Val Ile Ser Tyr Phe Gly Cys Met
1               5                   10                  15

Lys Ala

<210> SEQ ID NO 94
<211> LENGTH: 18
<212> TYPE: PRT
<213> ORGANISM: Homo sapiens

<400> SEQUENCE: 94

Met Ser Ile Leu Phe Tyr Val Ile Phe Leu Ala Tyr Leu Arg Gly Ile
1               5                   10                  15

Gln Gly

```
<210> SEQ ID NO 95
<211> LENGTH: 24
<212> TYPE: PRT
<213> ORGANISM: Homo sapiens

<400> SEQUENCE: 95
```

Met Leu Pro Leu Pro Ser Cys Ser Leu Pro Ile Leu Leu Phe Leu
1               5                   10                  15

Leu Pro Ser Val Pro Ile Glu Ser
            20

```
<210> SEQ ID NO 96
<211> LENGTH: 120
<212> TYPE: PRT
<213> ORGANISM: Homo sapiens

<400> SEQUENCE: 96
```

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

```
<210> SEQ ID NO 97
<211> LENGTH: 119
<212> TYPE: PRT
<213> ORGANISM: Homo sapiens

<400> SEQUENCE: 97
```

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

-continued

<210> SEQ ID NO 98
<211> LENGTH: 119
<212> TYPE: PRT
<213> ORGANISM: Homo sapiens

<400> SEQUENCE: 98

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115

<210> SEQ ID NO 99
<211> LENGTH: 130
<212> TYPE: PRT
<213> ORGANISM: Homo sapiens

<400> SEQUENCE: 99

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
            20                  25                  30

Leu Arg Gly Arg Glu Val Glu Val Leu Gly Glu Val Pro Ala Ala Gly
        35                  40                  45

Gly Ser Pro Leu Arg Gln Tyr Phe Phe Glu Thr Arg Cys Lys Ala Asp
    50                  55                  60

Asn Ala Glu Glu Gly Gly Pro Gly Ala Gly Gly Gly Cys Arg Gly
65                  70                  75                  80

Val Asp Arg Arg His Trp Val Ser Glu Cys Lys Ala Lys Gln Ser Tyr
                85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125

Arg Ala
    130

<210> SEQ ID NO 100
<211> LENGTH: 99
<212> TYPE: PRT
<213> ORGANISM: Homo sapiens

<400> SEQUENCE: 100

Glu Pro His Ser Glu Ser Asn Val Pro Ala Gly His Thr Ile Pro Gln
1               5                   10                  15

Val His Trp Thr Lys Leu Gln His Ser Leu Asp Thr Ala Leu Arg Arg
            20                  25                  30

```
Ala Arg Ser Ala Pro Ala Ala Ile Ala Arg Val Ala Gly Gln
        35                  40                  45

Thr Arg Asn Ile Thr Val Asp Pro Arg Leu Phe Lys Lys Arg Arg Leu
 50                  55                  60

Arg Ser Pro Arg Val Leu Phe Ser Thr Gln Pro Pro Arg Glu Ala Ala
 65                  70                  75                  80

Asp Thr Gln Asp Leu Asp Phe Glu Val Gly Gly Ala Ala Pro Phe Asn
                 85                  90                  95

Arg Thr His

<210> SEQ ID NO 101
<211> LENGTH: 67
<212> TYPE: PRT
<213> ORGANISM: Homo sapiens

<400> SEQUENCE: 101

Ala Arg Ser Ala Pro Ala Ala Ile Ala Arg Val Ala Gly Gln
 1               5                  10                  15

Thr Arg Asn Ile Thr Val Asp Pro Arg Leu Phe Lys Lys Arg Arg Leu
             20                  25                  30

Arg Ser Pro Arg Val Leu Phe Ser Thr Gln Pro Pro Arg Glu Ala Ala
         35                  40                  45

Asp Thr Gln Asp Leu Asp Phe Glu Val Gly Gly Ala Ala Pro Phe Asn
     50                  55                  60

Arg Thr His
 65

<210> SEQ ID NO 102
<211> LENGTH: 37
<212> TYPE: PRT
<213> ORGANISM: Homo sapiens

<400> SEQUENCE: 102

Arg Leu Arg Ser Pro Arg Val Leu Phe Ser Thr Gln Pro Pro Arg Glu
 1               5                  10                  15

Ala Ala Asp Thr Gln Asp Leu Asp Phe Glu Val Gly Gly Ala Ala Pro
             20                  25                  30

Phe Asn Arg Thr His
         35

<210> SEQ ID NO 103
<211> LENGTH: 36
<212> TYPE: PRT
<213> ORGANISM: Homo sapiens

<400> SEQUENCE: 103

Leu Arg Ser Pro Arg Val Leu Phe Ser Thr Gln Pro Pro Arg Glu Ala
 1               5                  10                  15

Ala Asp Thr Gln Asp Leu Asp Phe Glu Val Gly Gly Ala Ala Pro Phe
             20                  25                  30

Asn Arg Thr His
         35

<210> SEQ ID NO 104
<211> LENGTH: 106
<212> TYPE: PRT
<213> ORGANISM: Homo sapiens

<400> SEQUENCE: 104
```

Ala Pro Met Lys Glu Ala Asn Ile Arg Gly Gln Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met
            100                 105

<210> SEQ ID NO 105
<211> LENGTH: 67
<212> TYPE: PRT
<213> ORGANISM: Homo sapiens

<400> SEQUENCE: 105

Ser Leu Ala Asp Thr Phe Glu His Val Ile Glu Glu Leu Leu Asp Glu
1               5                   10                  15

Asp Gln Lys Val Arg Pro Asn Glu Glu Asn Asn Lys Asp Ala Asp Leu
            20                  25                  30

Tyr Thr Ser Arg Val Met Leu Ser Ser Gln Val Pro Leu Glu Pro Pro
        35                  40                  45

Leu Leu Phe Leu Leu Glu Glu Tyr Lys Asn Tyr Leu Asp Ala Ala Asn
    50                  55                  60

Met Ser Met
65

<210> SEQ ID NO 106
<211> LENGTH: 15
<212> TYPE: PRT
<213> ORGANISM: Homo sapiens

<400> SEQUENCE: 106

Leu Glu Glu Tyr Lys Asn Tyr Leu Asp Ala Ala Asn Met Ser Met
1               5                   10                  15

<210> SEQ ID NO 107
<211> LENGTH: 14
<212> TYPE: PRT
<213> ORGANISM: Homo sapiens

<400> SEQUENCE: 107

Glu Glu Tyr Lys Asn Tyr Leu Asp Ala Ala Asn Met Ser Met
1               5                   10

<210> SEQ ID NO 108
<211> LENGTH: 12
<212> TYPE: PRT
<213> ORGANISM: Homo sapiens

<400> SEQUENCE: 108

Tyr Lys Asn Tyr Leu Asp Ala Ala Asn Met Ser Met
1               5                   10

<210> SEQ ID NO 109
<211> LENGTH: 116

<212> TYPE: PRT
<213> ORGANISM: Homo sapiens

<400> SEQUENCE: 109

Asn Asn Met Asp Gln Arg Ser Leu Pro Glu Asp Ser Leu Asn Ser Leu
1               5                   10                  15

Ile Ile Lys Leu Ile Gln Ala Asp Ile Leu Lys Asn Lys Leu Ser Lys
            20                  25                  30

Gln Met Val Asp Val Lys Glu Asn Tyr Gln Ser Thr Leu Pro Lys Ala
        35                  40                  45

Glu Ala Pro Arg Glu Pro Glu Arg Gly Gly Pro Ala Lys Ser Ala Phe
    50                  55                  60

Gln Pro Val Ile Ala Met Asp Thr Glu Leu Leu Arg Gln Gln Arg Arg
65                  70                  75                  80

Tyr Asn Ser Pro Arg Val Leu Leu Ser Asp Ser Thr Pro Leu Glu Pro
                85                  90                  95

Pro Pro Leu Tyr Leu Met Glu Asp Tyr Val Gly Ser Pro Val Val Ala
            100                 105                 110

Asn Arg Thr Ser
        115

<210> SEQ ID NO 110
<211> LENGTH: 36
<212> TYPE: PRT
<213> ORGANISM: Homo sapiens

<400> SEQUENCE: 110

Tyr Asn Ser Pro Arg Val Leu Leu Ser Asp Ser Thr Pro Leu Glu Pro
1               5                   10                  15

Pro Pro Leu Tyr Leu Met Glu Asp Tyr Val Gly Ser Pro Val Val Ala
            20                  25                  30

Asn Arg Thr Ser
        35

<210> SEQ ID NO 111
<211> LENGTH: 52
<212> TYPE: PRT
<213> ORGANISM: Homo sapiens

<400> SEQUENCE: 111

Gln Pro Pro Pro Ser Thr Leu Pro Pro Phe Leu Ala Pro Glu Trp Asp
1               5                   10                  15

Leu Leu Ser Pro Arg Val Val Leu Ser Arg Gly Ala Pro Ala Gly Pro
            20                  25                  30

Pro Leu Leu Phe Leu Leu Glu Ala Gly Ala Phe Arg Glu Ser Ala Gly
            35                  40                  45

Ala Pro Ala Asn
    50

<210> SEQ ID NO 112
<211> LENGTH: 15
<212> TYPE: PRT
<213> ORGANISM: Homo sapiens

<400> SEQUENCE: 112

Leu Glu Ala Gly Ala Phe Arg Glu Ser Ala Gly Ala Pro Ala Asn
1               5                   10                  15

<210> SEQ ID NO 113
<211> LENGTH: 14

```
<212> TYPE: PRT
<213> ORGANISM: Homo sapiens

<400> SEQUENCE: 113

Glu Ala Gly Ala Phe Arg Glu Ser Ala Gly Ala Pro Ala Asn
1               5                   10

<210> SEQ ID NO 114
<211> LENGTH: 15
<212> TYPE: PRT
<213> ORGANISM: Homo sapiens

<400> SEQUENCE: 114

Ser Pro Arg Val Leu Phe Ser Thr Gln Pro Pro Arg Glu Ala Ala
1               5                   10                  15

<210> SEQ ID NO 115
<211> LENGTH: 5
<212> TYPE: PRT
<213> ORGANISM: Artificial Sequence
<220> FEATURE:
<223> OTHER INFORMATION: Synthetic seqeunce
<220> FEATURE:
<221> NAME/KEY: misc_feature
<222> LOCATION: (1)..(1)
<223> OTHER INFORMATION: X is serine or threonine
<220> FEATURE:
<221> NAME/KEY: MISC_FEATURE
<222> LOCATION: (2)..(2)
<223> OTHER INFORMATION: X is proline or serine
<220> FEATURE:
<221> NAME/KEY: MISC_FEATURE
<222> LOCATION: (5)..(5)
<223> OTHER INFORMATION: Z represents any alpha amino acid.  The number
      of alpha amino acid can be any number from 0 to approximately 20.

<400> SEQUENCE: 115

Xaa Xaa Arg Val Xaa
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X can be serine or threonine
<220> FEATURE:
<221> NAME/KEY: MISC_FEATURE
<222> LOCATION: (2)..(2)
<223> OTHER INFORMATION: X is proline or serine
<220> FEATURE:
<221> NAME/KEY: MISC_FEATURE
<222> LOCATION: (5)..(5)
<223> OTHER INFORMATION: X is leucine, methionine, or valine
<220> FEATURE:
<221> NAME/KEY: MISC_FEATURE
<222> LOCATION: (6)..(6)
<223> OTHER INFORMATION: X is any alpha amino acid.  The number of
      alpha amino acids can be any number from 0 to approximately 20.

<400> SEQUENCE: 116

Xaa Xaa Arg Val Xaa Xaa
1               5

<210> SEQ ID NO 117
<211> LENGTH: 7
<212> TYPE: PRT
<213> ORGANISM: Artificial Sequence
```

```
<220> FEATURE:
<223> OTHER INFORMATION: Synthetic seqeunce
<220> FEATURE:
<221> NAME/KEY: MISC_FEATURE
<222> LOCATION: (1)..(1)
<223> OTHER INFORMATION: X is serine or threonine
<220> FEATURE:
<221> NAME/KEY: MISC_FEATURE
<222> LOCATION: (2)..(2)
<223> OTHER INFORMATION: X is proline or serine
<220> FEATURE:
<221> NAME/KEY: MISC_FEATURE
<222> LOCATION: (5)..(5)
<223> OTHER INFORMATION: X is leucine, methionine, or valine
<220> FEATURE:
<221> NAME/KEY: MISC_FEATURE
<222> LOCATION: (6)..(6)
<223> OTHER INFORMATION: X is phenylalanine or leucine
<220> FEATURE:
<221> NAME/KEY: MISC_FEATURE
<222> LOCATION: (7)..(7)
<223> OTHER INFORMATION: X is any alpha amino acid.  The number of alpha
      amino acid can be any number from 0 to approximately 20.

<400> SEQUENCE: 117

Xaa Xaa Arg Val Xaa Xaa Xaa
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic seqeunce
<220> FEATURE:
<221> NAME/KEY: MISC_FEATURE
<222> LOCATION: (1)..(1)
<223> OTHER INFORMATION: X is serine of threonine
<220> FEATURE:
<221> NAME/KEY: MISC_FEATURE
<222> LOCATION: (2)..(2)
<223> OTHER INFORMATION: X is proline or serine
<220> FEATURE:
<221> NAME/KEY: MISC_FEATURE
<222> LOCATION: (5)..(5)
<223> OTHER INFORMATION: X is leucine, methionine, or valine
<220> FEATURE:
<221> NAME/KEY: MISC_FEATURE
<222> LOCATION: (6)..(6)
<223> OTHER INFORMATION: X is phenylalamine or leucine
<220> FEATURE:
<221> NAME/KEY: MISC_FEATURE
<222> LOCATION: (8)..(8)
<223> OTHER INFORMATION: X is any alpha amino acid.  The number of alpha
      amino acids can be any number from 0 to approximately 20.

<400> SEQUENCE: 118

Xaa Xaa Arg Val Xaa Xaa Ser Xaa
1               5
```